United States Patent
Shirakura et al.

(10) Patent No.: US 10,301,300 B2
(45) Date of Patent: *May 28, 2019

(54) XANTHINE OXIDASE INHIBITOR

(71) Applicant: TEIJIN LIMITED, Osaka-shi, Osaka (JP)

(72) Inventors: Takashi Shirakura, Tokyo (JP); Yoshimasa Takahashi, Tokyo (JP); Asahi Kawana, Tokyo (JP); Chikashi Kanazawa, Tokyo (JP)

(73) Assignee: TEIJIN LIMITED, Osaka-shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,227

(22) Filed: May 1, 2018

(65) Prior Publication Data

US 2018/0244665 A1    Aug. 30, 2018

Related U.S. Application Data

(63) Continuation of application No. 15/329,695, filed as application No. PCT/JP2015/072153 on Jul. 29, 2015, now abandoned.

(30) Foreign Application Priority Data

Jul. 30, 2014   (JP) ................... 2014-155029

(51) Int. Cl.
*A61K 31/427* (2006.01)
*C07D 417/10* (2006.01)
*C07D 417/14* (2006.01)

(52) U.S. Cl.
CPC .......... *C07D 417/10* (2013.01); *A61K 31/427* (2013.01); *C07D 417/14* (2013.01)

(58) Field of Classification Search
CPC ................................................. A61K 31/427
See application file for complete search history.

(56) References Cited

U.S. PATENT DOCUMENTS

| | | | |
|---|---|---|---|
| 5,614,520 A | 3/1997 | Kondo et al. | |
| 5,843,969 A | 12/1998 | Ota et al. | |
| 9,388,174 B2 | 7/2016 | Kawana et al. | |
| 9,815,826 B2* | 11/2017 | Kawana | C07D 417/10 |
| 2004/0122067 A1 | 6/2004 | Zhao | |
| 2009/0306396 A1 | 12/2009 | Toyoshima et al. | |
| 2010/0022592 A1 | 1/2010 | Epple et al. | |
| 2010/0227864 A1 | 9/2010 | Shimizu et al. | |
| 2014/0249318 A1 | 9/2014 | Nakatsuji et al. | |
| 2015/0376174 A1 | 12/2015 | Kawana et al. | |
| 2017/0217948 A1* | 8/2017 | Shirakura | C07D 417/10 |
| 2017/0247364 A1* | 8/2017 | Kawana | C07D 417/10 |

FOREIGN PATENT DOCUMENTS

| | | |
|---|---|---|
| JP | 2002-105067 A | 4/2002 |
| JP | 2006-514051 A | 4/2006 |
| JP | 2010-519258 A | 6/2010 |
| JP | 5734532 B2 | 6/2015 |
| WO | 92/009279 A1 | 6/1992 |
| WO | 96/031211 A1 | 10/1996 |
| WO | 2007/043400 A1 | 4/2007 |
| WO | 2008/126770 A1 | 10/2008 |
| WO | 2008/126899 A1 | 10/2008 |
| WO | 2010/018458 A2 | 2/2010 |
| WO | 2010/128163 A2 | 11/2010 |
| WO | 2011/101867 A2 | 8/2011 |
| WO | 2011/139886 A2 | 11/2011 |
| WO | 2013/054940 A1 | 4/2013 |
| WO | 2014/119681 A1 | 8/2014 |

OTHER PUBLICATIONS

Pal Pacher et al., "Therapeutic Effects of Xanthine Oxidase Inhibitors: Renaissance Half a Century after the Discovery of Allopurinol", Pharmacol. Rev., vol. 58, No. 1, 2006, pp. 87-111.

Ali Momeni et al., "Effect of Allopurinol in Decreasing Proteinuria in Type 2 Diabetic Patients", Iranian Journal of Kidney Diseases, vol. 4, No. 2, Apr. 2010, pp. 128-132.

Su-Mi Kim et al., "Reducing Serum Uric Acid Attenuates TGF-$\beta_1$-Induced Profibrogenic Progression in Type 2 Diabetic Nephropathy", Nephron Exp. Nephrol., vol. 121, 2012, pp. e109-e121.

Tomoki Kosugi et al., "Effect of lowering uric acid on renal disease in the type 2 diabetic db/db mice", Am. J. Physiol. Renal Physiol., vol. 297, May 20, 2009, pp. F481-F488.

Akifumi Kushiyama et al., "Xanthine Oxidoreductase Is Involved in Macrophage Foam Cell Formation and Atherosclerosis Development", Arterioscler. Thromb. Vasc. Biol., Feb. 2012, pp. 291-298. (16 pages total).

Katrin Schröder et al., "Xanthine oxidase inhibitor tungsten prevents the development of atherosclerosis in ApoE knockout mice fed a Western-type diet", Free Radical Biology & Medicine, vol. 41, 2006, pp. 1353-1360.

Niels Engberding, MD et al., "Allopurinol Attenuates Left Ventricular Remodeling and Dysfunction After Experimental Myocardial Infarction A New Action for an Old Drug?" Circulation, Oct. 12, 2004, pp. 2175-2179.

Xin Xu et al., "Xanthine Oxidase Inhibition With Febuxostat Attenuates Systolic Overload-Induced Left Ventricular Hypertrophy and Dysfunction in Mice", Journal of Cardiac Failure, vol. 14, No. 9, 2008, pp. 746-753.

53rd Annual Meeting of the Japanese Society of Neurology, Tokyo International Forum, Abstract, P(3)-281, May 22-25, 2012. (4 pages total).

(Continued)

*Primary Examiner* — Laura L Stockton
(74) *Attorney, Agent, or Firm* — Sughrue Mion, PLLC

(57) ABSTRACT

Provided are a xanthine oxidase inhibitor, a drug for improving vascular endothelial function, and an excellent therapeutic or prophylactic drug for diseases associated with xanthine oxidase such as gout, hyperuricaemia, and for diseases associated with vascular endothelial functional disorder containing a compound represented in a formula (I) or the pharmaceutically acceptable salt thereof as an active ingredient.

15 Claims, No Drawings

(56) References Cited

OTHER PUBLICATIONS

Josephe Archie Honorat et al., "Xanthine Oxidase Mediates Axonal and Myelin Loss in a Murine Model of Multiple Sclerosis" PLOS One, vol. 8, Issue 8, Aug. 2013, pp. 1-8. (12 pages total).
Marian Goicoechea et al., "Effect of Allopurinol in Chronic Kidney Disease Progression and Cardiovascular Risk", Clin. J. Am. Soc. Nephrol., vol. 5, 2010, pp. 1-6.
Yui-Pong Siu et al., "Use of Allopurinol in Slowing the Progression of Renal Disease Through Its Ability to Lower Serum Uric Acid Level", American Journal of Kidney Diseases, vol. 47, No. 1, Jan. 2006, pp. 51-59.
Akira Sezai, MD et al., "Comparison of Febuxostat and Allopurinol for Hyperuricemia in Cardiac Surgery Patients (NU-FLASH Trial)", Circulation Journal, vol. 77, Aug. 2013, pp. 2043-2049.
Hong-Joo Lee et al., Febuxostat Ameliorates Diabetic Renal Injury in a Streptozotocin-Induced Diabetic Rat Model, American Journal of Nephrology, vol. 40, 2014, pp. 56-63.
Brian E. Lee, BA et al., "Allopurinol, Xanthine Oxidase, and Cardiac Ischemia", Journal of Investigative Medicine, vol. 57, No. 8, Dec. 2009, pp. 902-909.
Jun Xiao et al., "Effect of allopurinol on cardiomyocyte apoptosis in rats after myocardial infraction", European Journal of Heart Failure, vol. 11, 2009, pp. 20-27.
Hidayet Akdemir et al., "The effect of allopurinol on focal cerebral ischaemia: an experimental study in rabbits", Neurosurg. Rev., vol. 24, 2001, pp. 131-135.
Communication dated Feb. 14, 2017 from the Japanese Patent Office in counterpart Application No. 2016-538476.
Chemical Abstracts Registry No. 1621282-95-8, indexed in the Registry file on STN CAS Online Aug. 26, 2014.
Chemical Abstracts Registry No. 1621283-46-2, indexed in the Registry file on STN CAS Online Aug. 26, 2014.
Chemical Abstracts Registry No. 1621283-45-1, indexed in the Registry file on STN CAS Online Aug. 26, 2014.
Chemical Abstracts Registry No. 1621283-11-1, indexed in the Registry file on STN CAS Online Aug. 26, 2014.
International Search Report for PCT/JP2015/072153 dated Nov. 2, 2015 [PCT/ISA/210].
Written Opinion for PCT/JP2015/072153 dated Nov. 2, 2015 [PCT/ISA/210].

\* cited by examiner

XANTHINE OXIDASE INHIBITOR

CROSS-REFERENCE TO THE RELATED APPLICATIONS

This application is a continuation of U.S. patent application Ser. No. 15/329,695, filed Jan. 27, 2017, which is a National Stage of International Application No. PCT/JP2015/072153 filed Jul. 29, 2015, claiming priority based on Japanese Patent Application No. 2014-155029 filed Jul. 30, 2014, the contents of all of which are incorporated herein by reference in their entirety.

TECHNICAL FIELD

The present invention relates to a novel use of a novel compound having a xanthine oxidase inhibitory activity.

BACKGROUND ART

Xanthine oxidase is an enzyme catalyzing the conversion of hypoxanthine to xanthine and further to uric acid in nucleic acid metabolism.

A xanthine oxidase inhibitor inhibits uric acid synthesis to reduce a level of uric acid in the blood with respect to the action of xanthine oxidase. Thus, a xanthine oxidase inhibitor is effective as a therapeutic agent for hyperuricemia and various diseases caused by hyperuricemia. Moreover, there are gouty arthritis and gouty tophus called gout as a clinical condition caused by as a result of deposition of urate crystals after prolonged hyperuricemia. In addition, hyperuricemia is considered to be important as a factor of lifestyle diseases associated with obesity, hypertension, dyslipidemia and diabetes or metabolic syndromes, and recently, it has been clarified that hyperuricemia is a risk factor of renal damage, urinary calculi and cardiovascular diseases by epidemiological studies (guideline for the Management of Hyperuricemia and Gout, 2nd edition). In addition, a xanthine oxidase inhibitor is expected to be useful for a treatment of diseases related to reactive oxygen species by its inhibitory activity on reactive oxygen species generation, for example, a treatment of cardiovascular diseases through improvement of endothelial function (Circulation. 2006; 114:2508-2516).

Allopurinol and febuxostat are clinically used as a therapeutic agent for hyperuricemia, but allopurinol has been reported to have a side effect such as Stevens-Johnson syndrome, toxic epidermal necrolysis, hepatic disorder and renal dysfunction (Nippon Rinsho, 2003; 61, Suppl. 1: 197-201).

As a compound having a xanthine oxidase inhibitory activity, for example, a 2-phenylthiazole derivative is reported (Patent Documents 1 to 3).

On the other hand, in Patent Documents 4 and 5, a dithiazole carboxylic acid derivative having a benzene ring in the center is reported. Further, in Patent Documents 6 and 7, a biphenyl thioazole carboxylic acid derivative is reported.

PRIOR ART DOCUMENTS

Patent Documents

Patent Document 1: International Publication No. 92/09279
Patent Document 2: Japanese Patent Laid-Open No. 2002-105067
Patent Document 3: International Publication No. 96/31211
Patent Document 4: International Publication No. 2011/139886
Patent Document 5: International Publication No. 2011/101867
Patent Document 6: International Publication No. 2010/018458
Patent Document 7: International Publication No. 2010/128163

SUMMARY OF INVENTION

Technical Problem

An object of the present invention is to provide a novel compound having a xanthine oxidase inhibitory activity.

Solution to Problem

As a result of earnest studies, the present inventors have found that a compound represented by the following formula (I):

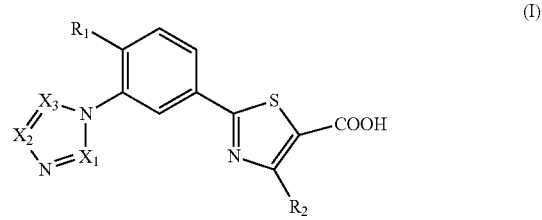

that is, a compound which has a benzene structure having 3 substituents and is an azole benzene derivative having a 2-thiazole ring at a position 1 and a 1,3-nitrogen-containing azole ring at a position 3 is useful for a xanthine oxidase inhibitory agent and a drug for improving vascular endothelial function, and completed the present invention. In addition, the present inventors have found that the azole benzene derivative may serve as a favorable therapeutic or prophylactic agent for diseases associated with xanthine oxidase such as gout, hyperuricemia, tumor lysis syndrome, urinary calculi, hypertension, dyslipidemia, diabetes, kidney diseases such as diabetic nephropathy, respiratory diseases such as chronic obstructive pulmonary disease, inflammatory bowel diseases and autoimmune diseases, and diseases associated with the vascular endothelial functional disorder such as arteriosclerosis, myocardial infarction, cerebral infarction, cerebrovascular dementia, and completed the present invention.

That is, the present invention is a xanthine oxidase inhibitor comprising a compound represented by the following formula (I) or a pharmaceutically acceptable salt thereof as an active ingredient:

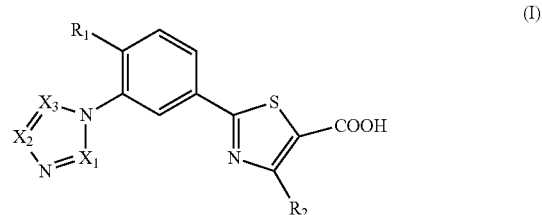

[wherein,
$R_1$ represents OR, NRR' which may form a ring or SR, in which R and R' independently represent a hydrogen atom, an alkyl group having 1 to 8 carbon atoms optionally substituted with one or a plurality of alkoxy groups having 1 to 8 carbon atoms, halogen atoms or hydroxyl groups, or an aryl group optionally substituted with one or a plurality of alkyl groups having 1 to 8 carbon atoms, alkoxy groups having 1 to 8 carbon atoms or halogen atoms, or a heteroaryl group optionally substituted with one or a plurality of alkyl groups having 1 to 8 carbon atoms, alkoxy groups having 1 to 8 carbon atoms or halogen atoms.

$R_2$ represents a hydrogen atom or an alkyl group having 1 to 8 carbon atoms.

$X_1$, $X_2$ and $X_3$ are independently $CR_3$ or a nitrogen atom, or $X_1$ is $CR_3$ or a nitrogen atom, and $X_2$ and $X_3$ together form a benzene ring, in which $R_3$ is a hydrogen atom or an alkyl group having 1 to 8 carbon atoms.]

Also, the present invention is a therapeutic agent or a prophylactic agent for diseases associated with xanthine oxidase, which contains a compound represented by the formula (I) or a pharmaceutically acceptable salt thereof as an active ingredient.

Also, the present invention is an agent for improving vascular endothelial function containing a compound represented by the formula (I) or a pharmaceutically acceptable salt thereof as an active ingredient.

Also, the present invention is a therapeutic agent or a prophylactic agent for diseases associated with vascular endothelial function disorder containing a compound represented by the formula (I) or a pharmaceutically acceptable salt thereof as an active ingredient.

Advantageous Effects of Invention

The present invention provides a novel use for a novel compound having a xanthine oxidase inhibitory activity. In addition, a compound of the present invention is useful as a xanthine oxidase inhibitory drug, a drug for improving vascular endothelial function, a therapeutic agent or a prophylactic agent for diseases associated with xanthine oxidase such as gout, hyperuricemia, tumor lysis syndrome, urinary calculi, hypertension, dyslipidemia, diabetes, kidney diseases such as diabetic nephropathy, respiratory diseases such as chronic obstructive pulmonary disease, inflammatory bowel disease, autoimmune disease, and diseases associated with a vascular endothelial functional disorder such as arteriosclerosis, myocardial infarction, cerebral infarction and cerebrovascular dementia.

DESCRIPTION OF EMBODIMENTS

The terms used singly or in combination in the present description will be explained in the following. Unless otherwise specified, explanation of each substituent shall be common to each position. In addition, if any variables exist in an optional constituent factor in an arbitrary constituent element, the definition is independent in each of constituent elements. Further, a combination of substituents and variables is allowed as long as such a combination results in a chemically stable compound.

Generally "xanthine oxidase" is used as a broad sense, enzymes catalyzing oxidative reactions of hypoxanthine to xanthine and further to uric acid, and a narrow sense, oxidase-type xanthine oxidoreductase which is one of the enzymes catalyzing the reactions, however, in the present invention, "xanthine oxidase" collectively means enzymes catalyzing oxidative reactions of hypoxanthine to xanthine and further to uric acid, unless otherwise noted. Xanthine oxidoreductase which catalyzes such reactions has two types, i.e. oxidase-type and dehydrogenase-type. Both types are included in the "xanthine oxidase" of the present invention. In "xanthine oxidase inhibitory activity", "xanthine oxidase inhibitor" and the like, "xanthine oxidase" has same meanings as defined above, unless otherwise noted.

In the present invention, the term "a halogen atom" means a fluorine atom, a chlorine atom, a bromine atom, or an iodine atom.

In the present invention, the term "an alkyl group" means a monovelent saturated linear, cyclic or branched aliphatic hydrocarbon group. Examples of "an alkyl group having 1 to 8 carbon atoms" include methyl group, ethyl group, n-propyl group, n-butyl group, n-pentyl group, n-hexyl group, isopropyl group, isobutyl group, s-butyl group, t-butyl group, isopentyl group, 2-methylbutyl group, neopentyl group, 1-ethylpropyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 1-ethylbutyl group, 2-ethylbutyl group, t-pentyl group, isohexyl group, cyclopropyl group, cyclobutyl group, cyclopentyl group, cyclohexyl group, cycloheptyl group, cyclopropylmethyl group, cyclobutylmethyl group, cyclopentylmethyl group, cyclohexylmethyl group, cycloheptylmethyl group and the like. Examples of "an alkyl group having 1 to 3 carbon atoms" include methyl group, ethyl group, n-propyl group, and isopropyl group.

In the present invention, the term "an alkoxy group having" means a monovelent saturated liner, cyclic or branched aliphatic hydrocarbon oxy group. Examples of "an alkoxy group having 1 to 8 carbon atoms" include methoxy group, ethoxy group, n-propoxy group, n-butoxy group, n-pentyloxy group, n-hexoxy group, isopropoxy group, isobutoxy group, s-butoxy group, t-butoxy group, isopentyloxy group, 2-methylbutoxy group, neopentyloxy group, cyclopropoxy group, cyclobutoxy group, cyclopentyloxy group, cyclohexyloxy group, cycloheptyloxy group, cyclopropylmethoxy group, cyclobutylmethoxy group, cyclopentylmethoxy group, cyclohexylmethoxy group and the like.

In the present invention, the term "an aryl group" means a monocyclic or bicyclic aromatic hydrocarbon group having 6 to 10 carbon atoms. Examples of the aryl group include phenyl group, naphthyl group, indenyl group, tetrahydronaphthyl group, indanyl group, azulenyl group and the like.

In the present invention, the term "a heteroaryl group" means a monocyclic or bicyclic aromatic heterocyclic group having 1 to 5 heteroatoms selected from oxygen atom, sulfer atom, and nitrogen atom. Examples of the heteroaryl group includespyridyl group, pyrazyl group, pyrimidyl group, furyl group, thienyl group, isoxazolyl group, isothiazolyl group, benzofuranyl group, benzothienyl group, benzothiazolyl group, benzoimidazolyl group, benzooxazolyl group, pyranyl group, imidazolyl group, oxazolyl group, thiazolyl group, triazinyl group, triazolyl group, benzoxazolyl group, benzoisoxazolyl group and the like.

In the present invention, the term "an optionally substituted alkyl group having 1 to 8 carbon atoms means an alkyl group having 1 to 8 carbon atoms which is optionally substituted with one or more substituents at substitutable positions. Examples of substituent of the alkyl group having 1 to 8 carbon atoms include alkoxy groups having 1 to 8 carbon atoms, halogen atoms and hydroxyl groups. When the number of the substituents is plural, the respective substituents may be the same or different.

In the present invention, the term "an optionally substituted aryl group" means an aryl group which is optionally substituted with one or more substituents at substitutable positions. Examples of substituent of the aryl group include an alkyl groups having 1 to 8 carbon atoms, alkoxy groups having 1 to 8 carbon atoms and halogen atoms. When the number of the substituents is plural, the respective substituents may be the same or different.

In the present invention, the term "an optionally substituted heteroaryl group" means a heteroaryl group which is optionally substituted with one or more substituents at substitutable positions. Examples of substituent of the heteroaryl group include an alkyl groups having 1 to 8 carbon atoms, alkoxy groups having 1 to 8 carbon atoms and halogen atoms. When the number of the substituents is plural, the respective substituents may be the same or different.

In the present invention, the term "a protective group of a carboxyl group" is, for example, a general protective group of a carboxyl group, which is described in PROTECTIVE GROUPS in ORGANIC SYNTHESIS, THIRD EDITION, H John Wiley & Sons, Inc. and examples of the protective group include methyl group, ethyl group, isopropyl group, heptyl group, t-butyl group, methoxymethyl group, methylthiomethyl group, methoxyethoxymethyl group, methoxyethyl group, benzyl group and the like.

In the present invention, the term "a protective group of a phenolic hydroxyl group" is, for example, a general protective group of a phenolic hydroxyl group, which is described in PROTECTIVE GROUPS in ORGANIC SYNTHESIS, THIRD EDITION, H John Wiley & Sons, Inc. and examples of the protective group include methyl group, isopropyl group, allyl group, t-butyl group, methoxymethyl group, methylthiomethyl group, methoxyethoxymethyl group, 1-ethoxyethyl group, benzyl group, 4-methoxybenzyl group, acetyl group, trimethylsilyl group, t-butyldimethylsilyl group and the like.

In the above formula (I), $R_1$ represents OR, NRR' which may form a ring or SR. Here, R and R' independently represent a hydrogen atom, an alkyl group having 1 to 8 carbon atoms optionally substituted with one or a plurality of alkoxy groups having 1 to 8 carbon atoms, halogen atoms or hydroxyl groups, an aryl group optionally substituted with one or a plurality of alkyl groups having 1 to 8 carbon atoms, alkoxy groups having 1 to 8 carbon atoms or halogen atoms, or a heteroaryl group optionally substituted with one or a plurality of alkyl groups having 1 to 8 carbon atoms, an alkoxy groups having 1 to 8 carbon atoms or a halogen atom. $R_1$ is preferably OR. When $R_1$ is OR or SR, R is preferably an alkyl group having 1 to 8 carbon atoms optionally substituted with one or a plurality of alkoxy groups having 1 to 8 carbon atoms, halogen atoms or hydroxyl groups, or an aryl group optionally substituted with one or a plurality of alkyl groups having 1 to 8 carbon atoms, alkoxy groups having 1 to 8 carbon atoms, halogen atoms. More preferably, R is an alkyl group having 1 to 8 carbon atoms optionally substituted with one or a plurality of alkoxy groups having 1 to 8 carbon atoms or hydroxyl groups. Particularly preferably, R is an isopropyl group, an isobutyl group or a neopentyl group. In NRR' in which $R_1$ may form a ring, the term "NRR' forms a ring" means that R and R' are bonded to form a saturated nitrogen-containing ring. In the case of NRR' in which $R_1$ may form a ring, preferably R and R' are independently an alkyl group having 1 to 8 carbon atoms optionally substituted with a hydroxyl group, and more preferably R and R' are independently a methyl group, an ethyl group or an isopropyl group, or R and R' are more preferably bonded to form together a pyrrolidin-1-yl group, a piperidin-1-yl group or a morpholin-1-yl group.

In the above formula (I), $R_2$ represents a hydrogen atom or an alkyl group having 1 to 8 carbon atoms. Specific examples of the term "an alkyl group having 1 to 8 carbon atoms" are the same as the definition described above. $R_2$ is preferably a hydrogen atom or an alkyl group having 1 to 3 carbon atoms and specific examples of the alkyl group include a methyl group, an ethyl group, an n-propyl group and an isopropyl group, more preferably a hydrogen atom or a methyl group, and particularly preferably a methyl group.

In the above formula (I), $X_1$, $X_2$ and $X_3$ are independently a $CR_3$ or a nitrogen atom, or $X_1$ is $CR_3$ or a nitrogen atom and $X_2$ and $X_3$ together form a benzene ring. $R_3$ represents a hydrogen atom or an alkyl group having 1 to 8 carbon atoms. If $X_1$ is $CR_3$ or a nitrogen atom and $X_2$ and $X_3$ together form a benzene ring, the compound may be represented by following structural formula:

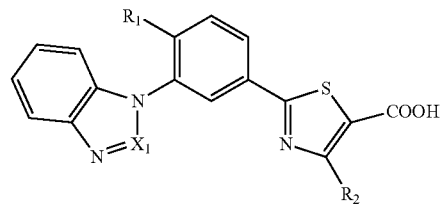

$X_1$, $X_2$ and $X_3$ are preferably independently $CR_3$ or a nitrogen atom. A more preferable combination is that $X_1$ is a nitrogen atom, $X_2$ is $CR_3$ or a nitrogen atom and $X_3$ is $CR_3$. In any of the combinations, $R_3$ is preferably a hydrogen atom. If $X_1$ is a nitrogen atom, $X_2$ is CH or a nitrogen atom and $X_3$ is CH, the compound may be represented by following structural formula:

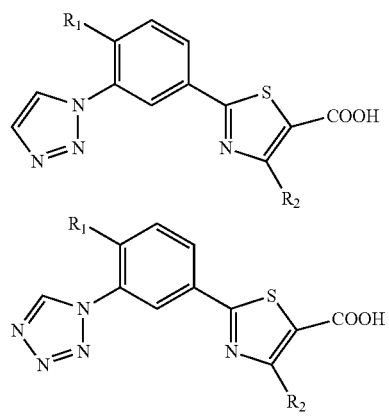

In the above formula (I), in any of the cases where $R_1$ is OR, NRR' which may form a ring or SR, a preferable combination of R, R', $R_2$, $X_1$, $X_2$ and $X_3$ is that preferable groups described above individually are combined, in which $R_3$ is a hydrogen group or an alkyl group having 1 to 8 carbon atoms. In the preferable combination of R, R', $R_2$, $X_1$, $X_2$ and $X_3$, $R_3$ is more preferably a hydrogen atom.

A more preferable combination of R, R', $R_2$, $X_1$, $X_2$ and $X_3$ is the one in which more preferable groups are combined, in which $R_3$ is a hydrogen atom or an alkyl group having 1 to 8 carbon atoms. In the more preferable combination of R, R', $R_2$, $X_1$, $X_2$ and $X_3$, $R_3$ is more preferably a hydrogen atom.

A further more preferable combination of R, R', $R_2$, $X_1$, $X_2$ and $X_3$ is that R is an isopropyl group, an isobutyl group or a neopentyl group, $R_2$ is a methyl group, $X_1$ is a nitrogen atom, $X_2$ is $CR_3$ or a nitrogen atom and $X_3$ is $CR_3$, in which $R_3$ is a hydrogen atom.

In any of combinations of a more preferable combination and a further more preferable combination of R, R', $R_2$, $X_1$, $X_2$ and $X_3$, $R_1$ is preferably OR.

Specific examples of the preferable combination of $R_1$, R, R', $R_2$, $X_1$, $X_2$ and $X_3$ in the formula (I) of the present invention include the following combinations 1) to 9):

1) $R_1$ is OR; R is an alkyl group having 1 to 8 carbon atoms optionally substituted with one or a plurality of alkoxy groups having 1 to 8 carbon atoms, halogen atoms or hydroxyl groups, or an aryl group optionally substituted with one or a plurality of alkyl groups having 1 to 8 carbon atoms, alkoxy groups having 1 to 8 carbon atoms or halogen atoms; $R_2$ is a hydrogen atom or an alkyl group having 1 to 3 carbon atoms; $X_1$ is a nitrogen atom; $X_2$ is $CR_3$ or a nitrogen atom; $X_3$ is $CR_3$; and $R_3$ is a hydrogen atom;

2) $R_1$ is OR; R is an alkyl group having 1 to 8 carbon atoms optionally substituted with one or a plurality of alkoxy groups having 1 to 8 carbon atoms or hydroxyl groups; $R_2$ is a hydrogen atom or an alkyl group having 1 to 3 carbon atoms; $X_1$ is a nitrogen atom; $X_2$ is $CR_3$ or a nitrogen atom; $X_3$ is $CR_3$; and $R_3$ is a hydrogen atom;

3) $R_1$ is OR; R is an isopropyl group, an isobutyl group or a neopentyl group; $R_2$ is a hydrogen atom or a methyl group; $X_1$ is a nitrogen atom; $X_2$ is $CR_3$ or a nitrogen atom; $X_3$ is $CR_3$; and $R_3$ is a hydrogen atom;

4) $R_1$ is SR; R is an alkyl group having 1 to 8 carbon atoms optionally substituted with one or a plurality of alkoxy groups having 1 to 8 carbon atoms, halogen atoms or hydroxyl groups, or an aryl group optionally substituted with one or a plurality of alkyl groups having 1 to 8 carbon atoms, alkoxy groups having 1 to 8 carbon atoms or halogen atoms; $R_2$ is a hydrogen atom or an alkyl group having 1 to 3 carbon atoms; $X_1$ is a nitrogen atom; $X_2$ is $CR_3$ or a nitrogen atom; $X_3$ is $CR_3$; and $R_3$ is a hydrogen atom;

5) $R_1$ is SR; R is an alkyl group having 1 to 8 carbon atoms optionally substituted with one or a plurality of alkoxy groups having 1 to 8 carbon atoms or hydroxyl groups; $R_2$ is a hydrogen atom or an alkyl group having 1 to 3 carbon atoms; $X_1$ is a nitrogen atom; $X_2$ is $CR_3$ or a nitrogen atom; $X_3$ is $CR_3$; and $R_3$ is a hydrogen atom;

6) $R_1$ is SR; R is an isopropyl group, an isobutyl group or a neopentyl group; $R_2$ is a hydrogen atom or a methyl group; $X_1$ is a nitrogen atom; $X_2$ is $CR_3$ or a nitrogen atom; $X_3$ is $CR_3$; and $R_3$ is a hydrogen atom;

7) $R_1$ is NRR' which may form a ring; R and R' are independently an alkyl group having 1 to 8 carbon atoms optionally substituted with one or a plurality of alkoxy groups having 1 to 8 carbon atoms or hydroxyl groups; $R_2$ is a hydrogen atom or an alkyl group having 1 to 3 carbon atoms; $X_1$ is a nitrogen atom; $X_2$ is $CR_3$ or a nitrogen atom; $X_3$ is $CR_3$; and $R_3$ is a hydrogen atom;

8) $R_1$ is NRR' which may form a ring; R and R' are independently a methyl group, an ethyl group or an isopropyl group or R and R' are bonded to form together a pyrrolidin-1-yl group, a piperidin-1l-yl group or a morpholin-1-yl group; $R_2$ is a hydrogen atom or an alkyl group having 1 to 3 carbon atoms; $X_1$ is a nitrogen atom; $X_2$ is $CR_3$ or a nitrogen atom; $X_3$ is $CR_3$; and $R_3$ is a hydrogen atom;

9) $R_1$ is NRR' which may form a ring; R and R' are independently a methyl group, an ethyl group or an isopropyl group or R and R' are bonded to form together a pyrrolidin-1-yl group, a piperidin-1-yl group or a morpholin-1-yl group; $R_2$ is a hydrogen atom or a methyl group; $X_1$ is a nitrogen atom; $X_2$ is a $CR_3$ or a nitrogen atom; $X_3$ is $CR_3$; and $R_3$ is a hydrogen atom.

A compound of the present invention is a compound exhibiting an excellent xanthine oxidase inhibitory activity. In addition, a compound of the present invention has an excellent uric acid lowering effect. Further, a compound of the present invention has a sustained uric acid lowering effect over a long period of time.

Examples of a preferred compound include the following compounds.

| Compound No. | Structure | Name |
|---|---|---|
| 1 | 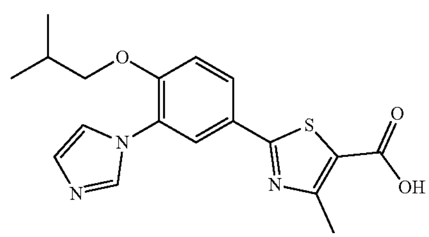 [SMILES: Cc1nc(-c2ccc(OCC(C)C)c(-n3ccnc3)c2)sc1C(=O)O] | 2-[3-(1H-imidazol-1-yl)-4-(2-methylpropoxy)phenyl]-4-methyl-1,3-thiazole-5-carboxylic acid |
| 2 | 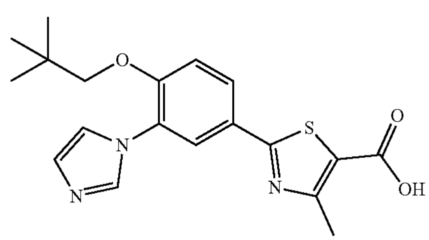 [SMILES: Cc1nc(-c2ccc(OCC(C)(C)C)c(-n3ccnc3)c2)sc1C(=O)O] | 2-[4-(2,2-dimethylpropoxy)-3-(1H-imidazol-1-yl)phenyl]-4-methyl-1,3-thiazole-5-carboxylic acid |
| 3 | 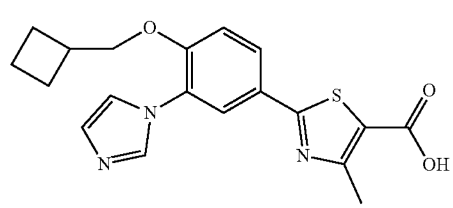 [SMILES: Cc1nc(-c2ccc(OCC3CCC3)c(-n3ccnc3)c2)sc1C(=O)O] | 2-[4-(cyclobutylmethoxy)-3-(1H-imidazol-1-yl)phenyl]-4-methyl-1,3-thiazole-5-carboxylic acid |

-continued

| Compound No. | Structure | Name |
|---|---|---|
| 4 | 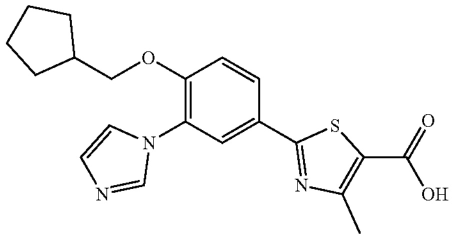 [SMILES: Cc1nc(-c2ccc(OCC3CCCC3)c(-n3ccnc3)c2)sc1C(=O)O] | 2-[4-(cyclopentylmethoxy)-3-(1H-imidazol-1-yl)phenyl]-4-methyl-1,3-thiazole-5-carboxylic acid |
| 5 | 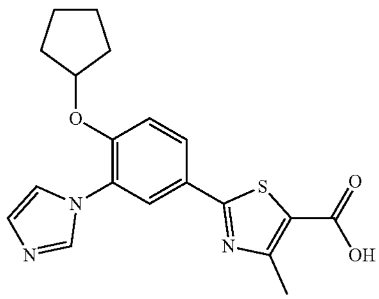 [SMILES: Cc1nc(-c2ccc(OC3CCCC3)c(-n3ccnc3)c2)sc1C(=O)O] | 2-[4-(cyclopentyloxy)-3-(1H-imidazol-1-yl)phenyl]-4-methyl-1,3-thiazole-5-carboxylic acid |
| 6 | 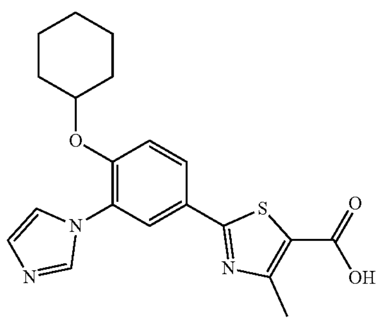 [SMILES: Cc1nc(-c2ccc(OC3CCCCC3)c(-n3ccnc3)c2)sc1C(=O)O] | 2-[4-(cyclohexyloxy)-3-(1H-imidazol-1-yl)phenyl]-4-methyl-1,3-thiazole-5-carboxylic acid |
| 7 | 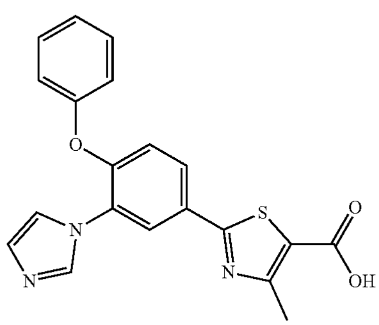 [SMILES: Cc1nc(-c2ccc(Oc3ccccc3)c(-n3ccnc3)c2)sc1C(=O)O] | 2-[3-(1H-imidazol-1-yl)-4-phenoxyphenyl]-4-methyl-1,3-thiazole-5-carboxylic acid |
| 8 | 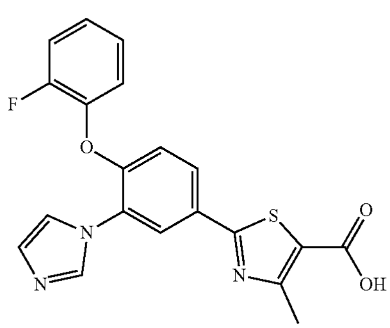 [SMILES: Cc1nc(-c2ccc(Oc3ccccc3F)c(-n3ccnc3)c2)sc1C(=O)O] | 2-[4-(2-fluorophenoxy)-3-(1H-imidazol-1-yl)phenyl]-4-methyl-1,3-thiazole-5-carboxylic acid |

-continued

| Compound No. | Structure | Name |
|---|---|---|
| 9 | 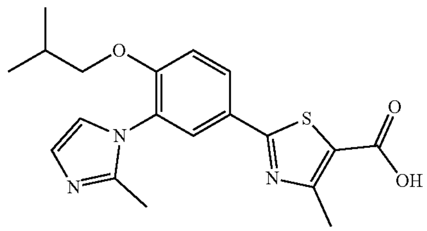 [SMILES: Cc1nc(-c2ccc(OCC(C)C)c(-n3ccnc3C)c2)sc1C(=O)O] | 4-methyl-2-[3-(2-methyl-1H-imidazol-1-yl)-4-(2-methylpropoxy)phenyl]-1,3-thiazole-5-carboxylic acid |
| 10 | 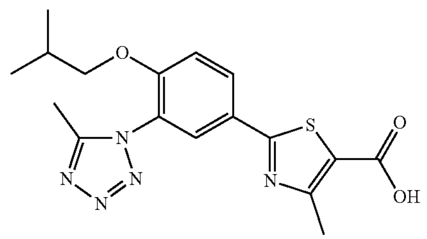 [SMILES: Cc1nc(-c2ccc(OCC(C)C)c(-n3nnnc3C)c2)sc1C(=O)O] | 4-methyl-2-[3-(5-methyl-1H-1,2,3,4-tetrazol-1-yl)-4-(2-methylpropoxy)phenyl]-1,3-thiazole-5-carboxylic acid |
| 11 | 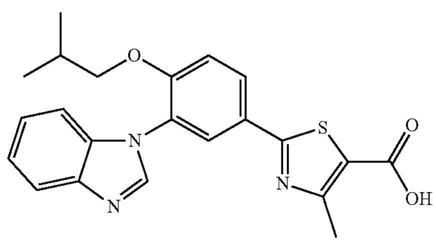 [SMILES: Cc1nc(-c2ccc(OCC(C)C)c(-n3cnc4ccccc43)c2)sc1C(=O)O] | 2-[3-(1H-1,3-benzodiazol-1-yl)-4-(2-methylpropoxy)phenyl]-4-methyl-1,3-thiazole-5-carboxylic acid |
| 12 | 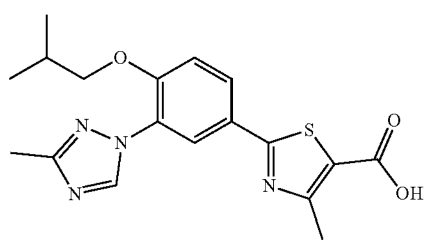 [SMILES: Cc1ncn(-c2cc(-c3nc(C)c(C(=O)O)s3)ccc2OCC(C)C)n1] | 4-methyl-2-[3-(3-methyl-1H-1,2,4-triazol-1-yl)-4-(2-methylpropoxy)phenyl]-1,3-thiazole-5-carboxylic acid |
| 13 | 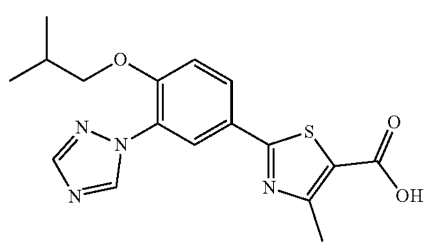 [SMILES: Cc1nc(-c2ccc(OCC(C)C)c(-n3cncn3)c2)sc1C(=O)O] | 4-methyl-2-[4-(2-methylpropoxy)-3-(1H-1,2,4-triazol-1-yl)phenyl]-1,3-thiazole-5-carboxylic acid |
| 14 | 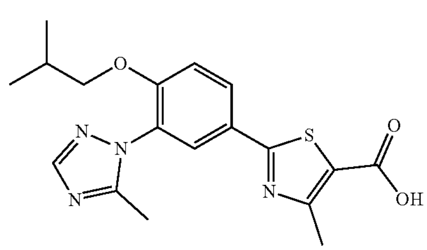 [SMILES: Cc1nc(-c2ccc(OCC(C)C)c(-n3ncnc3C)c2)sc1C(=O)O] | 4-methyl-2-[3-(5-methyl-1H-1,2,4-triazol-1-yl)-4-(2-methylpropoxy)phenyl]-1,3-thiazole-5-carboxylic acid |

-continued

| Compound No. | Structure | Name |
|---|---|---|
| 15 | 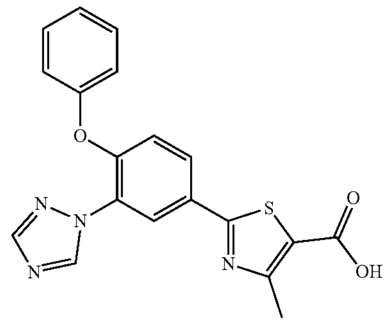 [SMILES: Cc1nc(-c2ccc(Oc3ccccc3)c(-n3cncn3)c2)sc1C(=O)O] | 4-methyl-2-[4-phenoxy-3-(1H-1,2,4-triazol-1-yl)phenyl]-1,3-thiazole-5-carboxylic acid |
| 16 | 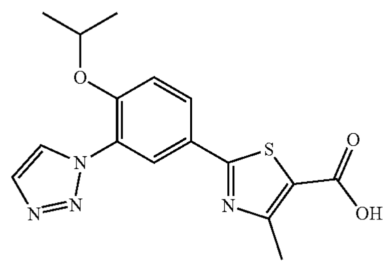 [SMILES: Cc1nc(-c2ccc(OC(C)C)c(-n3ccnn3)c2)sc1C(=O)O] | 4-methyl-2-[4-(propan-2-yloxy)-3-(1H-1,2,3-triazol-1-yl)phenyl]-1,3-thiazole-5-carboxylic acid |
| 17 | 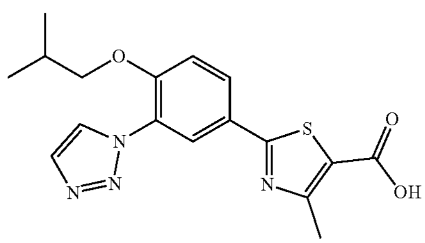 [SMILES: Cc1nc(-c2ccc(OCC(C)C)c(-n3ccnn3)c2)sc1C(=O)O] | 4-methyl-2-[4-(2-methylpropoxy)-3-(1H-1,2,3-triazol-1-yl)phenyl]-1,3-thiazole-5-carboxylic acid |
| 18 | 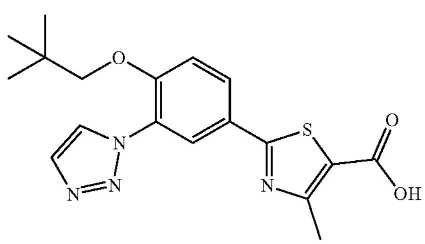 [SMILES: Cc1nc(-c2ccc(OCC(C)(C)C)c(-n3ccnn3)c2)sc1C(=O)O] | 2-[4-(2,2-dimethylpropoxy)-3-(1H-1,2,3-triazol-1-yl)phenyl]-4-methyl-1,3-thiazole-5-carboxylic acid |
| 19 | 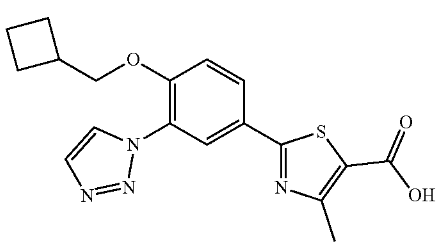 [SMILES: Cc1nc(-c2ccc(OCC3CCC3)c(-n3ccnn3)c2)sc1C(=O)O] | 2-[4-(cyclobutylmethoxy)-3-(1H-1,2,3-triazol-1-yl)phenyl]-4-methyl-1,3-thiazole-5-carboxylic acid |
| 20 | 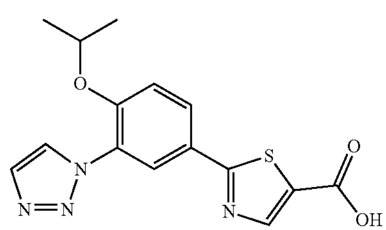 [SMILES: CC(C)Oc1ccc(-c2ncc(C(=O)O)s2)cc1-n1ccnn1] | 2-[4-(propan-2-yloxy)-3-(1H-1,2,3-triazol-1-yl)phenyl]-1,3-thiazole-5-carboxylic acid |

-continued

| Compound No. | Structure | Name |
|---|---|---|
| 21 | 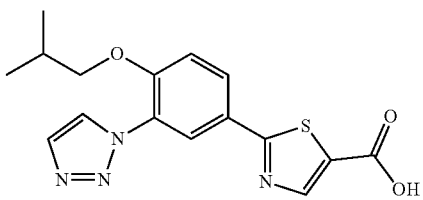 [SMILES: CC(C)COc1ccc(-c2ncc(C(=O)O)s2)cc1-n1ccnn1] | 2-[4-(2-methylpropoxy)-3-(1H-1,2,3-triazol-1-yl)phenyl]-1,3-thiazole-5-carboxylic acid |
| 22 | 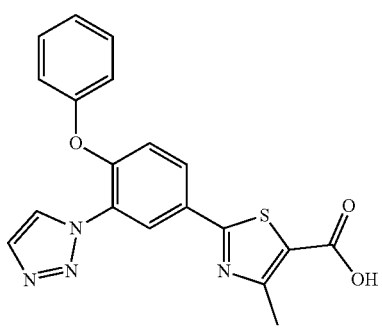 [SMILES: Cc1nc(-c2ccc(Oc3ccccc3)c(-n3ccnn3)c2)sc1C(=O)O] | 4-methyl-2-[4-phenoxy-3-(1H-1,2,3-triazol-1-yl)phenyl]-1,3-thiazole-5-carboxylic acid |
| 23 | 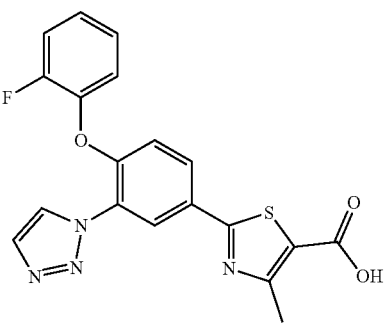 [SMILES: Cc1nc(-c2ccc(Oc3ccccc3F)c(-n3ccnn3)c2)sc1C(=O)O] | 2-[4-(2-fluorophenoxy)-3-(1H-1,2,3-triazol-1-yl)phenyl]-4-methyl-1,3-thiazole-5-carboxylic acid |
| 24 | 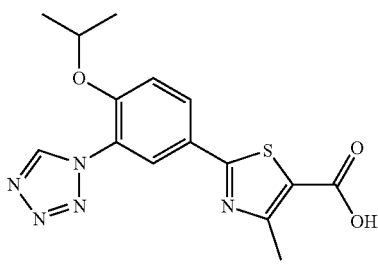 [SMILES: Cc1nc(-c2ccc(OC(C)C)c(-n3cnnn3)c2)sc1C(=O)O] | 4-methyl-2-[4-(propan-2-yloxy)-3-(1H-1,2,3,4-tetraazole-1-yl)phenyl]-1,3-thiazole-5-carboxylic acid |
| 25 | 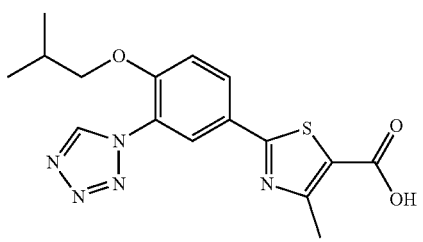 [SMILES: Cc1nc(-c2ccc(OCC(C)C)c(-n3cnnn3)c2)sc1C(=O)O] | 4-methyl-2-[4-(2-methylpropoxy)-3-(1H-1,2,3,4-tetrazol-1-yl)phenyl]-1,3-thiazole-5-carboxylic acid |

-continued

| Compound No. | Structure | Name |
|---|---|---|
| 26 | 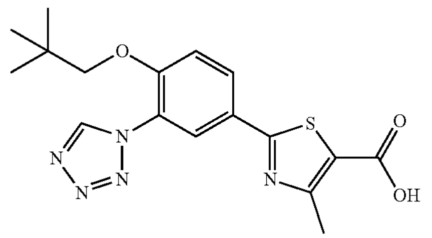 [SMILES: Cc1nc(-c2ccc(OCC(C)(C)C)c(-n3cnnn3)c2)sc1C(=O)O] | 2-[4-(2,2-dimethylpropoxy)-3-(1H-1,2,3,4-tetrazol-1-yl)phenyl]-4-methyl-1,3-thiazole-5-carboxylic acid |
| 27 | 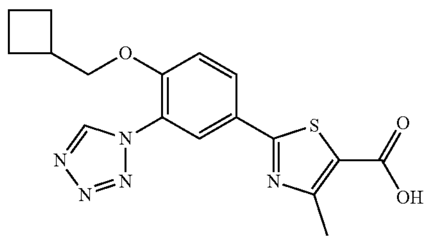 [SMILES: Cc1nc(-c2ccc(OCC3CCC3)c(-n3cnnn3)c2)sc1C(=O)O] | 2-[4-(cyclobutylmethoxy)-3-(1H-1,2,3,4-tetrazol-1-yl)phenyl]-4-methyl-1,3-thiazole-5-carboxylic acid |
| 28 | 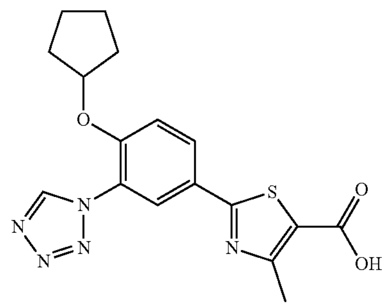 [SMILES: Cc1nc(-c2ccc(OC3CCCC3)c(-n3cnnn3)c2)sc1C(=O)O] | 2-[4-(cyclopentyloxy)-3-(1H-1,2,3,4-tetrazol-1-yl)phenyl]-4-methyl-1,3-thiazole-5-carboxylic acid |
| 29 | 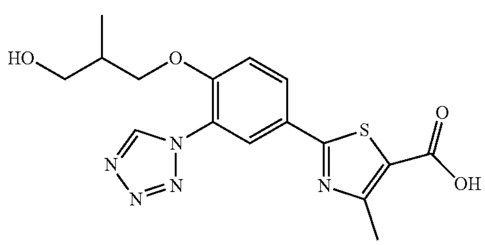 [SMILES: Cc1nc(-c2ccc(OCC(C)CO)c(-n3cnnn3)c2)sc1C(=O)O] | 2-[4-(3-hydroxy-2-methylpropoxy)-3-(1H-1,2,3,4-tetrazol-1-yl)phenyl]-4-methyl-1,3-thiazole-5-carboxylic acid |
| 30 | 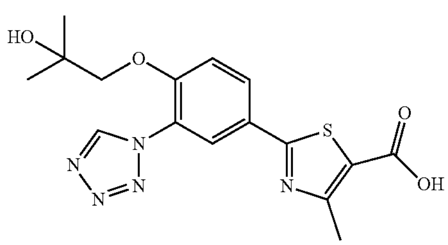 [SMILES: Cc1nc(-c2ccc(OCC(C)(C)O)c(-n3cnnn3)c2)sc1C(=O)O] | 2-[4-(2-hydroxy-2-methylpropoxy)-3-(1H-1,2,3,4-tetrazol-1-yl)phenyl]-4-methyl-1,3-thiazole-5-carboxylic acid |
| 31 | 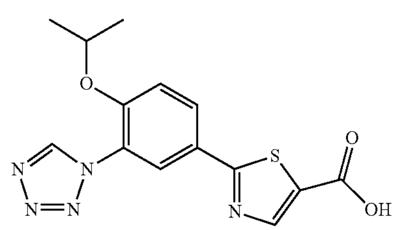 [SMILES: CC(C)Oc1ccc(-c2ncc(C(=O)O)s2)cc1-n1cnnn1] | 2-[4-(propan-2-yloxy)-3-(1H-1,2,3,4-tetrazol-1-yl)phenyl]-1,3-thiazole-5-carboxylic acid |

| Compound No. | Structure | Name |
|---|---|---|
| 32 | 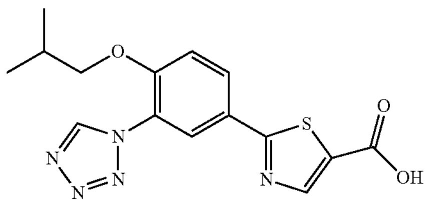 [SMILES: CC(C)COc1ccc(-c2ncc(C(=O)O)s2)cc1-n1cnnn1] | 2-[4-(2-methylpropoxy)-3-(1H-1,2,3,4-tetrazol-1-yl)phenyl]-1,3-thiazole-5-carboxylic acid |
| 33 | 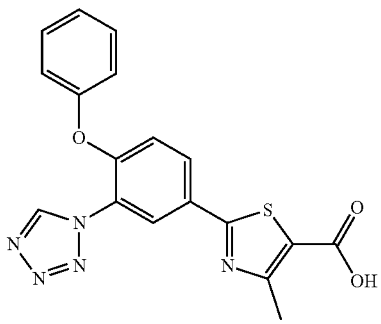 [SMILES: Cc1nc(-c2ccc(Oc3ccccc3)c(-n3cnnn3)c2)sc1C(=O)O] | 4-methyl-2-[4-phenoxy-3-(1H-1,2,3,4-tetrazol-1-yl)phenyl]-1,3-thiazole-5-carboxylic acid |
| 34 | 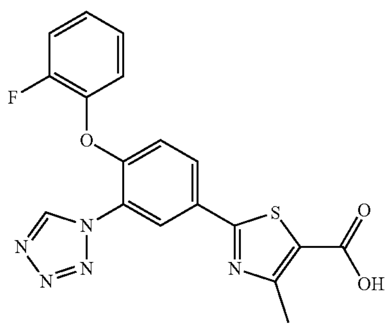 [SMILES: Cc1nc(-c2ccc(Oc3ccccc3F)c(-n3cnnn3)c2)sc1C(=O)O] | 2-[4-(2-fluorophenoxy)-3-(1H-1,2,3,4-tetrazol-1-yl)phenyl]-4-methyl-1,3-thiazole-5-carboxylic acid |
| 35 | 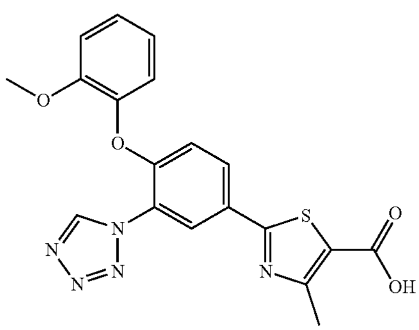 [SMILES: COc1ccccc1Oc1ccc(-c2nc(C)c(C(=O)O)s2)cc1-n1cnnn1] | 2-[4-(2-methoxyphenoxy)-3-(1H-1,2,3,4-tetrazol-1-yl)phenyl]-4-methyl-1,3-thiazole-5-carboxylic acid |
| 36 | 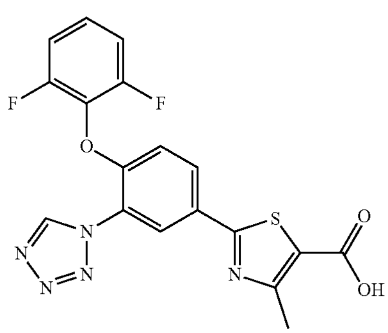 [SMILES: Cc1nc(-c2ccc(Oc3c(F)cccc3F)c(-n3cnnn3)c2)sc1C(=O)O] | 2-[4-(2,6-difluorophenoxy)-3-(1H-1,2,3,4-tetrazol-1-yl)phenyl]-4-methyl-1,3-thiazole-5-carboxylic acid |

-continued

| Compound No. | Structure | Name |
|---|---|---|
| 37 | 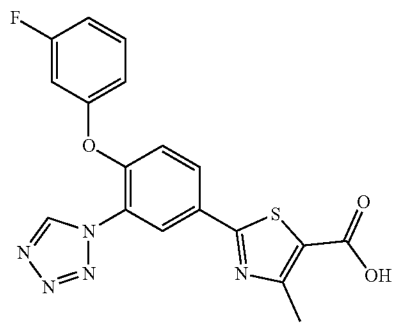 [SMILES: Cc1nc(-c2ccc(Oc3cccc(F)c3)c(-n3cnnn3)c2)sc1C(=O)O] | 2-[4-(3-fluorophenoxy)-3-(1H-1,2,3,4-tetrazol-1-yl)phenyl]-4-methyl-1,3-thiazole-5-carboxylic acid |
| 38 | 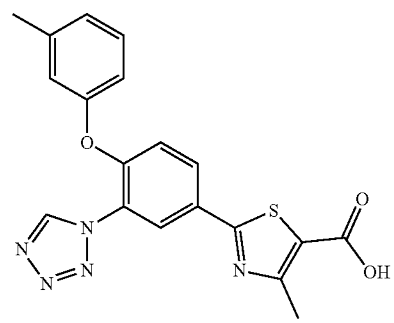 [SMILES: Cc1cccc(Oc2ccc(-c3nc(C)c(C(=O)O)s3)cc2-n2cnnn2)c1] | 2-[4-(3-methylphenoxy)-3-(1H-1,2,3,4-tetrazol-1-yl)phenyl]-4-methyl-1,3-thiazole-5-carboxylic acid |
| 39 | 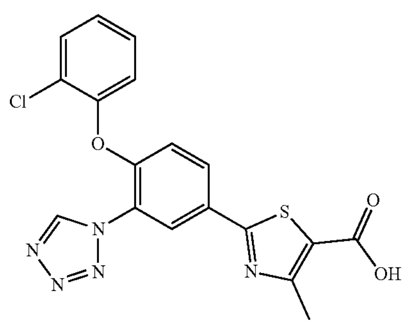 [SMILES: Cc1nc(-c2ccc(Oc3ccccc3Cl)c(-n3cnnn3)c2)sc1C(=O)O] | 2-[4-(2-chlorophenoxy)-3-(1H-1,2,3,4-tetrazol-1-yl)phenyl]-4-methyl-1,3-thiazole-5-carboxylic acid |
| 40 | 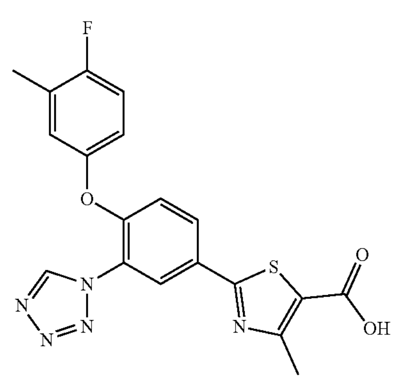 [SMILES: Cc1cc(Oc2ccc(-c3nc(C)c(C(=O)O)s3)cc2-n2cnnn2)ccc1F] | 2-[4-(4-fluoro-3-methylphenoxy)-3-(1H-1,2,3,4-tetrazol-1-yl)phenyl]-4-methyl-1,3-thiazole-5-carboxylic acid |

-continued

| Compound No. | Structure | Name |
|---|---|---|
| 41 | 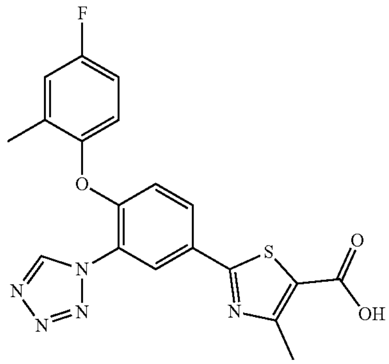 [SMILES: Cc1cc(F)ccc1Oc1ccc(-c2nc(C)c(C(=O)O)s2)cc1-n1cnnn1] | 2-[4-(4-fluoro-2-methylphenoxy)-3-(1H-1,2,3,4-tetrazol-1-yl)phenyl]-4-methyl-1,3-thiazole-5-carboxylic acid |
| 42 | 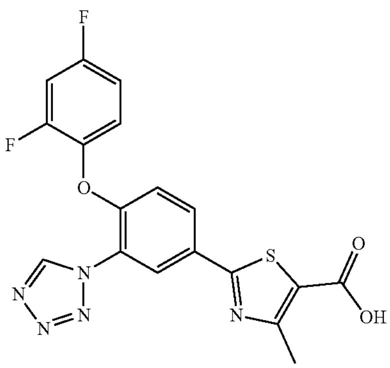 [SMILES: Cc1nc(-c2ccc(Oc3ccc(F)cc3F)c(-n3cnnn3)c2)sc1C(=O)O] | 2-[4-(2,4-difluorophenoxy)-3-(1H-1,2,3,4-tetrazol-1-yl)phenyl]-4-methyl-1,3-thiazole-5-carboxylic acid |
| 43 | 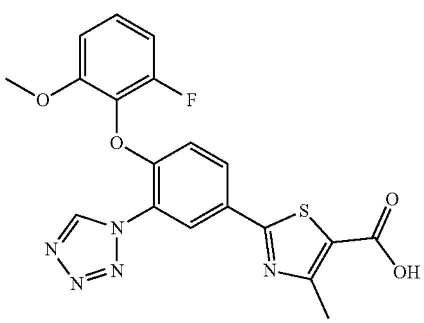 [SMILES: COc1cccc(F)c1Oc1ccc(-c2nc(C)c(C(=O)O)s2)cc1-n1cnnn1] | 2-[4-(2-fluoro-6-methoxyphenoxy)-3-(1H-1,2,3,4-tetrazol-1-yl)phenyl]-4-methyl-1,3-thiazole-5-carboxylic acid |
| 44 | 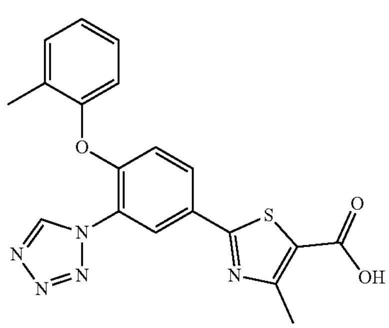 [SMILES: Cc1ccccc1Oc1ccc(-c2nc(C)c(C(=O)O)s2)cc1-n1cnnn1] | 2-[4-(2-methylphenoxy)-3-(1H-1,2,3,4-tetrazol-1-yl)phenyl]-4-methyl-1,3-thiazole-5-carboxylic acid |

-continued

| Compound No. | Structure | Name |
|---|---|---|
| 45 | 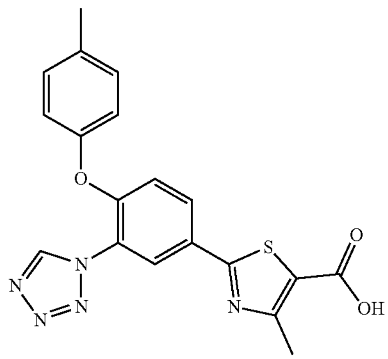 [SMILES: Cc1ccc(Oc2ccc(-c3nc(C)c(C(=O)O)s3)cc2-n2cnnn2)cc1] | 2-[4-(4-methylphenoxy)-3-(1H-1,2,3,4-tetrazol-1-yl)phenyl]-4-methyl-1,3-thiazole-5-carboxylic acid |
| 46 | 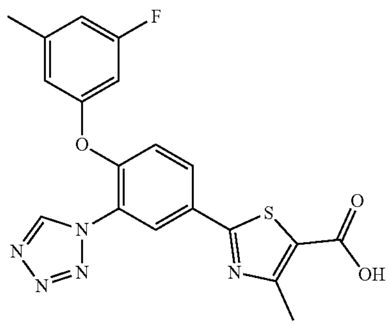 [SMILES: Cc1cc(F)cc(Oc2ccc(-c3nc(C)c(C(=O)O)s3)cc2-n2cnnn2)c1] | 2-[4-(3-fluoro-5-methylphenoxy)-3-(1H-1,2,3,4-tetrazol-1-yl)phenyl]-4-methyl-1,3-thiazole-5-carboxylic acid |
| 47 | 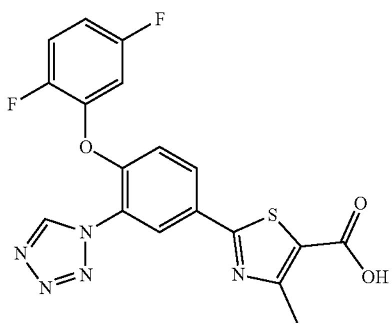 [SMILES: Cc1nc(-c2ccc(Oc3cc(F)ccc3F)c(-n3cnnn3)c2)sc1C(=O)O] | 2-[4-(2,5-difluorophenoxy)-3-(1H-1,2,3,4-tetrazol-1-yl)phenyl]-4-methyl-1,3-thiazole-5-carboxylic acid |
| 48 | 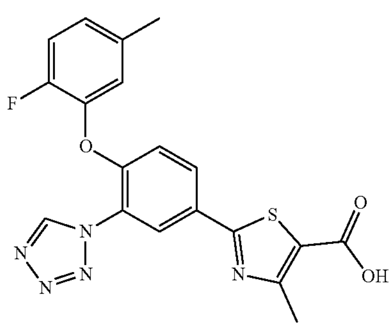 [SMILES: Cc1ccc(F)c(Oc2ccc(-c3nc(C)c(C(=O)O)s3)cc2-n2cnnn2)c1] | 2-[4-(2-fluoro-5-methylphenoxy)-3-(1H-1,2,3,4-tetrazol-1-yl)phenyl]-4-methyl-1,3-thiazole-5-carboxylic acid |
| 49 | 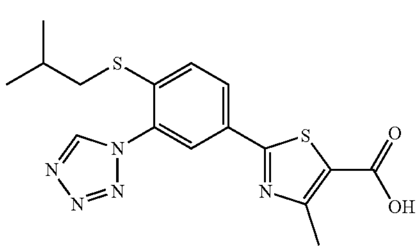 [SMILES: Cc1nc(-c2ccc(SCC(C)C)c(-n3cnnn3)c2)sc1C(=O)O] | 4-methyl-2-{4-[(2-methylpropyl)sulfanyl]-3-(1H-1,2,3,4-tetrazol-1-yl)phenyl}-1,3-thiazole-5-carboxylic acid |

-continued

| Compound No. | Structure | Name |
|---|---|---|
| 50 | 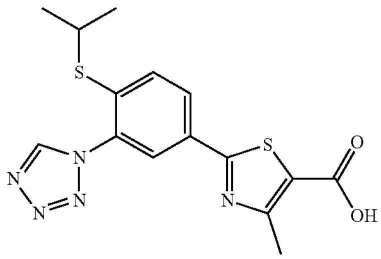 [SMILES: Cc1nc(-c2ccc(SC(C)C)c(-n3cnnn3)c2)sc1C(=O)O] | 4-methyl-2-[4-(propan-2-ylsulfanyl)-3-(1H-1,2,3,4-tetrazol-1-yl)phenyl]-1,3-thiazole-5-carboxylic acid |
| 51 | 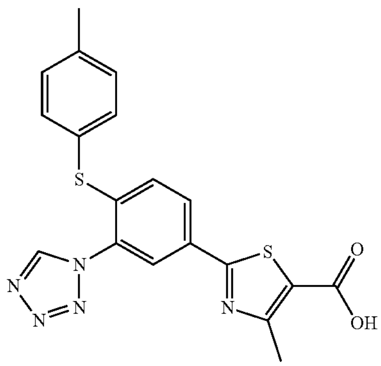 [SMILES: Cc1ccc(Sc2ccc(-c3nc(C)c(C(=O)O)s3)cc2-n2cnnn2)cc1] | 4-methyl-2-{4-[(4-methylphenyl)sulfanyl]-3-(1H-1,2,3,4-tetrazol-1-yl)phenyl}-1,3-thiazole 5-carboxylic acid |
| 52 | 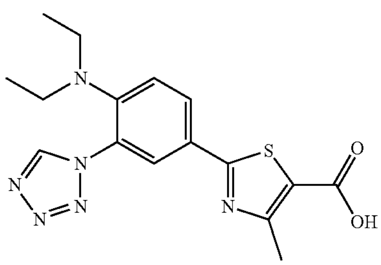 [SMILES: CCN(CC)c1ccc(-c2nc(C)c(C(=O)O)s2)cc1-n1cnnn1] | 2-[4-(N,N-diethylamino)-3-(1H-1,2,3,4-tetrazol-1-yl)phenyl]-4-methyl-1,3-thiazole-5-carboxylic acid |
| 53 | 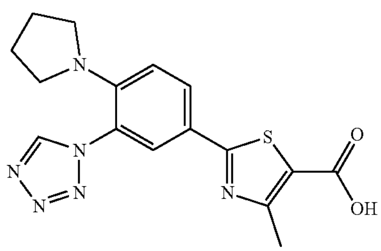 [SMILES: Cc1nc(-c2ccc(N3CCCC3)c(-n3cnnn3)c2)sc1C(=O)O] | 4-methyl-2-[4-(pyrrolidin-1-yl)-3-(1H-1,2,3,4-tetrazol-1-yl)phenyl]-1,3-thiazole 5-carboxylic acid |

Among these compounds, preferred compounds are compounds Nos. 1, 2, 3, 4, 5, 6, 9, 10, 11, 12, 13, 14, 16, 17, 18, 19, 20, 21, 24, 25, 26, 27, 28, 29, 30, 31, 32, 33, 34, 35, 36, 37, 38, 39, 40, 41, 42, 43, 44, 45, 46, 47, 48, 49, 50, 51, 52 and 53, more preferred compounds are compound Nos. 1, 9, 11, 12, 13, 14, 16, 17, 18, 19, 20, 21, 24, 25, 26, 27, 28, 29, 30, 31, 32, 33, 34, 35, 36, 37, 38, 39, 40, 41, 42, 43, 44, 45, 46, 47, 48, 49, 50, 51, 52 and 53, and particularly preferred compounds are compounds Nos 17, 24, 25 and 26.

In the compounds represented by the formula (II), which may be used as the manufacturing intermediates of the compounds represented by the formula (I) of the present invention, R1, R, R', R2, X1, X2, X3 and CR3 are the same as the definition in the formula (I). R4 represents a protective group of a carboxyl group. The definition of the protective group of a carboxyl group is as described above and preferably is a methyl group, an ethyl group or a benzyl group.

<General Synthesis Methods>

The compounds of the formula (I) thereof may be synthesized, for example, according to any of the synthesis methods described below. In addition, in each of the formulas, $R_1$, R, R', $R_2$, $X_1$, $X_2$ and $X_3$ are the same as defined in the formula (I). Further, the reagents or solvents or the like as the conditions described in the chemical formulas are only exemplified as described in the text. Each of the substituents may be protected by a suitable protective group or may be deprotected in a suitable stage, where necessary. In addition, as a suitable protective group and a method for removing the protective group, a protective group of each substituent widely used in this field and a well-known method may be employed and are described, for example, in PROTECTIVE GROUPS in ORGANIC SYNTHESIS, THIRD EDITION, John Wiley & Sons, Inc.

Synthesis of Compound (A-2)

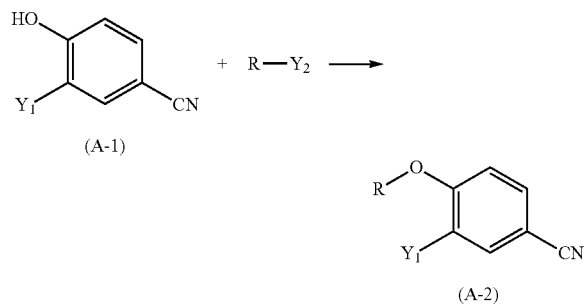

(wherein $Y_1$ and $Y_2$ represent a leaving group.) Examples of a leaving group represented by $Y_1$ and $Y_2$ include a halogen atom, a methanesulfonyloxy group, a p-toluenesulfonyloxy group, a trifluoromethanesulfonyloxy group and the like. The reaction is a method for synthesizing a compound (A-2) by reacting a phenolic hydroxyl group in the compound (A-1) with an alkylating reagent having a leaving group under the presence of a base. Examples of the base to be used include an inorganic salt such as sodium hydride, sodium hydroxide, potassium hydroxide, lithium hydroxide, sodium carbonate, potassium carbonate and cesium carbonate, a metal alkoxide such as sodium ethoxide, sodium methoxide and potassium t-butoxide and an organic amine such as triethylamine, pyridine, 4-aminopyridine, N-ethyl-N,N-diisopropylamine (DIPEA) and 1,8-diazabicyclo[5.4.0]-7-undecene (DBU). The reaction is performed by reacting the compound (A-1) with an equivalent or slightly excessive amount of a base in a solvent inactive to the reaction at 0° C. to 140° C., followed by adding an equivalent amount or an excessive amount of an alkylating reagent to allow the reaction to proceed generally for 0.5 to 16 hours. The reaction is preferably performed under an inert gas atmosphere such as nitrogen. Here, the solvent includes, though not particularly limited, for example: ethers such as diethyl ether, tetrahydrofuran (THF), 1,4-dioxane, 1,2-dimethoxy ethane and 1,2-diethoxy ethane; N,N-dimethylformamide (DMF); N-methylpyrrolidone; dimethyl sulfoxide (DMSO); water; or a mixed solvent thereof.

In addition, the compound (A-2) may be synthesized, for example, according to the synthesis method described below.

Synthesis of Compound (A-2)

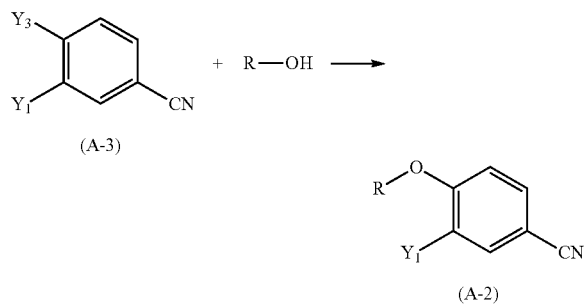

(wherein $Y_1$ and $Y_3$ represent a leaving group.) Examples of a leaving group represented by $Y_1$ and $Y_3$ include a halogen atom, a methanesulfonyloxy group, a p-toluenesulfonyloxy group and a trifluoromethanesulfonyloxy group. The reaction is a method for synthesizing a compound (A-2) by converting alcohols to lithium alkoxide, sodium alkoxide or potassium alkoxide with a base, followed by the reaction with a compound (A-3). Examples of the base to be used include an inorganic salt such as sodium hydride, sodium hydroxide, potassium hydroxide, lithium hydroxide, sodium carbonate, potassium carbonate and cesium carbonate, a metal alkoxide such as sodium ethoxide, sodium methoxide and potassium t-butoxide, and an organic amine such as triethylamine, pyridine, 4-aminopyridine, N-ethyl-N,N-diisopropylamine (DIPEA) and 1,8-diazabicyclo[5.4.0]-7-undecene (DBU). The reaction is performed by reacting an equivalent or excessive amount of alcohols with an equivalent or slightly excessive amount of a base at −20° C. to 120° C. in a solvent inactive to the reaction, followed by adding the compound (A-3) to allow the reaction to proceed generally for 0.5 to 16 hours. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; N,N-dimethylformamide (DMF), N-methylpyrrolidone; dimethyl sulfoxide (DMSO); or a mixed solvent thereof.

Synthesis of Compound (A-5)

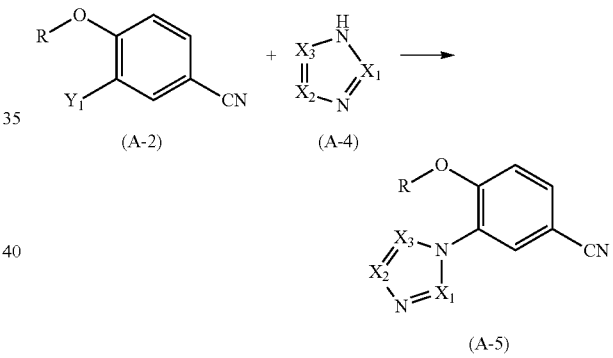

(wherein $Y_1$ represents a leaving group.) The reaction is a method for synthesizing a compound (A-5) by a substitution reaction between the compounds (A-2) and (A-4). Examples of a leaving group represented by $Y_1$ include a halogen atom, a methanesulfonyloxy group, a p-toluenesulfonyloxy group and a trifluoromethanesulfonyloxy group. The reaction is performed by reacting the compounds (A-2) and (A-4) in an equivalent amount or using an excessive amount of one of the compounds under the presence of a base in a solvent inactive to the reaction at room temperature to a reflux temperature under heating for generally 0.5 hours to 2 days. The reaction is preferably performed under an inert gas atmosphere such as nitrogen. Examples of the base to be used include an inorganic salt such as sodium hydride, sodium hydroxide, potassium hydroxide, lithium hydroxide, sodium carbonate, potassium carbonate and cesium carbonate, a metal alkoxide such as sodium ethoxide and sodium methoxide and an organic amine such as triethylamine, pyridine, 4-aminopyridine, N-ethyl-N,N-diisopropylamine (DIPEA) and 1,8-diazabicyclo[5.4.0]-undecene (DBU). Here, the solvent includes, though not particularly limited, for example: aromatic hydrocarbons such as benzene, tolu-

Synthesis of Compound (A-6)

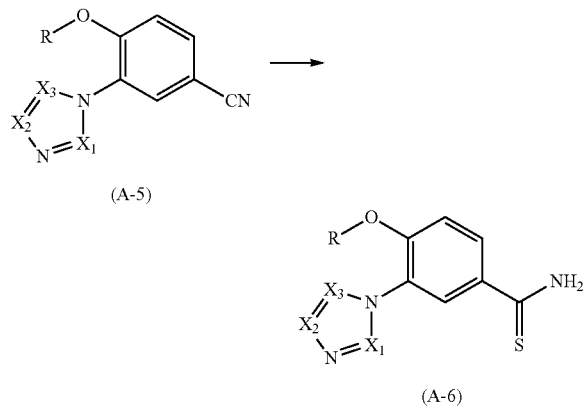

(A-5)

(A-6)

The reaction is a conversion reaction from a cyano group to a thioamide group and is performed by reacting an aromatic cyano group derivative represented by the above formula (A-5) with a sulfur source under acidic conditions. The reaction is performed by using the compound (A-5) and the sulfur source in an equivalent amount or using an excessive amount of one of the compounds under the presence of an acid in a solvent inactive to the reaction at room temperature to a reflux temperature under heating for generally 0.5 hours to 2 days. The reaction is preferably performed under an inert gas atmosphere such as nitrogen. Examples of the sulfur source to be used include hydrogen sulfide, thioacetamide or thioacetic acid. Examples of the acid to be used include inorganic acid such as hydrochloric acid, sulfuric acid and organic acid such as acetic acid, or an aqueous solution of these acids. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; N,N-dimethylformamide (DMF); N-methylpyrrolidone; dimethyl sulfoxide (DMSO); or a mixed solvent thereof.

Synthesis of Compound (A-8)

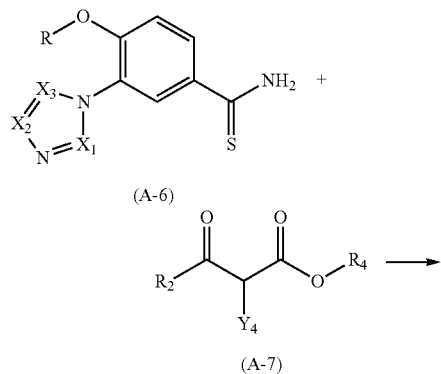

(A-6)

(A-7)

-continued

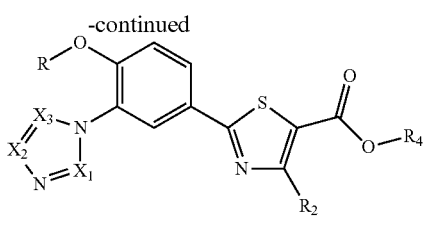

(A-8)

(wherein $R_4$ represents a protective group of a carboxyl group and $Y_4$ represents a leaving group.) Examples of a leaving group represented by $Y_4$ include a halogen atom, a methanesulfonyloxy group, a p-toluenesulfonyloxy group and a trifluoromethanesulfonyloxy group. The reaction is a ring-forming reaction of a thiazole ring and is performed by reacting the compounds (A-6) and (A-7) in an equivalent amount or using an excessive amount of one of the compounds in a solvent inactive to the reaction at room temperature to a reflux temperature under heating for generally 0.5 hours to 2 days. In addition, an equivalent or excessive amount of a base may be added. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethylsulfoxide (DMSO); or a mixed solvent thereof. Examples of the base to be used include: an inorganic salt such as sodium hydride, sodium hydroxide, potassium hydroxide, lithium hydroxide, sodium carbonate, potassium carbonate and cesium carbonate, a metal alkoxide such as sodium ethoxide and sodium methoxide; triethylamine; N-ethyl-N,N-diisopropylamine (DIPEA); and 1,8-diazabicyclo[5.4.0]-7-undecene (DBU).

Synthesis of Compound (A-9)

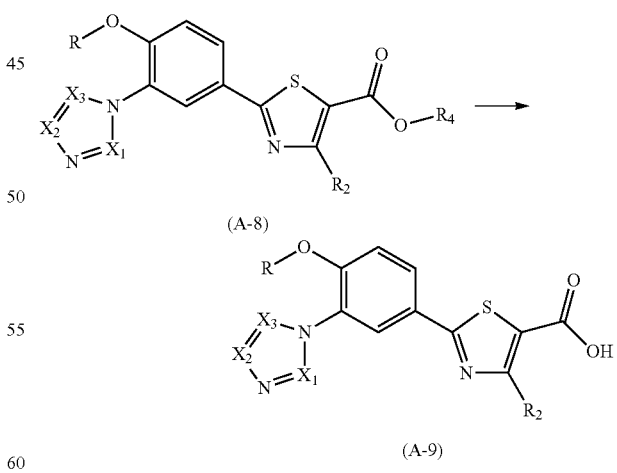

(A-8)

(A-9)

(wherein $R_4$ represents a protective group of a carboxyl group.) The synthesis method is a method for synthesizing a compound (A-9) of the present invention by deproteting a protective group $R_4$ of the compound (A-8) by an acid, a base or the like. The reaction is performed by reacting the compound (A-8) with an equivalent or excessive amount of an acid or a base in a solvent inactive to the reaction at room temperature to a reflux temperature under heating for generally 0.5 hours to 5 days. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; or a mixed solvent thereof. Examples of the acid include an inorganic acid such as hydrogen chloride, hydrogen bromide, sulfuric acid, nitric acid and phosphoric acid; or a solution obtained by diluting these acids with water or an organic solvent. Examples of the base include an inorganic salt such as sodium hydroxide, potassium hydroxide, lithium hydroxide, sodium carbonate, potassium carbonate, a metal alkoxide such as sodium ethoxide and sodium methoxide; or a solution obtained by diluting these bases with water or an organic solvent.

Synthesis of Compound (B-2)

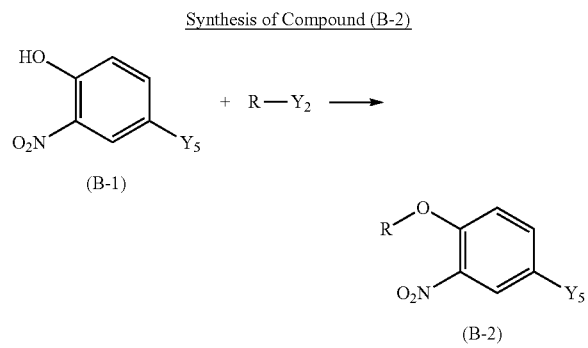

(wherein $Y_2$ and $Y_5$ represent a leaving group.) Examples of a leaving group represented by $Y_2$ and $Y_5$ include a halogen atom, a methanesulfonyloxy group, a p-toluenesulfonyloxy group and a trifluoromethanesulfonyloxy group. The reaction is a method for synthesizing a compound (B-2) by reacting a phenolic hydroxyl group in the compound (B-1) with an alkylating reagent having a leaving group in the presence of a base. Examples of the basic substance to be used include an inorganic salt such as sodium hydride, sodium hydroxide, potassium hydroxide, lithium hydroxide, sodium carbonate, potassium carbonate and cesium carbonate, a metal alkoxide such as sodium ethoxide, sodium methoxide and potassium t-butoxide or an organic amine such as triethylamine, pyridine, 4-aminopyridine, N-ethyl-N,N-diisopropylamine (DIPEA) and 1,8-diazabicyclo[5.4.0]-7-undecene (DBU). The reaction is performed by reacting the compound (B-1) with an equivalent or slightly excessive amount of a base in a solvent inactive to the reaction at 0° C. to 140° C., followed by adding an equivalent or excessive amount of an alkylating reagent to allow the reaction to proceed generally for 0.5 to 16 hours. The reaction is preferably performed under an inert gas atmosphere such as nitrogen. Here, the solvent includes, though not particularly limited, for example: ethers such as diethyl ether, tetrahydrofuran (THF), 1,4-dioxane, 1,2-dimethoxy ethane and 1,2-diethoxy ethane; N,N-dimethylformamide (DMF); N-methylpyrrolidone; dimethyl sulfoxide (DMSO); water; or a mixed solvent thereof.

In addition, the compound (B-2) may be synthesized, for example, according to the synthesis method described below.

Synthesis of Compound (B-2)

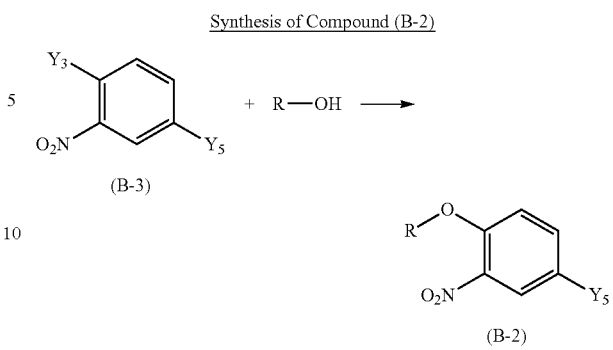

(wherein $Y_3$ and $Y_5$ represent a leaving group.) Examples of a leaving group represented by $Y_3$ and $Y_5$ include a halogen atom, a methanesulfonyloxy group, a p-toluenesulfonyloxy group and a trifluoromethanesulfonyloxy group. The reaction is a method for synthesizing a compound (B-2) by converting alcohols to corresponding lithium derivative, sodium derivative or potassium derivative with a base, followed by the reaction with a compound (B-3). Examples of the base to be used include an inorganic salt such as sodium hydride, sodium hydroxide, potassium hydroxide, lithium hydroxide, sodium carbonate, potassium carbonate and cesium carbonate, a metal alkoxide such as sodium ethoxide, sodium methoxide and t-potassium butoxide or an organic amine such as triethylamine, pyridine, 4-aminopyridine, N-ethyl-N,N-diisopropylamine (DIPEA) and 1,8-diazabicyclo[5.4.0]-7-undecene (DBU). The reaction is performed by reacting an equivalent or excessive amount of alcohols with an equivalent or slightly excessive amount of a base in a solvent inactive to the reaction at −20° C. to 120° C., followed by the addition of the compound (B-3) and allowing the reaction to proceed generally for 0.5 to 12 hours. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; N,N-dimethylformamide (DMF); N-methylpyrrolidone; dimethyl sulfoxide (DMSO); or a mixed solvent thereof.

Synthesis of Compound (B-5)

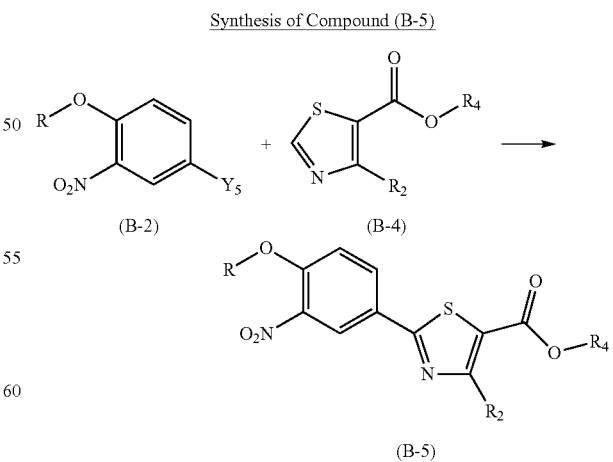

(wherein $R_4$ represents a protective group of a carboxyl group and $Y_5$ represents a leaving group.) The synthesis method is a method for synthesizing a compound (B-5) by coupling compounds (B-2) and (B-4). Examples of a leaving group represented by $Y_5$ include a halogen atom, a methanesulfonyloxy group, a p-toluenesulfonyloxy group and a trifluoromethanesulfonyloxy group. The reaction is performed by reacting the compounds (B-2) and (B-4) in an equivalent amount or using an excessive amount of one of the compounds and adding a ligand, a carboxylic acid and a monovalent or divalent copper salt in some cases, under the presence of a base and a transition metal catalyst in a solvent inactive to the reaction at room temperature to a reflux temperature under heating for generally 0.5 hours to 2 days. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water or a mixed solvent thereof. Examples of the base include: lithium hydride, sodium hydride, potassium hydride, sodium hydroxide, sodium hydroxide, potassium hydroxide, sodium carbonate, potassium carbonate, cesium carbonate, potassium fluoride, cesium fluoride, tripotassium phosphate, sodium acetate and potassium acetate; a metal salt of an alkoxide having 1 to 6 carbon atoms (lithium salt, sodium salt, potassium salt and magnesium salt); a metal salt of an alkyl anion having 1 to 6 carbon atoms (lithium salt, sodium salt, potassium salt and magnesium salt); tetra (alkyl having 1 to 4 carbon atoms) ammonium salt (fluoride, chloride and bromide); diisopropylethylamine; tributylamine; N-methylmorpholine; diazabicycloundecene; diazabicylcooctane; or imidazole. Examples of the transition metal catalyst include copper, palladium, cobalt, iron, rhodium, ruthenium and iridium. Examples of the ligand include tri(t-butyl)phosphine, tri(cyclohexyl)phosphine, t-butyldicyclohexylphosphine, di(t-butyl)cyclohexylphosphine or di(t-butyl)methylphosphine. Examples of the monovalent or divalent copper salt include copper chloride (I), copper bromide (I), copper iodide (I), copper acetate (I), copper fluoride (II), copper chloride (II), copper bromide (II), copper iodide (II), copper acetate (II), a hydrate thereof and a mixture thereof. Examples of the carboxylic acid include formic acid, acetic acid, propionic acid, n-butyric acid, isobutyric acid, pentanoic acid, isopentanoic acid, pivalic acid and trifluoroacetic acid.

Synthesis of Comound (B-6)

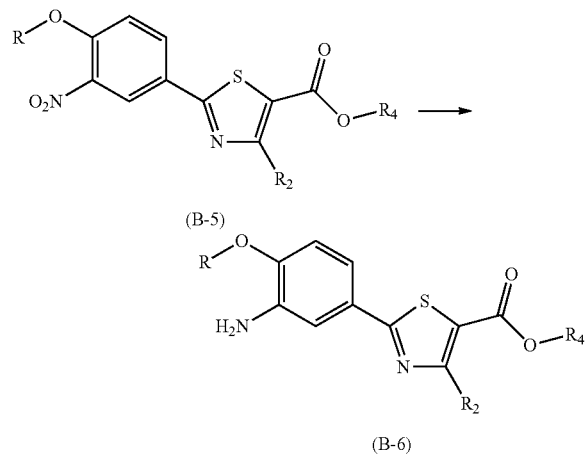

(wherein $R_4$ represents a protective group of a carboxyl group.) The synthesis method is a method for synthesizing a compound (B-6) by the reduction of a nitro group of a compound (B-5). The reaction is performed by reacting the compound (B-5) under a hydrogen gas atmosphere in the presence of a transition metal catalyst in a solvent inactive to the reaction at room temperature to a reflux temperature under heating for generally 0.5 hours to 2 days. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); ethyl acetate; or a mixed solvent thereof. Preferred examples of the transition metal catalyst include palladium-carbon, palladium hydroxide, palladium black, platinum-carbon, Raney nickel, and the like.

Synthesis of Compound (B-9)

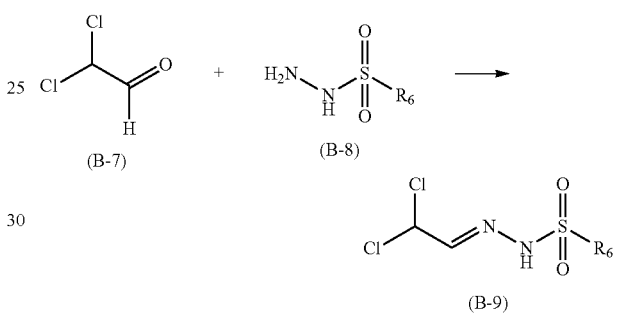

(wherein $R_6$ represents a methyl group or a p-tolyl group.) The synthesis method may be referred to HETEROCYCLES, VOL. 48, No. 4, 1998, P695-702. That is, the synthesis method is a method for synthesizing a compound (B-9) by the condensation of compounds (B-7) and (B-8). The reaction is performed by reacting the compounds (B-7) and (B-8) in an equivalent amount or using an excessive amount of one of the compounds in a solvent inactive to the reaction at 0° C. to a reflux temperature under heating for generally 0.5 hours to 1 day. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; N,N-dimethylformamide (DMF); N-methylpyrrolidone; dimethyl sulfoxide (DMSO); acetic acid; propionic acid; or a mixed solvent thereof.

Synthesis of Compound (B-10)

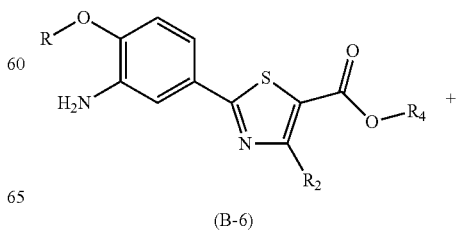

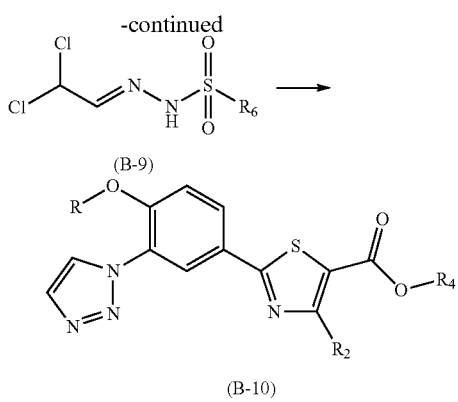

(wherein R₄ represents a protective group of a carboxyl group and R₆ represents a methyl group or a p-tolyl group.) The synthesis method is a method for synthesizing a 1,2,3-triazole ring by reacting the compound (B-6) and the compound (B-9). The reaction is performed by reacting the compound (B-6) and the compound (B-9) in an equivalent amount or using an excessive amount of one of the compounds in the presence of a base in a solvent inactive to the reaction at room temperature to a reflux temperature under heating for generally 0.5 hours to 2 days. The reaction is preferably performed under an inert gas atmosphere such as nitrogen. Examples of the base to be used include a carbonate such as potassium carbonate, sodium carbonate and sodium hydrogen carbonate or an organic amine such as triethylamine, pyridine, 4-aminopyridine, N-ethyl-N,N-diisopropylamine (DIPEA) and 1,8-diazabicyclo[5.4.0]-7-undecene (DBU). Examples of the solvent to be used for these reactions include toluene, benzene, pyridine, ethyl acetate, dichloromethane, dichloroethane, chloroform, carbon tetrachloride, diethyl ether, tetrahydrofuran (THF), 1,4-dioxane, 1,2-dimethoxy ethane, 1,2-diethoxy ethane, N,N-dimethylformamide (DMF), N-methylpyrrolidone, dimethyl sulfoxide (DMSO) or a mixed solvent thereof.

Synthesis of Compound (B-11)

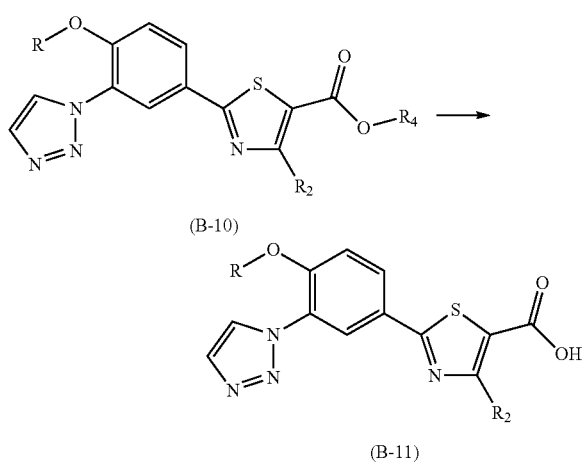

(wherein R₄ represents a protective group of a carboxyl group.) The synthesis method is a method for synthesizing a compound (B-11) of the present invention by deprotecting a protective group R₄ of the compound (B-10) with an acid, a base or the like. The reaction is performed by reacting the compound (B-10) with an equivalent or excessive amount of an acid or a base in a solvent inactive to the reaction at room temperature to a reflux temperature under heating for generally 0.5 hours to 5 days. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; or a mixed solvent thereof. Examples of the acid include an inorganic acid such as hydrogen chloride, hydrogen bromide, sulfuric acid, nitric acid and phosphoric acid or a solution obtained by diluting these acids with water or an organic solvent. Examples of the base include an inorganic salt such as sodium hydroxide, potassium hydroxide, lithium hydroxide, sodium carbonate and potassium carbonate, a metal alkoxide such as sodium ethoxide and sodium methoxide or a solution obtained by diluting these bases with water or an organic solvent.

Synthesis Method (C)

Synthesis of Compound (C-1)

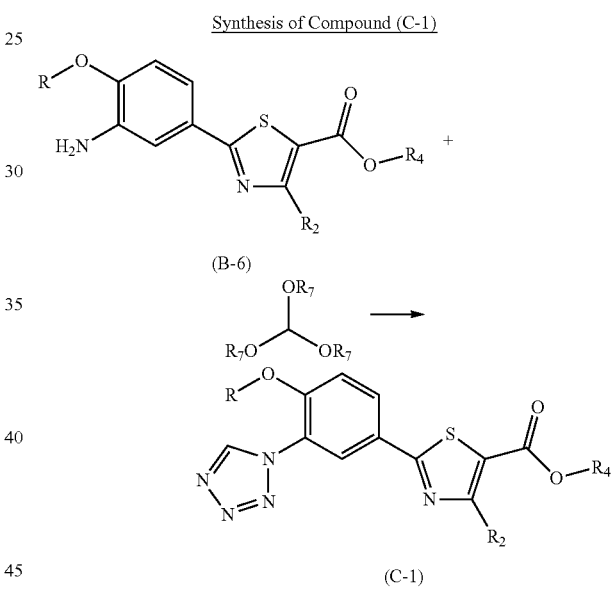

(wherein R₄ represents a protective group of a carboxyl group and R₇ represents an alkyl group such as a methyl group or an ethyl group.) The synthesis method is a method for synthesizing a tetrazole ring by reacting the compound (B-6) with an ortho-formic acid ester and an azide compound. The reaction is performed by reacting the compound (B-6), an ortho-formic acid ester and an azide compound in an equivalent amount or using an excessive amount of one of the compounds in the presence of an acid in a solvent inactive to the reaction at room temperature to a reflux temperature under heating for generally 0.5 hours to 2 days. The reaction is preferably performed under an inert gas atmosphere such as nitrogen. Examples of the ortho-formic acid ester include trimethyl ortho-formate and triethyl ortho-formate. In addition, examples of the azide compound include sodium azide and trimethyl silylazide. Examples of the acid to be used include an organic acid such as formic acid and acetic acid, an inorganic acid such as hydrochloric acid and sulfuric acid or a Lewis acid such as indium triflate, ytterbium triflate, zinc triflate and trichloroindium. The solvent to be used for these reactions includes, though not particularly limited, for example benzene, toluene, dichloromethane, dichloroethane, chloroform, carbon tetrachloride, diethyl ether, tetrahydrofuran (THF), 1,4-dioxane, 1,2-dimethoxy ethane, 1,2-diethoxy ethane, N,N-dimethylformamide (DMF), N-methylpyrrolidone, dimethyl sulfoxide (DMSO) or a mixed solvent thereof, and an acid such as acetic acid may also be used as a solvent.

Synthesis of Compound (C-2)

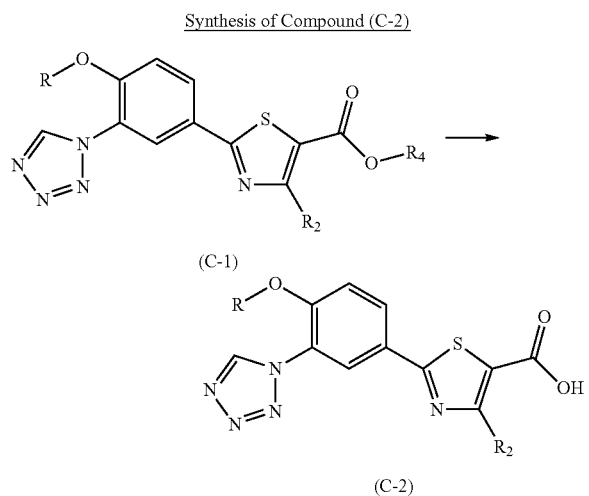

(wherein $R_4$ represents a protective group of a carboxyl group.) The synthesis method is a method for synthesizing a compound (C-2) of the present invention by deprotecting a protective group $R_4$ of the compound (C-1) with an acid, a base or the like. The reaction is performed by reacting the compound (C-1) with an equivalent or excessive amount of an acid or a base in a solvent inactive to the reaction at room temperature to a reflux temperature under heating for generally 0.5 hours to 5 days. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; or a mixed solvent thereof. Examples of the acid include an inorganic acid such as hydrogen chloride, hydrogen bromide, sulfuric acid, nitric acid and phosphoric acid or a solution obtained by diluting these acids with water or an organic solvent. Examples of the base include an inorganic salt such as sodium hydroxide, potassium hydroxide, lithium hydroxide, sodium carbonate and potassium carbonate, a metal alkoxide such as sodium ethoxide and sodium methoxide or a solution obtained by diluting these bases with water or an organic solvent.

Synthesis of Compound (C-4)

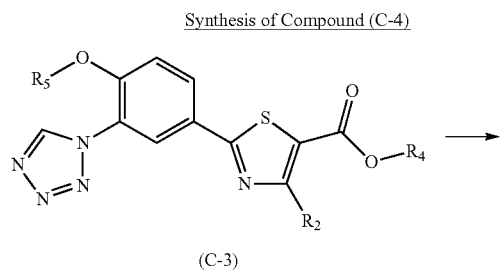

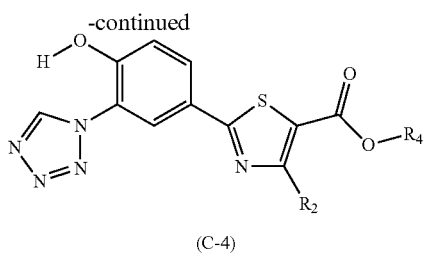

(wherein $R_4$ represents a protective group of a carboxyl group and $R_5$ represents a protective group of a phenolic hydroxyl group.) The synthesis method is a method for synthesizing a compound (C-4) by deprotecting a protective group $R_5$ of the compound (C-3) with an acid, a base or the like. The reaction is performed by reacting the compound (C-3) with an equivalent or excessive amount of an acid or a base in a solvent inactive to the reaction at room temperature to a reflux temperature under heating for generally 0.5 hours to 5 days. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; or a mixed solvent thereof. Examples of the acid include an inorganic acid such as hydrogen chloride, hydrogen bromide, sulfuric acid, nitric acid and phosphoric acid or a solution obtained by diluting these acids with water or an organic solvent. Examples of the base include an inorganic salt such as sodium hydroxide, potassium hydroxide, lithium hydroxide, sodium carbonate, potassium carbonate, sodium ethocide and sodium methoxide or a solution obtained by diluting these bases with water or an organic solvent.

In addition, the compound (C-1) may be synthesized, for example, according to the synthesis method described below.

Synthesis of Compound (C-1)

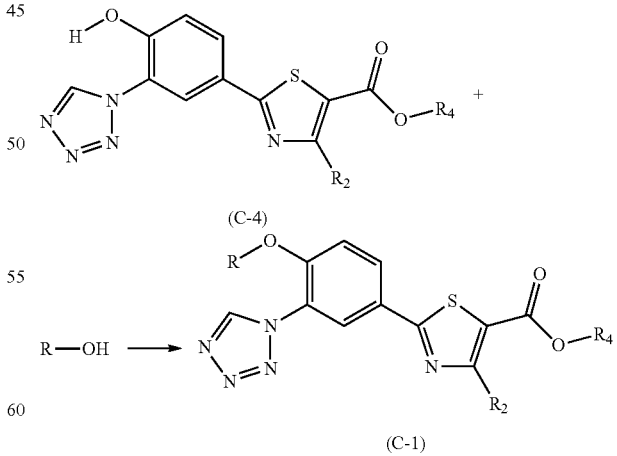

(wherein $R_4$ represents a protective group of a carboxyl group.) The synthesis method is a method for synthesizing the compound (C-1) by reacting the compound (C-4) with alcohols by Mitsunobu reaction or the like. The reaction is a method for synthesizing the compound (C-1) by reacting alcohols with triphenylphosphine and carbodiimide, followed by reacting with the compound (C-4). Examples of the carbodiimide to be used include diethylcarbodiimide and diisopropylcarbodiimide. The reaction is performed by reacting the compound (C-4) with an equivalent or excessive amount of alcohols, triphenylphosphine and carbodiimide in a solvent inactive to the reaction at −20° C. to 120° C. generally for 0.5 to 12 hours. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; N,N-dimethylformamide (DMF); N-methylpyrrolidone; dimethyl sulfoxide (DMSO); or a mixed solvent thereof.

Synthesis of Compound (D-1)

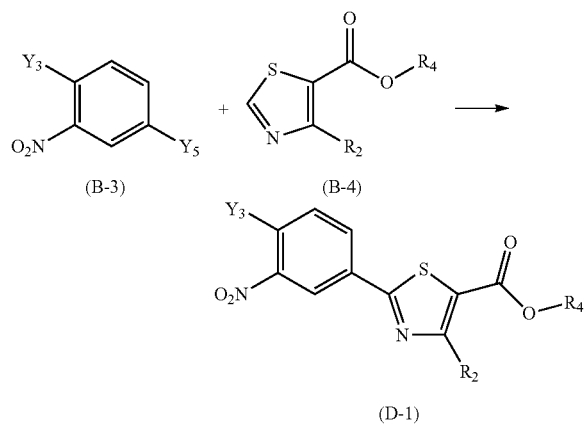

(wherein $R_4$ represents a protective group of a carboxyl group and $Y_3$ and $Y_5$ represent a leaving group.) Examples of a leaving group represented by $Y_3$ and $Y_5$ include a halogen atom, a methanesulfonyloxy group, a p-toluenesulfonyloxy group and a trifluoromethanesulfonyloxy group. The synthesis method is a method for synthesizing a compound (D-1) by coupling compounds (B-3) and (B-4). The reaction is performed by reacting the compounds (B-3) and (B-4) in an equivalent amount or using an excessive amount of one of the compounds and adding a ligand, carboxylic acid and a monovalent or divalent copper salt in some cases, in the presence of a base and a transition metal catalyst in a solvent inactive to the reaction at room temperature to a reflux temperature under heating for generally 0.5 hours to 2 days. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water or a mixed solvent thereof. Examples of the base include: lithium hydride, sodium hydride, potassium hydride, sodium hydroxide, potassium hydroxide, sodium carbonate, potassium carbonate, cesium carbonate, potassium fluoride, cesium fluoride, tripotassium phosphate, sodium acetate and potassium acetate; a metal salt of an alkoxide having 1 to 6 carbon atoms (lithium salt, sodium salt, potassium salt and magnesium salt); a metal salt of an alkyl anion having 1 to 6 carbon atoms (lithium salt, sodium salt, potassium salt and magnesium salt); tetra (alkyl having 1 to 4 carbon atoms) ammonium salt (fluoride, chloride and bromide); diisopropylethylamine; tributylamine; N-methylmorpholine; diazabicycloundecene; diazabicyclooctane; or imidazole. Examples of the transition metal catalyst include copper, palladium, cobalt, iron, rhodium, ruthenium and iridium. Examples of the ligand include tri(t-butyl)phosphine, tri(cyclohexyl)phosphine, t-butyldicyclohexylphosphine, di(t-butyl)cyclohexylphosphine or di(t-butyl)methylphosphine. Examples of the monovalent or divalent copper salt include copper chloride (I), copper bromide (I), copper iodide (I), copper acetate (I), copper fluoride (II), copper chloride (II), copper bromide (II), copper iodide (II), copper acetate (II), a hydrate thereof or a mixture thereof. Examples of the carboxylic acid include formic acid, acetic acid, propionic acid, n-butyric acid, isobutyric acid, pentanoic acid, isopentanoic acid, pivalic acid and trifluoroacetic acid.

Synthesis of Compound (D-2)

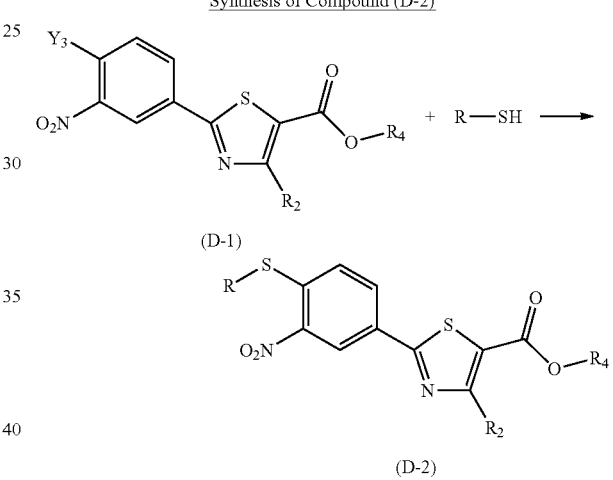

(wherein $R_4$ represents a protective group of a carboxyl group and $Y_3$ represents a leaving group.) Examples of a leaving group represented by $Y_3$ include a halogen atom, a methanesulfonyloxy group, a p-toluenesulfonyloxy group and a trifluoromethanesulfonyloxy group. The reaction is a method for synthesizing a compound (D-2) by converting thiols to corresponding lithium derivative, sodium derivative, potassium derivative or cesium derivative with a base, followed by the reaction with the compound (D-1). Examples of the base to be used include an inorganic salt such as sodium hydride, sodium hydroxide, potassium hydroxide, lithium hydroxide, sodium carbonate, potassium carbonate and cesium carbonate, a metal alkoxide such as sodium ethoxide, sodium methoxide and potassium t-butoxide or an organic amine such as triethylamine, pyridine, 4-aminopyridine, N-ethyl-N,N-diisopropylamine (DIPEA) and 1,8-diazabicyclo[5.4.0]-7-undecene (DBU). The reaction is performed by reacting the compound (D-1) with an equivalent or slightly excessive amount of a base in a solvent inactive to the reaction at −20° C. to 120° C., followed by adding an equivalent or excessive amount of thiols to allow the reaction to proceed generally for 0.5 to 12 hours. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; N,N-dimethylformamide (DMF); N-methylpyrrolidone; dimethyl sulfoxide (DMSO); or a mixed solvent thereof.

Synthesis of Compound (D-3)

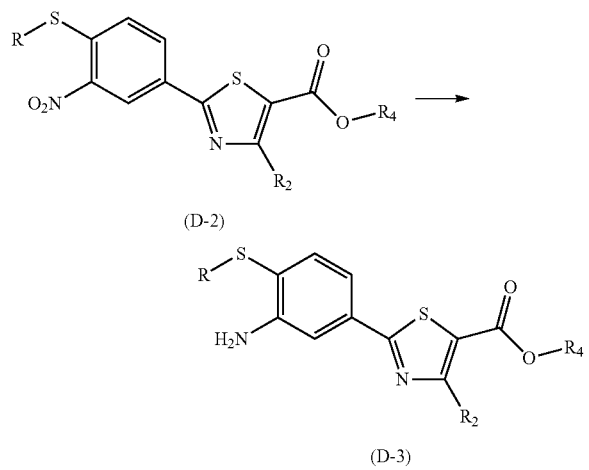

(wherein R$_4$ represents a protective group of a carboxyl group.) The synthesis method is a method for synthesizing a compound (D-3) by the reduction of a nitro group of the compound (D-2). The reaction is performed by reacting the compound (D-2) in a hydrogen gas atmosphere under the presence of a transition metal catalyst in a solvent inactive to the reaction at room temperature to a reflux temperature under heating for generally 0.5 hours to 2 days. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; ethyl acetate; N,N-dimethylformamide (DMF); N-methylpyrrolidone; dimethyl sulfoxide (DMSO); or a mixed solvent thereof. Preferred examples of the transition metal catalyst include palladium-carbon, palladium hydroxide, palladium black, platinum-carbon, Raney nickel and the like.

Synthesis of Compound (D-4)

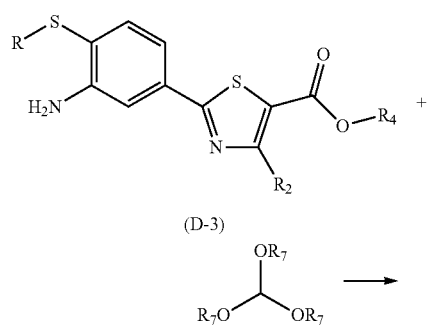

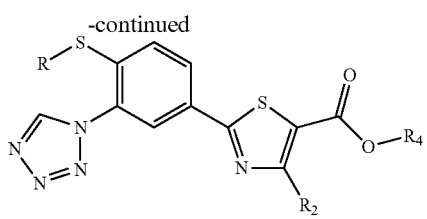

(wherein R$_4$ represents a protective group of a carboxyl group and R$_7$ represents an alkyl group such as a methyl group or an ethyl group.) The synthesis method is a method for synthesizing a tetrazole ring by reacting the compound (D-3) with an ortho-formic acid ester and an azide compound. The reaction is performed by reacting the compound (D-3), an ortho-formic acid ester and an azide compound in an equivalent amount or using an excessive amount of one of the compounds in the presence of an acid in a solvent inactive to the reaction at room temperature to a reflux temperature under heating for generally 0.5 hours to 2 days. The reaction is preferably performed under an inert gas atmosphere such as nitrogen. Examples of the ortho-formic acid ester include trimethyl ortho-formate and triethyl ortho-formate. In addition, examples of the azide compound include sodium azide and trimethyl silylazide. Examples of the acid to be used include an organic acid such as formic acid and an inorganic acid such as acetic acid, hydrochloric acid and sulfuric acid and a Lewis acid such as indium triflate, ytterbium triflate, zinc triflate and trichloroindium. The solvent includes, though not particularly limited, for example benzene, toluene, dichloromethane, dichloroethane, chloroform, carbon tetrachloride, diethyl ether, tetrahydrofuran (THF), 1,4-dioxane, 1,2-dimethoxy ethane, 1,2-diethoxy ethane, N,N-dimethylformamide (DMF), N-methylpyrrolidone, dimethyl sulfoxide (DMSO) or a mixed solvent thereof, and an acid such as acetic acid may also be used as a solvent.

Synthesis of Compound (D-5)

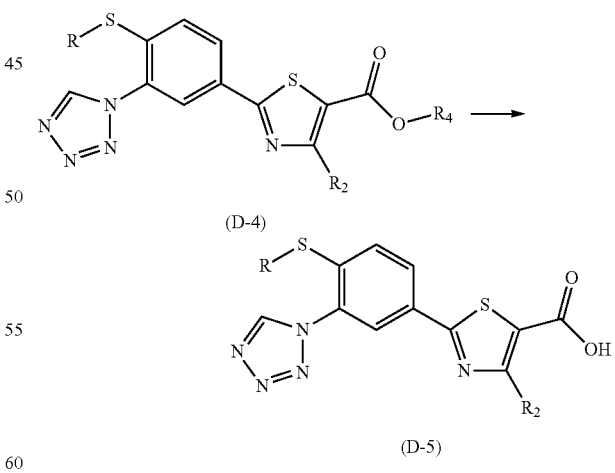

(wherein R$_4$ represents a protective group of a carboxyl group.) The synthesis method is a method for synthesizing a compound (D-5) of the present invention by deprotecting a protective group R$_4$ of the compound (D-4) with an acid, a base or the like. The reaction is performed by reacting the compound (D-4) with an equivalent or excessive amount of an acid or a base in a solvent inactive to the reaction at room temperature to a reflux temperature under heating for generally 0.5 hours to 5 days. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; or a mixed solvent thereof. Examples of the acid include an inorganic acid such as hydrogen chloride, hydrogen bromide, sulfuric acid, nitric acid and phosphoric acid or a solution obtained by diluting these acids with water or an organic solvent. Examples of the base include an inorganic salt such as sodium hydroxide, potassium hydroxide, lithium hydroxide, sodium carbonate and potassium carbonate, a metal alkoxide such as sodium ethoxide and sodium methoxide or a solution obtained by diluting these bases with water or an organic solvent.

Synthesis Method (E)

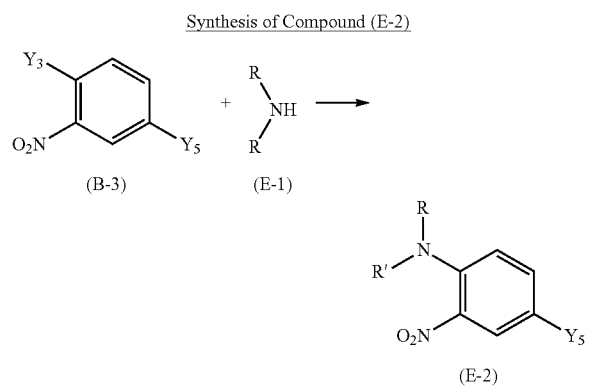

(wherein $Y_3$ and $Y_5$ represent a leaving group.) Examples of the leaving group represented by $Y_3$ and $Y_5$ include a halogen atom, a methanesulfonyloxy group, a p-toluenesulfonyloxy group and a trifluoromethanesulfonyloxy group. The reaction is a method for synthesizing a compound (E-2) by converting amines to corresponding lithium derivative, sodium derivative, potassium derivative or cesium derivative with a base, followed by the reaction with the compound (B-3). Examples of the base to be used include an inorganic salt such as sodium hydride, sodium hydroxide, potassium hydroxide, lithium hydroxide, sodium carbonate, potassium carbonate and cesium carbonate, a metal alkoxide such as sodium ethoxide, sodium methoxide and potassium t-butoxide and an organic amine such as triethylamine, pyridine, 4-aminopyridine, N-ethyl-N,N-diisopropylamine (DIPEA) and 1,8-diazabicyclo[5.4.0]-7-undecene (DBU). The reaction is performed by reacting amines (E-1) with an equivalent or slightly excessive amount of a base in a solvent inactive to the reaction at −20° C. to 120° C., followed by adding the compound (B-3) to allow the reaction to proceed generally for 0.5 to 12 hours. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; N,N-dimethylformamide (DMF); N-methylpyrrolidone; dimethyl sulfoxide (DMSO); or a mixed solvent thereof.

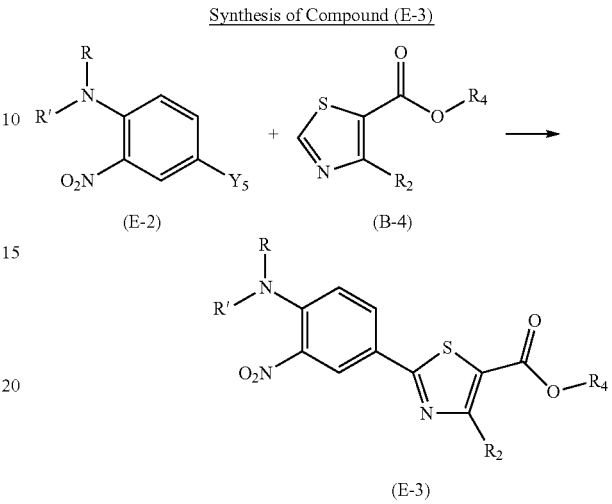

(wherein $R_4$ represents a protective group of a carboxyl group and $Y_5$ represent a leaving group.) The synthesis method is a method for synthesizing a compound (E-3) by coupling the compounds (E-2) and (B-4). Examples of the leaving group represented by $Y_5$ include a halogen atom, a methanesulfonyloxy group, a p-toluenesulfonyloxy group and a trifluoromethanesulfonyloxy group. The reaction is performed by reacting the compounds (E-2) and (B-4) in an equivalent amount or using an excessive amount of one of the compounds, and adding a ligand, carboxylic acid and a monovalent or divalent copper salt in some cases, in the presence of a base and a transition metal catalyst in a solvent inactive to the reaction at room temperature to a reflux temperature under heating for generally 0.5 hours to 2 days. The reaction is preferably performed under an inert gas atmosphere such as nitrogen. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water or a mixed solvent thereof. Examples of the base include: lithium hydride, sodium hydride, potassium hydride, sodium hydroxide, potassium hydroxide, sodium carbonate, potassium carbonate, cesium carbonate, potassium fluoride, cesium fluoride, tripotassium phosphate, sodium acetate and potassium acetate; a metal salt of an alkoxide having 1 to 6 carbon atoms (lithium salt, sodium salt, potassium salt and magnesium salt); a metal salt of an alkyl anion having 1 to 6 carbon atoms (lithium salt, sodium salt, potassium salt and magnesium salt); tetra (alkyl having 1 to 4 carbon atoms) ammonium salt (fluoride, chloride and bromide); diisopropylethylamine; tributylamine; N-methylmorpholine; diazabicycloundecene; diazabicyclooctane; or imidazole. Examples of the transition metal catalyst include copper, palladium, cobalt, iron, rhodium, ruthenium and iridium. Examples of the ligand include tri(t-butyl)phosphine, tri (cyclohexyl)phosphine, t-butyldicyclohexylphosphine, di(t- butyl)cyclohexylphosphine or di(t-butyl)methylphosphine. Examples of the monovalent or divalent copper salt include copper chloride (I), copper bromide (I), copper iodide (I), copper acetate (I), copper fluoride (II), copper chloride (II), copper bromide (II), copper iodide (II), copper acetate (II), a hydrate thereof and a mixture thereof. Examples of the carboxylic acid include formic acid, acetic acid, propionic acid, n-butyric acid, isobutyric acid, pentanoic acid, isopentanoic acid, pivalic acid and trifluoroacetic acid.

Synthesis of Compound (E-4)

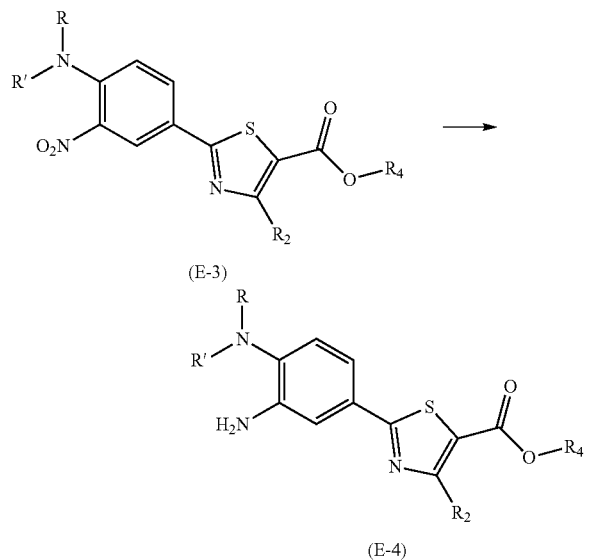

(wherein $R_4$ represents a protective group of a carboxyl group.) The synthesis method is a method for synthesizing a compound (E-4) by the reduction of a nitro group of the compound (E-3). The reaction is performed by reacting the compound (E-3) in a hydrogen gas atmosphere under the presence of a transition metal catalyst in a solvent inactive to the reaction at room temperature to a reflux temperature under heating for generally 0.5 hours to 2 days. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; ethyl acetate; N,N-dimethylformamide (DMF); N-methylpyrrolidone; dimethyl sulfoxide (DMSO); or a mixed solvent thereof. Preferred examples of the transition metal catalyst include palladium-carbon, palladium hydroxide, palladium black, platinum-carbon and Raney nickel.

Synthesis of Compound (E-5)

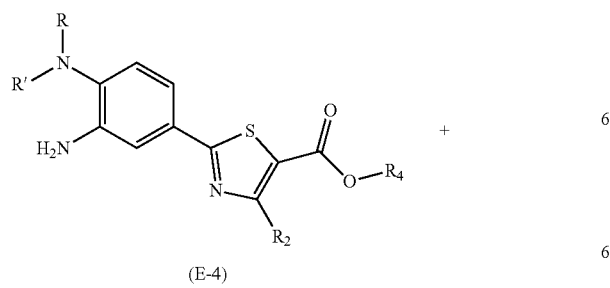

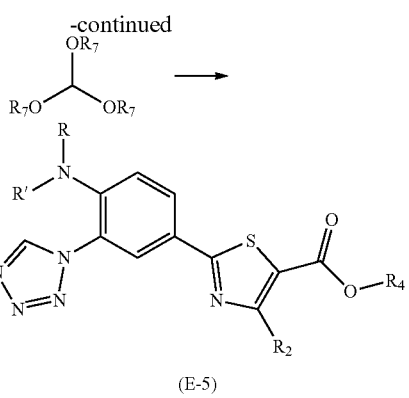

(wherein $R_4$ represents a protective group of a carboxyl group and $R_7$ represents an alkyl group such as a methyl group or an ethyl group.) The synthesis method is a method for synthesizing a terazole ring by reacting the compound (E-4) with an ortho-formic acid ester and an azide compound. The reaction is performed by reacting the compound (E-4), an ortho-formic acid ester and an azide compound in an equivalent amount or using an excessive amount of one of the compounds in the presence of an acid in a solvent inactive to the reaction at room temperature to a reflux temperature under heating for generally 0.5 hours to 2 days. The reaction is preferably performed under an inert gas atmosphere such as nitrogen. Examples of the ortho-formic acid ester include trimethyl ortho-formate and triethyl ortho-formate. In addition, examples of the azide compound include sodium azide and trimethyl silylazide. Examples of the acid to be used include an organic acid such as formic acid and acetic acid; an inorganic acid such as hydrochloric acid and sulfuric acid or a Lewis acid such as indium triflate, ytterbium triflate, zinc triflate and trichloroindium. Examples of the solvent to be used for these reaction include toluene, benzene, dichloromethane, dichloroethane, chloroform, carbon tetrachloride, diethyl ether, tetrahydrofuran (THF), 1,4-dioxane, 1,2-dimethoxy ethane, 1,2-diethoxy ethane, N,N-dimethylformamide (DMF), N-methylpyrrolidone, dimethyl sulfoxide (DMSO) or a mixed solvent thereof, and an acid such as acetic acid may also be used as a solvent.

Synthesis of Compound (E-6)

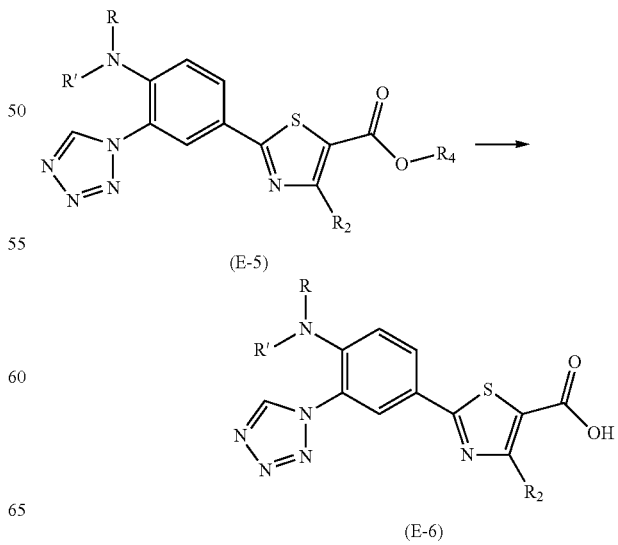

(wherein $R_4$ represents a protective group of a carboxyl group.) The synthesis method is a method for synthesizing a compound (E-6) of the present invention by deprotecting a protective group $R_4$ of the compound (E-5) with an acid, a base or the like. The reaction is performed by reacting the compound (E-5) with an equivalent or excessive amount of an acid or a base in a solvent inactive to the reaction at room temperature to a reflux temperature under heating for generally 0.5 hours to 5 days. Here, the solvent includes, though not particularly limited, for example: aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; or a mixed solvent thereof. Examples of the acid include an inorganic acid such as hydrogen chloride, hydrogen bromide, sulfuric acid, nitric acid and phosphoric acid or a solution obtained by diluting these acids with water or an organic solvent. Examples of the base include an inorganic salt such as sodium hydroxide, potassium hydroxide, lithium hydroxide, sodium carbonate, potassium carbonate, a metal alkoxide such as sodium ethoxide and sodium methoxide or a solution obtained by diluting these bases with water and the like. n the above synthesis methods, the compounds of the formulas (A-8), (B-10), (C-1), (C-4), (D-4) and (E-5) correspond to the compound of the formula (II), which is a manufacturing intermediate of the compound represented by the formula (I), and the compound of the formula (C-3) corresponds to the compound of the formula (III).

Hereinafter, among the compounds represented by the formula (I), preferred compounds and pharmaceutically acceptable salts thereof include though not particularly limited, for example, a salt with an inorganic acid such as hydrochloric acid, hydrogen bromide, sulfuric acid, nitric acid, phosphoric acid and carbonic acid; a salt with an organic acid such as maleic acid, fumaric acid, citric acid, malic acid, tartaric acid, lactic acid, succinic acid, benzoic acid, oxalic acid, methanesulfonic acid, benzenesulfonic acid, p-toluenesulfonic acid, acetic acid, trifluoroacetic acid and formic acid; a salt with an amino acid such as glycine, lysine, arginine, histidine, ornithine, glutamic acid and aspartic acid; a salt with an alkali metal such as sodium, potassium and lithium; a salt with an alkali earth metal such as calcium and magnesium; a salt with metal such as aluminum, zinc and iron; a salt with an organic onium such as tetramethylammonium and choline; or a salt with an organic base such as ammonia, propanediamine, pyrrolidine, piperidine, pyridine, ethanolamine, N,N-dimethylethanolamine, 4-hydroxypiperidine, t-octylamine, dibenzylamine, morpholine, glucosamine, phenylglycylalkyl ester, ethylenediamine, N-methylglucamine, guanidine, diethylamine, triethylamine, dicyclohexylamine, N,N'-dibenzylethylenediamine, chloroprocaine, procaine, diethanolamine, N-benzylphenylamine, piperazine, and tris(hydroxymethyl)aminomethane.

Further, examples of the compound represented by the formula (I) and a salt thereof include various hydrates and solvates. The solvent of the solvates includes, though not particularly limited, for example methanol, ethanol, 1-propanol, 2-propanol, butanol, t-butanol, acetonitrile, acetone, methyl ethyl ketone, chloroform, ethyl acetate, diethyl ether, t-butylmethyl ether, tetrahydrofuran (THF), 1,4-dioxane, 1,2-dimethoxy ethane, 1,2-diethoxy ethane, benzene, toluene, DMF and DMSO.

The above various pharmaceutically acceptable salts of the compound represented by the formula (I) may be appropriately manufactured based on conventional knowledge in the art.

Examples of the compound of the present invention include stereoisomers, recemates and all possible optically active substances of the compound represented by the formula (1) and a salt thereof.

A compound represented by the formula (I) and a pharmaceutically acceptable salt thereof have especially excellent xanthine oxidase inhibitory activity. Because of the excellent xanthine oxidase inhibitory activity, the compound represented by the formula (I) and the pharmaceutically acceptable salt thereof are useful as a xanthine oxidase inhibitor.

A compound represented by the formula (I) of the present invention and a pharmaceutically acceptable salt thereof may be used as a therapeutic agent or a preventive agent which can be clinically applied as a xanthine oxidase inhibitor for diseases associated with xanthine oxidase such as gout, hyperuricemia, tumor lysis syndrome, urinary calculi, hypertension, dyslipidemia, diabetes, kidney diseases such as diabetic nephropathy, respiratory diseases such as chronic obstructive pulmonary diseases, inflammatory bowel diseases or autoimmune diseases.

In the present invention, the term "prophylactic" means to prevent the incidence or onset of diseases in an individual who is not affected by diseases or has not yet developed diseases and the term "therapeutic" means to treat, suppress or remedy diseases or symptoms in an individual who has already been affected by diseases or has developed diseases.

In the present invention, a vascular endothelial function is a function to regulate shrinkage and relaxation of vessel walls caused by various vasoactive substance released by vascular endothelium, adhesion of inflammatory cells to vessel walls, blood vessel permeability and congealing fibrinogenolysis system, and a vascular endothelial function disorder is a state in which these regulations do not function normally due to a disorder caused by some kind of reason.

A compound of the present invention represented by the formula (I) and a pharmaceutically acceptable salt thereof are useful as a drug for improving vascular endothelial function through the inhibition of reactive oxygen species production by the xanthine oxidase inhibition in blood vessel. Here, the vascular endothelial function improvement refers to bringing a vascular endothelial function close to a normal state.

The compound represented by the above-mentioned formula (1) and the pharmaceutically acceptable salt thereof can be used to prepare a pharmaceutical composition together with a pharmaceutically acceptable carrier and/or excipient. The pharmaceutical composition can be formed into various formulations for oral or parenteral administration. Examples of a parenteral administration include intravenous, subcutaneous, intramuscular, percutaneous or intrarectal administration.

A drug formulation containing one or more of the compounds represented by formula (1) of the present invention or the pharmaceutically acceptable salt thereof as an active ingredient is prepared using a carrier, an excipient or other additives which are usually used for drug formulation. Any of solid and liquid forms may be used as a carrier or an excipient for pharmaceutical preparations, and examples of which include lactose, magnesium stearate, starch, talc, gelatin, agar, pectin, gum arabic, olive oil, sesame oil, cacao butter, ethyleneglycol, and others in common use. Administration may be done in any form of oral administration with tablets, pills, capsules, granules, powders, liquids or the like, parenteral administration by injections for intravenous or intramuscular injection, suppository, percutaneous administration or the like.

A compound represented by the formula (1) of the present invention or a pharmaceutically acceptable salt thereof can be administered usually in the range of 0.01 to 1,000 mg once or several times a day for adult. However, the dosage varies depending on the kind of disease, administration route, or symptom, age, sex or body weight of the patient, and the like. However, since the dosage varies according to various conditions, a dosage smaller than the above-mentioned dosage may be sufficient in some cases and a dosage exceeding the above range may be necessary in other cases.

EXAMPLES

Hereinafter, the present invention will be explained based on specific examples. However, the present invention is not limited to these examples.

The structure of the novel compound isolated was confirmed by $^1$H-NMR and/or mass spectrometry using single quadrupole instrumentation equipped with an electron spray source and other appropriate analytical methods.

As for the compounds for which $^1$H-NMR spectrum (300 MHz or 400 MHz, DMSO-$d_6$ or CDCl$_3$) was measured, the chemical shift (δ: ppm) and coupling constant (J: Hz) are shown. As for the result of mass spectroscopy, the observed value of M$^+$+H, that is, the observed value is shown as the value of the molecular mass of the compound (M) with a proton (H$^+$). In addition, the following abbreviations represent the followings, respectively: s=singlet, d=doublet, t=triplet, q=quartet, brs=broad singlet, m=multiplet.

The compounds synthesized according to the following methods of examples were further analyzed by high performance liquid chromatography (HPLC) analysis and mass spectrometry using Time-of-Flight mass spectrometer equipped with an electron spray source.

The retention time (unit: min.) of compounds in the HPLC analysis under the following analytical conditions is shown as HPLC retention time.

HPLC Measurement Conditions
Measurement Device: Hewlett-Packard 1100 HPLC
Column: Imtakt Cadenza CD-C18 100 mm×4.6 mm 3 μm
UV: PDA detection (254 nm)
Column Temperature: 40° C.
Gradient Conditions:
Solvent: A: H$_2$O/acetonitrile=95/5
0.05% TFA (trifluoroacetic acid)
B: H$_2$O/acetonitrile=5/95
0.05% TFA (trifluoroacetic acid)
Flow Rate: 1.0 mL/min

| Gradient: | 0 to 1 min, | Solvent B: 2%, | Solvent A: 98% |
|---|---|---|---|
| | 1 to 14 min, | Solvent B: 2% to 100%, | Solvent A: 98% to 0% |
| | 14 to 17 min, | Solvent B: 100%, | Solvent A: 0% |
| | 17 to 19 min, | Solvent B: 100% to 2%, | Solvent A: 0% to 98% |

In addition, for the result of the mass analysis, the value of "M$^+$+H" (Obs. Mass: that is, the observed value in which a proton is added to the molecular mass (M) of the compound), which was observed by the following devices and analytical conditions, and the formulas calculated from the value of "M$^+$+H" observed are shown together with the calculated values of "M$^+$+H" (Pred. Mass).

TOF-MS Measurement Conditions
Mass Spectrometer: Shimadzu LCMS-IT-TOF
LC: Prominence
Column: Phenomenex×Synergi Hydro-RP 4.0 mm×20 mm 2.5 μm
UV: PDA detection (254 nm)
Flow Rate: 0.6 mL/min
Column Temperature: 40° C.
Detection Voltage: 1.63 kV
Gradient Conditions:
Solvent: A: H$_2$O/acetonitrile=95/5
0.1% HCOOH
B: H$_2$O/acetonitrile=5/95
0.1% HCOOH
Flow Rate: 0.5 mL/min

| Gradient: | 0 to 0.2 min, | Solvent B: 2%, | Solvent A: 98% |
|---|---|---|---|
| | 0.2 to 2.5 min, | Solvent B: 2% to 100%, | Solvent A: 98% to 0% |
| | 2.5 to 3.8 min, | Solvent B: 100%, | Solvent A: 0% |
| | 3.8 to 4.0 min, | Solvent B: 100% to 2%, | Solvent A: 0% to 98% |
| | 4.0 to 5.0 min, | Solvent B: 2%, | Solvent A: 98% |

Reference Example

Synthesis of N'-[(1E)-2,2-dichloroethylidene]-4-methylbenzene-1-sulfonehydrazine (Reference Example Compound)

A reaction solution was prepared by dissolving 1.86 g of p-toluenesulfonylhydrazine in 4 mL of propionic acid and cooling at 0° C. and adding dropwise slowly a solution prepared by dissolving 1.36 g of dichloroacetaldehyde hydrate in 8 mL of propionic acid. The reaction solution was stirred at 0° C. for one hour and the precipitated solid was filtered, washed using 10 mL of toluene and dried to obtain 1.98 g of N'-[(1E)-2,2-dichloroethylidene]-4-methylbenzene-1-sulfonehydrazine.

$^1$H-NMR (400 MHz, CDCl$_3$)δ(ppm):2.45 (3H, s), 6.11 (1H, d, J=8.0 Hz), 7.19 (1H, d, J=4.0 Hz), 7.35 (1H, d, J=8.0 Hz), 7.80 (1H, d, J=8.0 Hz), 7.92 (1H, s)

Example 1

Synthesis of 2-[3-(1H-imidazol-1-yl)-4-(2-methylpropoxy)phenyl]-4-methyl-1,3-thiazole-5-carboxylic acid (Compound No. 1) (Synthesis Method (A))

(1) A reaction mixture solution prepared by suspending 41.1 mg of 3-fluoro-4-hydroxybenzonitrile, 33.4 mg of isobutyl bromide and 62.2 mg of potassium carbonate in 1 mL of dimethylformamide was heated at 110° C. for 5 hours under a nitrogen atmosphere. After the addition of water to the reaction mixture solution, extraction was performed using ethyl acetate. The organic layer was washed with saline, followed by drying and concentrating under reduced pressure to obtain a crude product of 3-fluoro-4-(2-methylpropoxy) benzonitrile.

(2) A reaction mixture prepared by adding 15.7 mg of sodium hydride and 24.5 mg of imidazole to the crude product of 3-fluoro-4-(2-methylpropoxy)benzonitrile obtained above and suspending the above in 1 mL of dimethylsulfoxide was heated at 110° C. for 5 hours under a nitrogen atmosphere. After the addition of water to the reaction mixture solution, extraction was performed using ethyl acetate. The organic layer was washed with saline, followed by drying and concentrating under reduced pressure to obtain a crude product of 3-(1H-imidazol-1-yl)-4-(2-methylpropoxy)benzonitrile.

ESI/MS m/e: 242.1 (M$^+$+H, $C_{14}H_{16}N_3O$).

(3) A reaction mixture prepared by suspending the crude product of 3-(1H-imidazol-1-yl)-4-(2-methylpropoxy)benzonitrile obtained above in a mixture of 0.2 mL of acetic acid and 0.5 mL of thioacetic acid was heated at 50° C. for 14 hours under a nitrogen atmosphere. Concentration under reduced pressure was prepared to obtain a crude product of 3-(1H-imidazol-1-yl)-4-(2-methylpropoxy)benzene-1-carbothioamide.

ESI/MS m/e: 276.1 (M$^+$+H, $C_{14}H_{18}N_3OS$).

(4) A reaction mixture solution prepared by adding 74.1 mg of ethyl-2-chloroacetacetate to the crude product of 3-(1H-imidazol-1-yl)-4-(2-methylpropoxy)benzene-1-carbothioamide obtained above and suspending the above mixture in 1 mL of ethanol was heated at 80° C. for 5 hours under a nitrogen atmosphere. After the addition of water to the reaction mixture solution, extraction was performed using ethyl acetate. The organic layer was washed with saline, followed by drying and concentrating under reduced pressure to obtain a crude product of 2-[3-(1H-imidazol-1-yl)-4-(2-methylpropoxy)phenyl]-4-methyl-1,3-thiazole-5-carboxylate.

ESI/MS m/e: 386.1 (M$^+$+H, $C_{20}H_{24}N_3O_3S$).

(5) A reaction mixture solution prepared by dissolving the crude product of 2-[3-(1H-imidazol-1-yl)-4-(2-methylpropoxy)phenyl]-4-methyl-1,3-thiazole-5-carboxylate obtained above in 1 mL of a mixed solution of tetrahydrofuran/methanol=1/1 followed by the addition of 0.2 mL of 2 M sodium hydroxide aqueous solution was stirred at room temperature for 4 hours. After the addition of 0.2 mL of 2 M hydrochloric acid to the reaction mixture solution under stirring, 3 mL of water was added and extraction was performed using 4 mL of ethyl acetate. The organic phase was concentrated, followed by purifying by a conventional method to obtain 2.50 mg of 2-[3-(1H-imidazol-1-yl)-4-(2-methylpropoxy)phenyl]-4-methyl-1,3-thiazole-5-carboxylic acid.

$^1$H-NMR (400 MHz, DMSO $d_6$) δ(ppm): 0.89 (6H, d, J=6.4 Hz), 1.96-2.02 (1H, m), 2.65 (3H, s), 3.92 (2H, d, J=6.4 Hz), 7.13 (1H, s), 7.37 (1H, d, J=8.8 Hz), 7.55 (1H, s), 7.95-8.07 (3H, m)

HPLC Retention Time: 8.15 min.
Obs Mass (M$^+$+H): 358.1215
Pred Mass (M$^+$+H): 358.1220
Formula (M): $C_{18}H_{19}N_3O_3S$ Examples 2 to 6

The compounds of Compound Nos. 2 to 6 were synthesized in the similar manner as in Example 1.

Example 7

Synthesis of 2-[3-(1H-imidazol-1-yl)-4-phenoxyphenyl]-4-methyl-1,3-thiazole-5-carboxylic acid (Compound No. 7) (Synthesis Method (A))

(1) A reaction mixture solution prepared by suspending 77.8 mg of 3-chloro-4-fluorobenzonitrile, 51.8 mg of phenol and 82.9 mg of potassium carbonate in 2 mL of dimethylsulfoxide was heated at 100° C. for 14 hours under a nitrogen atmosphere. Subsequently, 24.0 mg of sodium hydroxide and 40.8 mg of imidazole were added to the reaction mixture solution, and the mixture was heated at 140° C. for 5 hours under a nitrogen atmosphere. After the addition of water to the reaction mixture solution, extraction was performed using ethyl acetate. The organic phase is washed with saline, followed by drying and concentrating under reduced pressure. The resulting crude product was separated and purified by silica gel column chromatography to obtain 65.2 mg of 3-(1H-imidazol-1-yl)-4-phenoxybenzonitrile. ESI/MS m/e: 262.2 (M$^+$+H, $C_{16}H_{12}N_3O$).

(2) A reaction mixture prepared by suspending 65.2 mg of 3-(1H-imidazol-1-yl)-4-phenoxybenzonitrile in a mixture of 0.3 mL of acetic acid and 1.0 mL of thioacetic acid was heated at 50° C. for 14 hours under a nitrogen atmosphere. A crude product of 3-(1H-imidazol-1-yl)-4-phenoxybenzene-1-carbothioamide was obtained by concentrating under reduced pressure.

ESI/MS m/e: 296.1 (M$^+$+H, $C_{16}H_{14}N_3OS$).

(3) A reaction mixture solution prepared by adding 123.2 mg of ethyl-2-chlioroacetacetate to the crude product of 3-(1H-imidazol-1-yl)-4-phenoxybenzene-1-carbothioamide obtained above and suspending the mixture in 2 mL of ethanol was heated at 80° C. for 5 hours under a nitrogen atmosphere. After the addition of water to the reaction mixture solution, extraction was performed using ethyl acetate. The organic layer was washed with saline, followed by drying and concentrating under reduced pressure. The resulting crude product was separated and purified by silica gel column chromatography to obtain 72.2 mg of 2-[3-(1H-imidazol-1-yl)-4-phenoxyphenyl]-4-methyl-1,3-thiazole-5-carboxylate.

ESI/MS m/e: 406.1 (M$^+$+H, $C_{22}H_{20}N_3O_3S$).

(4) A reaction mixture solution was prepared by dissolving 20.2 mg of 2-[3-(1H-imidazol-1-yl)-4-phenoxyphenyl]-4-methyl-1,3-thiazole-5-carboxylate obtained above in 1 mL of a mixed solution of tetrahydrofuran/methanol=1/1 and adding 0.2 mL of 2 M sodium hydroxide aqueous solution. The reaction mixture was stirred at 50° C. for 2

| Example | Compound No. | HPLC Retention Time | Obs Mas (M ++ H) | Pred Mass (M ++ H) | Formula(M) | 1HNMR |
|---|---|---|---|---|---|---|
| 2 | 2 | 8.61 | 372.1380 | 372.1376 | C19H21N3O3S | |
| 3 | 3 | 8.39 | 370.1234 | 370.1220 | C19H19N3O3S | 400 MHz (DMSO d6) 1.78-2.03(7H, m), 2.64(3H, s), 4.10(2H, d, J = 6.4 Hz), 7.07(1H, s), 7.36(1H, d, J = 8.8 Hz), 7.53(1H, s), 7.91-7.98(3H, m) |
| 4 | 4 | 8.90 | 384.1376 | 384.1376 | C20H21N3O3S | 400 MHz (DMSO d6) 1.25-1.73(9H, m), 2.64(3H, s), 4.02(2H, d, J = 6.8 Hz), 7.07(1H, s), 7.36(1H, d, J = 8.8 Hz), 7.52(1H, t, J = 1.6 Hz), 7.92(1H, d, J = 2.0 Hz), 797-7.99(2H, m) |
| 5 | 5 | 8.23 | 370.1214 | 370.1220 | C19H19N3O3S | |
| 6 | 6 | 8.71 | 384.1377 | 384.1376 | C20H21N3O3S | 400 MHz (DMSO d6) 1.25-1.57(8H, m), 1.84-1.90(2H, m), 2.65(3H, s), 4.57-4.61(1H, m), 7.07(1H, s), 7.40(1H, d, J = 8.8 Hz), 7.52(1H, s), 7.92-7.99(3H, m) | hours. After the addition of 0.2 mL of 2 M hydrochloric acid to the reaction mixture solution under stirring, 3 mL of water was added and extraction was performed using 4 mL of ethyl acetate. The organic phase was concentrated, followed by purifying using a conventional method to obtain 9.0 mg of 2-[3-(1H-imidazol-1-yl)-4-phenoxyphenyl]-4-methyl-1,3-thiazole-5-carboxylic acid.

$^1$H-NMR (400 MHz, DMSO $d_6$) δ(ppm): 2.61 (3H, s), 7.07-7.13 (3H, m), 7.20 (1H, t, J=6.8 Hz), 7.42 (2H, t, J=8.0 Hz), 7.59 (2H, s), 7.74 (1H, d, J=7.6 Hz), 7.86 (1H, dd, J=1.2, 8.4 Hz), 8.08 (1H, s)

HPLC Retention Time: 7.86 min.
Obs Mass (M$^+$+H): 378.0906
Pred Mass (M$^+$+H): 378.0907
Formula (M): $C_{20}H_{15}N_3O_3S$ Example 8

The compound of Compound No. 8 was synthesized in the similar manner as in Example 7.

| Example | Compound No. | HPLC Retention Time | Obs Mass (M ++ H) | Pred Mass (M ++ H) | Formula(M) | 1HNMR |
|---|---|---|---|---|---|---|
| 8 | 8 | 7.81 | 396.0815 | 396.0813 | C20H14FN3O3S | 400 MHz (DMSO d6) 2.60(3H, s), 7.10(1H, s), 7.24-7.47(4H, m), 7.50(1H, d, J = 1.2 Hz), 7.61(1H, s), 7.75(1H, t, J = 8.4 Hz), 7.85(1H, dd, J = 1.2, 8.0 Hz), 8.09(1H, s) |

Examples 9 to 14

The compounds of Compound Nos. 9 to 14 were synthesized in the similar manner as in Example 1.

| Example | Compound No. | HPLC Retention Time | Obs Mass (M ++ H) | Pred Mass (M ++ M) | Formula(M) | 1HNMR |
|---|---|---|---|---|---|---|
| 9 | 9 | 8.36 | 372.1380 | 372.1376 | C19H21N3O3S | 400 MHz (DMSO d6) 0.83(6H, d, J = 6.8 Hz). 1.86-1.94(1H, m). 2.41(3H, s), 2.65(3H, s), 3.93(2H, d, J = 6.4 Hz), 7.46(1H, d, J = 8.8 Hz), 7.77(1H, d, J = 2.0 Hz), 7.82(1H, d, J = 2.0 Hz), 8.18-8.22(2H, m) |
| 10 | 10 | 11.10 | 374.1272 | 374.1281 | C17H19N5O3S | 400 MHz (DMSO d6) 0.98(6H, d, J = 6.8 Hz), 2.01-2.08(1H, m), 2.39(3H, s), 2.50(3H, s), 3.90(2H, d, J = 6.8 Hz), 7.24(1H, t, J = 8.4 Hz), 7.64(1H, dd, J = 2.0, 7.6 Hz), 7.72(1H, d, J = 8.4 Hz) |
| 11 | 11 | 9.49 | 408.1388 | 408.1376 | C22H21N3O3S | 400 MHz (DMSO d6) 0.72(6H, d, J = 6.8 Hz), 1.45-1.83(1H, m), 2.65(3H, s), 3.89(2H, d, J = 6.4 Hz), 7.25-7.29(3H, m), 7.44(1H, d, J = 8.8 Hz), 7.74-7.76(1H, m), 8.08-8.13(2H, m), 8.40(1H, s), 13.35(1H, s) |
| 12 | 12 | 10.85 | 373.1341 | 373.1329 | C18H20N4O3S | 400 MHz (DMSO d6) 0.95(6H, d, J = 6.4 Hz), 2.04-2.11(1H, m), 2.37(3H, s), 2.65(3H, s), 3.98(2H, d, J = 6.4 Hz), 7.38(1H, d, J = 8.8 Hz), 7.94(1H, dd, J = 2.4, 8.8 Hz), 8.24(1H, d, J = 2.4 Hz), 8.81(1H, s) |
| 13 | 13 | 10.71 | 359.1165 | 359.1172 | C17H18N4O3S | 400 MHz (DMSO d6) 0.93(6H, d, J = 6.8 Hz), 2.01-2.11(1H, m), 2.65(3H, s), 3.98(2H, d, J = 6.8 Hz), 7.41(1H, d, J = 8.8 Hz), 8.00(1H, dd, J = 2.4, 8.8 Hz), 8.23-8.25(2H, m), 8.95(1H, s) |
| 14 | 14 | 9.82 | 373.1335 | 373.1329 | C18H20N4O3S | 400 MHz (DMSO d6) 0.81(6H, d, J = 6.4 Hz), 1.85-1.90(1H, m), 2.25(3H, s), 2.65(3H, s), 3.89(2H, d, J = 6.4 Hz), 7.39(1H, d, J = 8.8 Hz), 7.98-8.02(2H, m), 8.11-8.13(1H, m) |

Example 15

The compound of Compound No. 15 was synthesized in the similar manner as in Example 7.

| Example | Compound No. | HPLC Retention Time | Obs Mass (M ++ H) | Pred Mass (M ++ H) | Formula(M) | 1HNMR |
|---|---|---|---|---|---|---|
| 15 | 15 | 10.51 | 379.0871 | 379.0859 | C19H14N4O3S | 400 MHz (DMSO d6) 2.61(3H, s), 7.16-7.25(3H, m), 7.44(2H, t, J = 7.6 Hz), 7.60(1H, s), 7.92(2H, dd, J = 8.4 Hz), 8.24(1H, s), 9.09(1H, s) |

Example 16

Synthesis of 4-methyl-2-[4-(propan-2-yloxy)-3-(1H-1,2,3-triazol-1-yl)phenyl]-1,3-thiazole-5-carboxylic acid (Compound No. 16) (Synthesis Method (B))

(1) A reaction mixture solution prepared by suspending 2.18 g of 4-bromo-2-nitrophenol and 2.07 g of potassium carbonate in 40 mL of dimethylformamide and adding 2.04 g of isopropyl iodide was heated under stirring at 110° C. for 14 hours under a nitrogen atmosphere. After the addition of water to the reaction mixture solution, extraction was performed using ethyl acetate. The organic layer was washed with saline, followed by drying and concentrating under reduced pressure. The resulting crude product was separated and purified by silica gel column chromatography to obtain 2.08 g of 4-bromo-2-nitro-1-(propan-2-yloxy)benzene.

(2) A suspension was prepared by adding 1.05 g of potassium hydrogen carbonate, 22 mg of palladium chloride (II) and 102 mg of a copper bromide (I) dimethylsulfide complex to 2.08 g of 4-bromo-2-nitro-1-(propan-2-yloxy) benzene obtained above, followed by suspending the mixture in 15 mL of toluene. Subsequently, a reaction mixture solution was prepared by adding 1.02 g of ethyl 4-methyl-1,3-thiazole-5-carboxylate, 46.2 μL of isobutyric acid and 114 mg of di-t-butylcyclohexylphosphine to the suspension was heated at 120° C. for 14 hours under a nitrogen atmosphere. The reaction mixture solution was celite-filtered to remove insoluble matter, water was added to the filtrate, extraction was performed using ethyl acetate. The organic layer was washed with saline and then dried and concentrated under reduced pressure, followed by purifying by a conventional method to obtain 1.38 g of ethyl 4-methyl-2-[3-nitro-4-(propan-2-yloxy)phenyl]-1,3-thiazole-5-carboxylate.

ESI/MS m/e: 351.0 (M$^+$+H, $C_{16}H_{19}N_2O_5S$)

(3) A reaction mixture solution prepared by suspending 1.38 g of ethyl 4-methyl-2-[3-nitro-4-(propan-2-yloxy)phenyl]-1,3-thiazole-5-carboxylate in 15 mL of ethanol and adding 100 mg of palladium/carbon (10 wt %) to the suspension was heated under stirring at 50° C. for 14 hours under a hydrogen atmosphere. The reaction mixture solution was celite-filtered and the filtrate was concentrated under reduced pressure to obtain 1.26 g of ethyl 2-[3-amino-4-(propan-2-yloxy)phenyl]-4-methyl-1,3-thiazole-5-carboxylate.

ESI/MS m/e: 321.1 (M$^+$+H, $C_{16}H_{21}N_2O_3S$).

(4) A reaction solution prepared by suspending 1.26 g of ethyl 2-[3-amino-4-(propan-2-yloxy)phenyl]-4-methyl-1,3-thiazole-5-carboxylate in 10 mL of methanol and adding 1.12 mL of triethylamine to the suspension was cooled to 0° C. Subsequently, a reaction mixture solution was prepared by slowly adding a solution prepared by dissolving 1.01 g of N'-[1E)-2,2-dichloroethylidene]-4-methylbenzene-1-sulfonehydrazine in 10 mL of methanol to the reaction solution, and the mixture was heated at 40° C. for 2 hours under a nitrogen atmosphere. After the addition of water to the reaction mixture solution, extraction was performed using ethyl acetate. The organic layer was washed with saline, followed by drying and concentrating under reduced pressure. The resulting crude product was separated and purified by silica gel column chromatography to obtain 501 mg of ethyl 4-methyl-2-[4-(propan-2-yloxy)-3-(1H-1,2,3-triazol-1-yl)phenyl]-1,3-thiazole-5-carboxylate.

ESI/MS m/e: 373.1 (M$^+$+H, $C_{18}H_{21}N_4O_3S$)

(5) A reaction mixture solution prepared by dissolving 501 mg of ethyl 4-methyl-2-[4-(propan-2-yloxy)-3-(1H-1,2,3-triazol-1-yl)phenyl]-1,3-thiazole-5-carboxylate in 10 mL of a mixed solution of tetrahydrofuran/methanol=1/1 and adding 1.35 mL of 2 M sodium hydroxide aqueous solution was stirred at room temperature for 3 hours. After the addition of 1.35 mL of 2 M hydrochloric acid to the reaction mixture solution under stirring, 8 mL of water was added and extraction was performed using 20 mL of ethyl acetate. The organic phase was concentrated, followed by purifying by a conventional method to obtain 415 mg of 4-methyl-2-[4-(propan-2-yloxy)-3-(1H-1,2,3-triazol-1-yl)phenyl]-1,3-thiazole-5-carboxylic acid.

$^1$H-NMR (400 MHz, DMSO d$_6$) δ(ppm): 1.28 (6H, d, J=5.6 Hz), 2.66 (3H, s), 4.83-4.89 (1H, m), 7.46 (1H, d, J=8.8 Hz), 7.95 (1H, s), 8.06 (1H, dd, J=2.0, 8.8 Hz), 8.22 (1H, dd, J=2.8 Hz), 8.52 (1H, s), 13.39 (1H, s)

HPLC Retention Time: 9.96 min.
Obs Mass (M$^+$+H): 345.1005
Pred Mass (M$^+$+H): 345.1016
Formula (M): $C_{16}H_{16}N_4O_3S$

Examples 17 to 21

The compounds of Compound Nos. 17 to 21 were synthesized in the similar manner as in Example 16.

| Example | Compound No. | HPLC Retention Time | Obs Mass (M ++ H) | Pred Mass (M ++ H) | Fromula(M) | 1HNMR |
|---|---|---|---|---|---|---|
| 17 | 17 | 10.91 | 359.1168 | 359.1172 | C17H18N4O3S | 400 MHz (DMSO d6) 0.88(6H, d, J = 6.8 Hz), 1.95-2.02(1H, m), 2.66(3H, s), 3.95(2H, d, J = 6.4 Hz), 7.44(1H, d, J = 8.8 Hz), 7.97(1H, s), 8.10(1H, dd, J = 2.4, 8.8 Hz), 8.21(1H, d, J = 2.4 Hz), 8.51(1H, d, J = 0.8 Hz), 13.40(1H, s) |
| 18 | 18 | 11.44 | 373.1340 | 373.1329 | C18H20N4O3S | 400 MHz (DMSO d6) 0.87(9H, m), 2.66(3H, s), 3.98(2H, s), 7.44(1H, d, J = 8.8 Hz), 7.98(1H, s), 8.11(1H, dd, J = 2.4, 8.8 Hz), 8.19(1H, d, J = 2.4 Hz), 8.49(1H, s), 13.37(1H, brs) |
| 19 | 19 | 11.29 | 371.1173 | 371.1172 | C18H18N4O3S | 400 MHz (DMSO d6) 1.78-1.99(7H, m), 2.66(3H, s), 4.15(2H, d, J = 6.4 Hz), 7.45(1H, d, J = 8.8 Hz), 7.96(1H, s), 8.10(1H, dd, J = 2.4, 8.8 Hz), 8.24(1H, d, J = 2.0 Hz), 8.49(1H, s), 13.40(1H, brs) |
| 20 | 20 | 9.29 | 331.0847 | 331.0859 | C15H14N4O3S | 400 MHz (DMSO d6) 1.29(6H, d, J = 6.0 Hz), 4.83-4.89(1H, m), 7.49(1H, d, J = 8.8 Hz), 7.95(1H, d, J = 0.8 Hz), 8.11(1H, dd, J = 2.8, 8.8 Hz), 8.25(1H, d, J = 2.4 Hz), 8.39(1H, d, J = 2.0 Hz), 8.52(1H, d, J = 1.2 Hz), 13.58(1H, brs) |

| Example | Compound No. | HPLC Retention Time | Obs Mass (M ++ H) | Pred Mass (M ++ H) | Fromula(M) | 1HNMR |
|---|---|---|---|---|---|---|
| 21 | 21 | 10.26 | 345.1011 | 345.1016 | C16H16N4O3S | 400 MHz (DMSO d6) 0.88(6H, d, J = 6.8 Hz), 1.95-2.02(1H, m), 3.96(2H, d, J = 6.0 Hz), 7.45(1H, d, J = 8.8 Hz), 7.96(1H, d, J = 0.8 Hz), 8.14(1H, dd, J = 2.4, 8.8 Hz), 8.23(1H, d, J = 2.4 Hz), 8.39(1H, s), 8.50(1H, d, J = 0.8 Hz), 13.59(1H, brs) |

Examples 22 and 23

The compounds of Compound Nos. 22 and 23 were synthesized in the similar manner as in Example 7.

| Example | Compound No. | HPLC Retention Time | Obs Mass (M ++ H) | Pred Mass (M ++ H) | Formula(M) | 1HNMR |
|---|---|---|---|---|---|---|
| 22 | 22 | 10.68 | 379.0851 | 379.0859 | C19H14N4O3S | 400 MHz (DMSO d6) 2.62(3H, s), 7.15(2H, d, J = 7.6 Hz), 7.21-7.25(1H, m), 7.44(2H, t, J = 8.0 Hz), 7.62(1H, d, J = 0.8 Hz), 7.91-7.98(3H, m), 8.64(1H, s), 13.50(1H, brs) |
| 23 | 23 | 10.63 | 397.0777 | 397.0765 | C19H13N4O3S | 400 MHz (DMDO d6) 2.62(3H, s), 7.26-7.47(4H, m), 7.54(1H, s), 7.91-7.98(3H, m), 8.64(1H, d, J = 0.8 Hz), 13.50(1H, brs) |

Example 24

Synthesis of 4-methyl-2-[4-(propan-2-yloxy)-3-(1H-1,2,3,4-tetrazol-1-yl)phenyl]-1,3-thiazole-5-carboxylic acid (Compound No. 24) (Synthesis Method (C))

(1) A suspension was prepared by suspending 1.23 g of ethyl 2-[3-amino-4-(propan-2-yloxy)phenyl]-4-methyl-1,3-thiazole-5-carboxylate in 20 mL of acetic acid. A reaction mixture solution prepared by adding 478 mg of sodium azide and 1.09 g of triethyl ortho formate to the suspension was heated at 70° C. for 2 hours under a nitrogen atmosphere. After cooling the reaction mixture solution to room temperature, water was added to the reaction mixture solution, and extraction was performed using ethyl acetate. The organic layer was washed with saline, dried and concentrated under reduced pressure and purified by a conventional method to obtain 1.13 g of ethyl 4-methyl-2-[4-(propan-2-yloxy)-3-(1H-1,2,3,4-tetrazol-1-yl)phenyl]-1,3-thiazole-5-carboxylate.

ESI/MS m/e: 374.1 (M$^+$+H, $C_{17}H_{20}N_5O_3S$)

(2) A reaction mixture solution prepared by dissolving 1.13 g of ethyl 4-methyl-2-[4-(propan-2-yloxy)-3-(1H-1,2,3,4-tetrazol-1-yl)phenyl]-1,3-thiazole-5-carboxylate in 15 mL of a mixed solution of tetrahydrofuran/methanol=1/1 and adding 3.0 mL of 2 M sodium hydroxide aqueous solution to the mixture was stirred at room temperature for 3 hours. After the addition of 3.0 mL of 2 M hydrochloric acid to the reaction solution under stirring, 7 mL of water was added and extraction was performed using 30 mL of ethyl acetate. The organic layer was concentrated, followed by purifying by a conventional method to obtain 920 mg of 4-methyl-2-[4-(propan-2-yloxy)-3-(1H-1,2,3,4-tetrazol-1-yl)phenyl]-1,3-thiazole-5-carboxylic acid.

$^1$H-NMR (400 MHz, DMSO $d_6$) δ(ppm): 1.28 (6H, d, J=6.0 Hz), 2.65 (3H, s), 4.84-4.90 (1H, m), 7.50 (1H, d, J=9.6 Hz), 8.13 (1H, dd, J=2.4, 8.8 Hz), 8.27 (1H, d, J=2.4 Hz), 9.79 (1H, s), 13.41 (1H, s)

HPLC Retention Time: 9.99 min.
Obs Mass (M$^+$+H): 346.0958
Pred Mass (M$^+$+H): 346.0968
Formula (M): $C_{15}H_{15}N_6O_3S$ Examples 25 to 30

The compounds of compound Nos. 25 to 28 were synthesized in the similar manner as in Example 24.

| Example | Compound No. | HPLC Retention Time | Obs Mass (M ++ H) | Pred Mass (M ++ H) | Formula(M) | 1HNMR |
|---|---|---|---|---|---|---|
| 25 | 25 | 10.87 | 360.1124 | 360.1125 | C16H17N5O3S | 400 MHz (DMSO d6) 0.85(6H, d, J = 6.8 Hz), 1.93-2.00(1H, m), 2.66(3H, s), 3.96(2H, d, J = 6.0 Hz), 7.48(1H, d, J = 8.8 Hz), 8.18(1H, dd, J = 2.4, 8.8 Hz), 8.27(1H, d, J = 2.4 Hz), 9.79(1H, s), 13.41(1H, s) |
| 26 | 26 | 11.35 | 374.1287 | 374.1281 | C17H19N5O3S | 400 MHz (DMSO d6) 0.83(9H, s), 2.66(3H, s), 3.83(2H, s), 7.47(1H, d, J = 8.8 Hz), 8.18(1H, dd, J = 2.4, 8.8 Hz), 8.27(1H, d, J = 2.0 Hz), 9.78(1H, s), 13.40(1H, s) |
| 27 | 27 | 11.22 | 372.1104 | 372.1125 | C17H17N5O3S | 400 MHz (DMSO d6) 1.72-1.97(7H, m), 2.66(3H, s), 4.16(2H, d, J = 6.4 Hz), 7.48(1H, d, J = 9.2 Hz), 8.16(1H, dd, J = 2.4, 8.8 Hz), 8.28(1H, d, J = 2.4 Hz), 9.75(1H, s), 13.38(1H, s) |

| Example | Compound No. | HPLC Retention Time | Obs Mass (M ++ H) | Pred Mass (M ++ H) | Formula(M) | 1HNMR |
|---|---|---|---|---|---|---|
| 28 | 28 | 10.99 | 372.1114 | 372.1125 | C17H17N5O3S | 400 MHz (DMSO d6) 1.53-1.57(4H, m), 1.66-1.73(2H, m), 1.88-1.93(2H, m), 2.65(3H, s), 5.06-5.10(1H, m), 7.47(1H, d, J = 8.8 Hz), 8.14(1H, dd, J = 2.4, 8.8 Hz), 8.46(1H, d, J = 2.4 Hz), 9.74(1H, s) |

Example 29

Synthesis of 2-[4-(3-hydroxy-2-methylpropoxy)-3-(1H-1,2,3,4-tetrazol-1-yl)phenyl]-4-methyl-1,3-thiazole-5-carboxylic acid (Compound No. 29) (Synthesis Method (C))

(1) In the similar manner as in Examples 16 and 24, 1.97 g of ethyl [4-(methoxymethoxy)-3-(1H-1,2,3,4-tetrazol-1-yl)phenyl]-4-methyl-1,3-thiazole-5-carboxylate was obtained from 4.36 g of 4-bromo-2-nitrophenol.

ESI/MS m/e: 376.0 (M$^+$+H, C$_{16}$H$_{18}$N$_5$O$_4$S)

$^1$H-NMR (400 MHz, DMC13) δ(ppm): 1.40 (6H, d, J=7.2 Hz), 2.78 (3H, s), 3.48 (3H, s), 4.36 (2H, q, J=6.8 Hz), 5.34 (2H, s), 7.45 (1H, d, J=8.8 Hz), 8.05 (1H, dd, J=2.4, 8.8 Hz), 8.44 (1H, d, J=2.4 Hz), 9.17 (1H, s)

(2) A reaction mixture solution was prepared by dissolving 1.97 g of ethyl [4-(methoxymethoxy)-3-(1H-1,2,3,4-tetrazol-1-yl)phenyl]-4-methyl-1,3-thiazole-5-carboxylate in 25 mL of 1,4-dioxane and adding 5.0 mL of 2 M hydrochloric acid was heated under stirring at 60° C. for 8 hours. After the reaction mixture solution was cooled to room temperature, the precipitated solid was filtered to obtain 1.49 g of ethyl 2-[4-hydroxy-3-(1H-1,2,3,4-tetrazol-1-yl)phenyl]-4-methyl-1,3-thiazole-5-carboxylate.

ESI/MS m/e: 332.0 (M$^+$+H, C$_{14}$H$_{14}$N$_5$O$_3$S)

$^1$H-NMR (400 MHz, DMSO d$_6$) δ(ppm): 1.39 (6H, d, J=7.2 Hz), 2.76 (3H, s), 4.35 (2H, q, J=7.2 Hz), 7.22 (1H, d, J=8.4 Hz), 7.39 (1H, s), 7.90 (1H, dd, J=2.4, 8.8 Hz), 8.45 (1H, d, J=2.8 Hz), 9.44 (1H, s)

(3) A solution was prepared by dissolving 13.5 mg of 2-methypropan-1,3-diol in 1 mL of tetrahydrofuran and adding 39.3 mg of triphenylphosphine and 65 µL of a 40% toluene solution of diethyl azodicarboxylate to the mixture. After stirring the resultant solution at room temperature for 30 minutes, a reaction mixture solution prepared by adding 33.1 mg of ethyl 2-[4-hydroxy-3-(1H-1,2,3,4-tetrazol-1-yl)phenyl]-4-methyl-1,3-thiazole-5-carboxylate to the solution was stirred at room temperature for 3 hours. After the addition of water to the reaction mixture solution, extraction was performed using ethyl acetate. The organic layer was washed with saline and then dried and concentrated under reduced pressure, followed by purifying by a conventional method to obtain 67.7 mg of ethyl 2-[4-(3-hydroxy-2-methylpropoxy)-3-(1H-1,2,3,4-tetrazol-1-yl)phenyl]-4-methyl-1,3-thiazole-5-carboxylate.

ESI/MS m/e: 404.1 (M$^+$+H, C$_{18}$H$_{22}$N$_5$O$_4$S)

(4) A solution was prepared by dissolving 34.1 mg of ethyl 2-[4-(3-hydroxy-2-methylpropoxy)-3-(1H-1,2,3,4-tetrazol-1-yl)phenyl]-4-methyl-1,3-thiazole-5-carboxylate in 1.0 mL of a mixed solution of tetrahydrofuran/methanol=1/1. A reaction mixture solution prepared by adding 0.2 mL of 2 M sodium hydroxide aqueous solution to the solution was stirred at room temperature for 3 hours. After the addition of 0.2 mL of 2 M hydrochloric acid to the reaction mixture solution under stirring, 3 mL of water was added and extraction was performed using 4 mL of ethyl acetate. The organic layer was concentrated, followed by purifying by a conventional method to obtain 15.4 mg of 2-[4-(3-hydroxy-2-methylpropoxy)-3-(1H-1,2,3,4-tetrazol-1-yl)phenyl]-4-methyl-1,3-thiazole-5-carboxylic acid.

$^1$H-NMR (400 MHz, DMSO d$_6$) δ(ppm): 0.82 (3H, d, J=6.8 Hz), 1.90-1.98 (1H, m), 2.66 (3H, s), 3.25-3.28 (2H, m), 4.04-4.15 (2H, m), 4.62 (1H, m), 7.48 (1H, d, J=8.8 Hz), 8.17 (1H, dd, J=2.0, 8.8 Hz), 8.28 (1H, d, J=2.0 Hz), 9.80 (1H, s), 13.37 (1H, brs)

HPLC Retention Time: 8.23 min.
Obs Mass (M$^+$+H): 376.1074
Pred Mass (M$^+$+H): 376.1074
Formula (M): C$_{16}$H$_{17}$N$_5$O$_4$S Example 30

Synthesis of 2-[4-(2-hydroxy-2-methylpropoxy)-3-(1H-1,2,3,4-tetrazol-1-yl)phenyl]-4-methyl-1,3-thiazole-5-carboxylic acid (Compound No. 30) (Synthesis Method (C))

(1) A solution was prepared by dissolving 33.1 mg of ethyl 2-[4-hydroxy-3-(1H-1,2,3,4-tetrazol-1-yl)phenyl]-4-methyl-1,3-thiazole-5-carboxylate in 1.0 mL of dimethylformamide. A reaction mixture solution prepared by adding 20.7 mg of potassium carbonate and 16.2 mg of 3-bromo-2-methylpropene to the solution was heated under stirring at 100° C. for 4 hours. The reaction mixture solution was cooled to room temperature and then 3 mL of water and 4 mL of ethyl acetate were added under stirring, followed by concentrating the organic phase to obtain 34.1 mg of ethyl 4-methyl-2-{4-[(2-methylpropen-1-yl)oxy]-3-(1H-1,2,3,4-tetrazol-1-yl)phenyl}-1,3-thiazole-5-carboxylate.

(2) A reaction mixture solution prepared by adding 1.0 mL of 35% sulfuric acid aqueous solution to 34.1 mg of ethyl 4-methyl-2-{4-[(2-methylpropen-1-yl)oxy]-3-(1H-1,2,3,4-tetrazol-1-yl)phenyl}-1,3-thiazole-5-carboxylate was heated under stirring at 80° C. for 4 hours. The reaction mixture solution was cooled to room temperature and then 3 mL of water and 4 mL of ethyl acetate were added under stirring, and the organic phase was concentrated and purified using a conventional method to obtain 9.9 mg of ethyl 2-[4-(2-hydroxy-2-methylpropoxy)-3-(1H-1,2,3,4-tetrazol-1-yl)phenyl]-4-methyl-1,3-thiazole-5-carboxylate.

ESI/MS m/e: 404.1 (M$^+$+H, C$_{18}$H$_{22}$N$_5$O$_4$S)

(3) A reaction mixture solution prepared by dissolving 9.9 mg of ethyl 2-[4-(2-hydroxy-2-methylpropoxy)-3-(1H-1,2,3,4-tetrazol-1-yl)phenyl]-4-methyl-1,3-thiazole-5-carboxylate in 1.0 mL of a mixed solution of tetrahydrofuran/methanol=1/1 and adding 0.2 mL of 2 M sodium hydroxide aqueous solution was stirred at room temperature for 3 hours. After the addition of 0.2 mL of 2 M hydrochloric acid to the reaction mixture solution under stirring, 3 mL of water was added and extraction was performed using 4 mL of ethyl acetate. The organic phase was concentrated and purified by a conventional method to obtain 4.8 mg of 2-[4-(2-hydroxy-2-methylpropoxy)-3-(1H-1,2,3,4-tetrazol-1-yl)phenyl]-4-methyl-1,3-thiazole-5-carboxylic acid.

$^1$H-NMR (400 MHz, DMSO d$_6$) δ(ppm): 1.08 (6H, s), 2.66 (3H, s), 3.96 (2H, s), 4.80 (1H, s), 7.50 (1H, d, J=8.8 Hz), 8.15 (1H, dd, J=2.8, 8.8 Hz), 8.31 (1H, d, J=2.4 Hz), 9.90 (1H, s), 13.44 (1H, brs)

HPLC Retention Time: 8.29 min.

Obs Mass (M$^+$+H): 376.1073

Pred Mass (M$^+$+H): 376.1074

Formula (M): C$_{16}$H$_{17}$N$_5$O$_4$S

Examples 31 and 32

The compounds of compound Nos. 31 and 32 were synthesized in the similar manner as in Example 24.

thiazole-5-carboxylate, 339 mg of phenol and 622 mg of potassium carbonate in 15 mL of dimethylformamide was heated at 100° C. for 14 hours under a nitrogen atmosphere. The reaction mixture solution was cooled to room temperature, water was added and extraction was performed using ethyl acetate. The organic layer was washed with saline and then dried and concentrated under reduced pressure. The resulting crude product was separated and purified by silica gel column chromatography to obtain 1.14 g of ethyl 2-(3-nitro-4-phenoxyphenyl)-4-methyl-1,3-thiazole-5-carboxylate.

ESI/MS m/e: 385.0 (M$^+$+H, C$_{19}$H$_{17}$N$_2$O$_5$S)

(3) A reaction mixture solution prepared by suspending 1.14 g of ethyl 2-(3-nitro-4-phenoxyphenyl)-4-methyl-1,3-thiazole-5-carboxylate in 15 mL of ethanol and adding 300 mg of palladium/carbon (10 wt %) was stirred at room

| Example | Compound No. | HPLC Retention Time | Obs Mass (M ++ H) | Pred Mass (M ++ H) | Formula(M) | 1HNMR |
|---|---|---|---|---|---|---|
| 31 | 31 | 9.32 | 332.0824 | 332.0812 | C14H13N5O3S | 400 MHz (DMSO d6) 1.28(6H, d, J = 6.0 Hz), 4.85-4.91(1H, m), 7.53(1H, d, J = 8.8 Hz), 8.18(1H, dd, J = 2.0, 8.8 Hz), 8.27(1H, d, J = 2.0 Hz), 8.39(1H, s), 9.80(1H, s), 13.60(1H, brs) |
| 32 | 32 | 10.23 | 346.0951 | 346.0968 | C15H15N5O3S | 400 MHz (DMSO d6) 0.85(6H, d, J = 6.8 H), 1.93-2.01(1H, m), 3.96(2H, d, J = 6.4 Hz), 7.49(1H, d, J = 9.2 Hz), 8.20(1H, dd, J = 2.4, 8.8 Hz), 8.30(1H, d, J = 2.4 Hz), 8.40(1H, s), 9.78(1H, s), 13.59(1H, brs) |

Example 33

Synthesis of 4-methyl-2-[4-phenoxy-3-(1H-1,2,3,4-tetrazol-1-yl)phenyl]-1,3-thiazole-5-carboxylic acid (Compound No. 33) (Synthesis Method (C))

(1) A mixture was prepared by adding 2.10 g of potassium hydrogen carbonate, 44 mg of palladium chloride (II) and 205 mg of a copper bromide (I) dimethylsulfide complex to 2.20 g of 5-bromo-2-fluoronitrobenzene and the resulting mixture was suspended in 20 mL of toluene. Subsequently, a reaction mixture solution prepared by adding 2.05 g of ethyl 4-methyl-1,3-thiazole-5-carboxylate, 92.5 μL of isobutyric acid and 228 mg of di-t-butylcyclohexylphosphine to the resulting suspension was heated at 120° C. for 14 hours under a nitrogen atmosphere. The reaction mixture solution was celite-filtered to remove insoluble matter and water was added to the filtrate, and extraction was performed using ethyl acetate. The organic layer was washed with saline and dried and concentrated under reduced pressure. The resulting crude product was separated and purified by silica gel column chromatography to obtain 2.28 g of ethyl 2-(4-fluoro-3-nitrophenyl)-4-methyl-1,3-thiazole-5-carboxylate.

ESI/MS m/e: 311.0 (M$^+$+H, C$_{13}$H$_{12}$FN$_2$O$_4$S)

(2) A reaction mixture solution prepared by suspending 931 mg of ethyl 2-(4-fluoro-3-nitrophenyl)-4-methyl-1,3- temperature for 14 hours under a hydrogen atmosphere. The reaction mixture solution was celite-filtered and the filtrate was concentrated under reduced pressure to obtain 1.05 g of ethyl 2-(3-amino-4-phenoxyphenyl)-4-methyl-1,3-thiazole-5-carboxylate.

ESI/MS m/e: 355.1 (M$^+$+H, C$_{19}$H$_{19}$N$_2$O$_3$S)

(4) In the similar manner as in Example 24, 458 mg of 4-methyl-2-[4-phenoxy-3-(1H-1,2,3,4-tetrazol-1-yl)phenyl]-1,3-thiazole-5-carboxylic acid was obtained using 1.05 g of ethyl 2-(3-amino-4-phenoxyphenyl)-4-methyl-1,3-thiazole-5-carboxylate.

$^1$H-NMR (400 MHz, DMSO d$_6$) δ(ppm): 2.67 (3H, s), 7.11-7.29 (4H, m), 7.43-7.48 (2H, m), 8.15 (1H, dd, J=2.4, 8.8 Hz), 8.42 (1H, d, J=2.0 Hz), 9.97 (1H, s), HPLC Retention Time: 10.79 min.

Obs Mass (M$^+$+H): 380.0803

Pred Mass (M$^+$+H): 380.0812

Formula (M): C$_{18}$H$_{13}$N$_5$O$_3$S

Examples 34 to 48

The compounds of Compound Nos. 34 to 48 were synthesized in the similar manner as in Example 33.

| Example | Compound No. | HPLC Retention Time | Obs Mass (M ++ H) | Pred Mass (M ++ H) | Formula(M) | 1HNMR |
|---|---|---|---|---|---|---|
| 34 | 34 | 10.67 | 398.0722 | 398.0718 | C18H12FN5O3S | 400 MHz (DMSO d6) 2.67(3H, s, 7.11(1H, d, J = 8.8 Hz), 7.30-7.48(4H, m), 8.16(1H, dd, J = 2.4, 8.8 Hz), 8.44(1H, d, J = 2.4 Hz), 9.99(1H, s) |
| 35 | 35 | 10.80 | 410.0908 | 410.0918 | C19H15N5O4S | 400 MHz (DMSO d6) 2.68(3H, s), 3.71(3H, s), 6.90(1H, d, J = 8.8 Hz), 7.03-7.31 (4H, m), 8.10(1H, dd, J = 2.4, 8.8 Hz), 8.38(1H, d, J = 2.8 Hz), 9.94(1H, s) |

| Example | Compound No. | HPLC Retention Time | Obs Mass (M ++ H) | Pred Mass (M ++ H) | Formula(M) | 1HNMR |
|---|---|---|---|---|---|---|
| 36 | 36 | 10.63 | 416.0620 | 416.0623 | C18H11F2N5O3S | 400 MHz (DMSO d6) 2.66(3H, s), 7.18(1H, d, J = 8.8 Hz), 7.35-7.45 (3H, m), 8.18(1H, dd, J = 2.0, 8.8 Hz), 8.43(1H, d, J = 2.4 Hz), 10.00(1H, s) |
| 37 | 37 | 10.87 | 398.0717 | 398.0718 | C18H12FN5O3S | 300 MHz (DMSO d6) 02.68(3H, s), 7.02-7.18 (3H, m), 7.27(1H, d, J = 8.7 Hz), 7.50(1H, q, J = 8.1 Hz), 8.18(1H, dd, J = 2.1, 8.7 Hz), 8.43(1H, d, J = 2.1 Hz), 9.98(1H, s) |
| 38 | 38 | 11.49 | 394.0958 | 394.0968 | C19H15N5O3S | 300 MHZ (DMSO d6) 2.31(3H, s), 2.68(3H, s), 6.97-7.16 (4H, m), 7.32-7.37(1H, m), 8.16(1H, dd, J = 2.7, 9.0 Hz), 8.41(1H, d, J = 2.1 Hz), 9.98(1H, s) |
| 39 | 39 | 11.17 | 414.0421 | 414.0422 | C18H12ClN5O3S | 300 MHz (DMSO d6) 2.68(3H, s), 7.02(1H, d, J = 8.7 Hz), 7.14-7.81 (4H, m), 8.18(1H, dJ = 8.4 Hz), 8.46(1H, s), 9.98(1H, s), 13.37(1H, brs) |
| 40 | 40 | 11.56 | 412.0884 | 412.0874 | C19H14FN5O3S | 300 MHz (DMSO d6) 2.23(3H, s), 2.68(3H, s), 7.07-7.28 (4H, m), 8.15(1H, dd, J = 2.7, 8.7 Hz), 8.42(1H, d, J = 2.1 Hz), 9.99(1H, s) |
| 41 | 41 | 11.39 | 412.0873 | 412.0874 | C19H14FN5O3S | 300 MHz (DMSO d6) 2.21(3H, s), 2.68(3H, s), 6.92(1H, d, J = 8.7 Hz), 7.15-7.30 (3H, m), 8.13(1H, dd, J = 2.1, 9.0 Hz), 8.42(1H, d, J = 2.1 Hz), 10.00(1H, s) |
| 42 | 42 | 10.83 | 416.0607 | 416.0623 | C18H11F2N5O3S | 300 MHz (DMSO d6) 2.68(3H, s), 7.13-7.61 (4H, m), 8.15(1H, dd, J = 2.1, 9.0 Hz), 8.44(1H, d, J = 2.1 Hz), 10.01(1H, s) |
| 43 | 43 | 10.80 | 428.0819 | 428.0823 | C19H14FN5O4S | 300 MHz (DMSO d6) 2.67(3H, s), 3.77(3H, s), 6.97-7.10 (3H, m), 7.32-7.40(1H, m), 8.10(1H, dd, J = 2.1, 8.7 Hz), 8.40(1H, d, J = 2.1 Hz), 9.92(1H, s) |
| 44 | 44 | 11.36 | 394.0973 | 394.0968 | C19H15N5O3S | 300 MHz (DMSO d6) 2.12(3H, s), 2.65(3H, s), 6.91(1H, d, J = 8.7 Hz), 7.11-7.38 (4H, m), 8.10(1H, dd, J = 2.1, 9.0 Hz), 8.39(1H,d, J = 2.1 Hz), 9.98(1H, s) |
| 45 | 45 | 11.54 | 394.0963 | 394.0968 | C19H15N5O3S | 300 MHz (DMSO d6) 2.11(3H, s), 2.66(3H, s), 7.07-7.28 (5H, m), 8.11(1H, dd, J = 2.1, 8.7 Hz), 8.37(1H, d, J = 2.1 Hz), 9.98(1H, s) |
| 46 | 46 | 11.58 | 412.0876 | 412.0874 | C19H14FN5O3S | 300 MHz (DMSO d6) 2.31(3H, s), 2.67(3H, s), 6.86-6.97 (3H, m), 7.27(1H, d, J = 9.0 Hz), 8.16(1H, dd, J = 2.1, 8.7 Hz), 8.41(1H, d, J = 2.1 Hz), 9.92(1H, s) |
| 47 | 47 | 10.76 | 416.0629 | 416.0623 | C18H11F2N5O3S | 300 MHz (DMSO d6) 2.67(3H, s), 7.07-7.40 (4H, m), 8.11(1H, dd, J = 2.4, 8.7 Hz), 8.44(1H, d, J = 2.1 Hz), 9.71(1H, s) |
| 48 | 48 | 11.36 | 412.0871 | 412.0874 | C19H14FN5O3S | 300 MHz (DMSO d6) 2.30(3H, s), 2.68(3H, s), 7.11-7.36 (4H, m), 8.16(1H, dd, J = 2.1, 8.7 Hz), 8.44(1H, d, J = 2.1 Hz), 9.99(1H, s) |

Example 49

Synthesis of 4-methl-2-{4-[(2-methylpropyl)sulfanyl]-3-(1H-1,2,3,4-tetrazol-1-yl)phenyl}-1,3-thiazole-5-carboxylic acid (Compound No. 49) (Synthesis Method (D))

(1) A reaction mixture solution prepared by suspending 155.2 mg of ethyl 2-[4-fluoro-3-nitrophenyl]-4-methyl-1,3-thiazole-5-carboxylate and 244.4 mg of cesium carbonate in 1.5 mL of N,N-dimethylformamide and adding 49.6 mg of 2-methylpropylthiol was heated under stirring at 80° C. for 5 hours under a nitrogen atmosphere. The reaction mixture solution was cooled to room temperature, 3 mL of water was added and extraction was performed using ethyl acetate. The organic layer was concentrated under reduced pressure to obtain a crude product of ethyl 2-[4-(2-methylpropylthio)-3-nitropheny]-4-methyl-1,3-thiazole-5-carboxylate.

(2) The crude product of ethyl 2-[4-(2-methylpropylthio)-3-nitropheny]-4-methyl-1,3-thiazole-5-carboxylate obtained above was reduced using palladium carbon under a hydrogen atmosphere to obtain ethyl 2-[3-amino-4-(2-methylpropylthio)phenyl]-4-methyl-1,3-thiazole-5-carboxylate.

(3) A reaction mixture solution prepared by suspending ethyl 2-[3-amino-4-(2-methylpropylthio)phenyl]-4-methyl-1,3-thiazole-5-carboxylate obtained above in 2.0 mL of acetic acid and adding 65 mg of sodium azide and 148 mg of triethyl ortho formate was heated at 70° C. for 5 hours under a nitrogen atmosphere. The reaction mixture solution was cooled to room temperature, water was added and extraction was performed using ethyl acetate. The organic layer was washed with saline and then dried and concentrated under reduce pressure, followed by purifying by a conventional method to obtain 123 mg of ethyl 4-methyl-2-{4-[(2-methylpropyl)sulfanyl]-3-(1H-1,2,3,4-tetrazol-1-yl)phenyl}-1,3-thiazole-5-carboxylate.

(4) A reaction mixture solution prepared by adding 123 mg of ethyl 4-methyl-2-{4-[(2-methylpropyl)sulfanyl]-3-(1H-1,2,3,4-tetrazol-1-yl)phenyl}-1,3-thiazole-5-carboxylate to 2 mL of a mixed solution of terahydrofuran/methanol=1/1 and adding 0.5 mL of 2 M sodium hydroxide aqueous solution was stirred at room temperature for 3 hours. After the addition of 0.5 mL of 2 M hydrochloric acid to the reaction mixture solution under stirring, 3 mL of water was added and extraction was performed using ethyl acetate. The organic phase was concentrated, followed by purifying by a conventional method to obtain 67.9 mg of 4-methyl-2-{4-[(2-methylpropyl)sulfanyl]-3-(1H-1,2,3,4-tetrazol-1-yl)phenyl}-1,3-thiazole-5-carbxylic acid.

$^1$H-NMR (400 MHz, DMSO d$_6$) δ(ppm): 0.91 (6H, d, J=8.0 Hz), 1.75 (1H, septet, J=8.0 Hz), 2.66 (3H, s), 2.93 (2H, d, J=8.0 Hz), 7.78 (1H, d, J=8.0 Hz), 8.17-8.19 (2H, m), 9.89 (1H, s), 13.48 (1H, brs)

HPLC Retention Time: 11.19 min.
Obs Mass (M$^+$+H): 376.0887
Pred Mass (M$^+$+H): 376.0896
Formula (M): $C_{16}H_{17}N_5O_2S_2$ Examples 50 and 51

The compounds of Compound Nos. 50 and 51 were synthesized in the similar manner as in Example 49.

Water was added to the reaction mixture solution and extraction was performed using ethyl acetate. The organic layer was concentrated under reduced pressure and then the resulting crude product was separated and purified by silica gel column chromatography to obtain 256.1 mg of ethyl 2-[4-(N,N-diethylamino)-3-nitrophenyl]-4-methyl-1,3-thiazole-5-carboxylate.

(3) Ethyl 2-[4-(N,N-diethylamino)-3-nitrophenyl]-4-methyl-1,3-thiazole-5-carboxylate obtained above was reduced by palladium carbon under a hydrogen atmosphere to obtain ethyl 2-[3-amino-4-(N,N-diethylamino) phenyl]-4-methyl-1,3-thiazole-5-carboxylate.

(4) A reaction mixture solution prepared by suspending ethyl 2-[3-amino-4-(N,N-diethylamino)phenyl]-4-methyl-1,3-thiazole-5-carboxylate obtained above in 3.0 mL of acetic acid and adding 91.6 mg of sodium azide and 209.2 mg of triethyl ortho formate was heated at 70° C. for 5 hours under a nitrogen atmosphere. The reaction mixture solution was cooled to room temperature, water and a saturated sodium hydrogen carbonate aqueous solution were added, and extraction was performed using ethyl acetate. The organic layer was washed with saline and then dried and concentrated under reduced pressure, followed by purifying by a

| Example | Compound No. | HPLC Retention Time | Obs Mass (M ++ H) | Pred Mass (M ++ H) | Formula(M) | 1HNMR |
|---|---|---|---|---|---|---|
| 50 | 50 | 10.45 | 362.0736 | 362.0740 | C15H15N5O2S2 | 400 MHz (DMSO d6) 1.15(6H, d, J = 6.8 Hz), 2.62(3H, s), 3.56-3.63(1H, m), 7.80(1H, d, J = 8.4 Hz), 8.14-8.18(2H, m), 9.82(1H, s) |
| 51 | 51 | 11.83 | 410.0730 | 410.0740 | C19H15N5O2S2 | 400 MHz (DMSO d6) 2.33(3H, s), 2.65(3H, s), 7.18-7.37 (5H, m), 8.10(1H, d, J = 8.8 Hz), 8.26(1H, s), 9.96(1H, s), 13.49(1H, brs) |

Example 52

Synthesis of 4-methyl-2-[4-(N,N-diethylamino)-3-(1H-1,2,3,4-tetrazol-1-yl)phenyl]-1,3-thiazole-5-carboxylic acid (Compound No. 52)

(1) A reaction mixture solution prepared by suspending 220 mg of 5-bromo-2-fluoronitrobenzene and 276 mg of potassium carbonate in 2 mL of N,N-dimethylformamide and adding 88 mg of N,N-diethylamine was heated under stirring at 40° C. for 14 hours under a nitrogen atmosphere. The reaction mixture solution was cooled to room temperature, 3 mL of water was added and extraction was performed using ethyl acetate. The organic layer was concentrated under reduced pressure to obtain a crude product of 5-bromo-2-(N,N-diethylamino)nitrobenzene.

(2) A suspension was prepared by adding 210.3 mg of potassium hydrogen carbonate, 5.3 mg of palladium chloride (II), 49.3 mg of a copper bromide (I) dimethylsulfide complex and 21.5 mg of 2-(di-t-butylphosphino)biphenyl to the crude product of 5-bromo-2-(N,N-diethylamino) nitrobenzene obtained above, followed by suspending the mixture in 2 mL of toluene. A reaction mixture solution prepared by adding 188.3 mg of ethyl 4-methyl-1,3-thiazole-5-carboxylate and 10.6 mg of isobutyric acid to the suspension was heated at 130° C. for 13 hours under a nitrogen atmosphere.

conventional method to obtain 295.9 mg of ethyl 2-[4-(N,N-diethylamino)-3-(1H-1,2,3,4-tetrazol-1-yl)phenyl]-1,3-thiazole-5-carboxylate.

(5) A reaction mixture solution prepared by dissolving 295.9 mg of ethyl 2-[4-(N,N-diethylamino)-3-(1H-1,2,3,4-tetrazol-1-yl)phenyl]-1,3-thiazole-5-carboxylate obtained above in 3 mL of a mixed solution of tetrahydrofuran/methanol=1/1 and adding 2.0 mL of 2 M sodium hydroxide aqueous solution was stirred at room temperature for 2 hours. After the addition of 2.0 mL of 2 M hydrochloric acid to the reaction mixture solution, the mixture was purified by a conventional method to obtain 199.9 mg of 4-methyl-2-[4-(N,N-diethylamino)-3-(1H-1,2,3,4-tetrazol-1-yl)phenyl]-1,3-thiazole-5-carboxylic acid.

$^1$H-NMR (400 MHz, DMSO d$_6$) δ(ppm): 0.85 (6H, d, J=8.0 Hz), 2.64 (3H, s), 2.80 (4H, d, J=8.0 Hz), 7.41 (1H, d, J=8.0 Hz), 8.02 (1H, d, J=4.0 Hz), 8.08 (1H, dd, J=8.0, 4.0 Hz), 9.82 (1H, s)

HPLC Retention Time: 10.50 min.
Obs Mass (M$^+$+H): 359.1289
Pred Mass (M$^+$+H): 359.1285
Formula (M): $C_{16}H_{18}N_6O_2S$ Example 53

The compound of Compound No. 53 was synthesized in the similar manner as in Example 52.

| Example | Compound No. | HPLC Retention Time | Obs Mass (M ++ H) | Pred Mass (M ++ H) | Formula(M) | 1HNMR |
|---|---|---|---|---|---|---|
| 53 | 53 | 9.75 | 357.1124 | 357.1128 | C16H16N6O2S | 400 MHz (DMSO d6) 1.75(4H, s), 2.61(3H, s), 2.81(4H, s), 7.01(1H, d, J = 9.2 Hz), 7.83(1H, s), 7.98(1H, d, J = 8.8 Hz), 9.80(1H, s) |

Example 54

The xanthine oxidase inhibitory activity was measured for the compounds synthesized according to the above Examples.

(1) Preparation of Test Compounds

Test compound was dissolved in DMSO (manufactured by Sigma Co.) to prepare a 20 mM solution. The solution was adjusted to an optimal concentration and used for the testing.

(2) Measurement Method

The evaluation of the xanthine oxidase inhibitory activity of the compounds of the present invention was conducted by the method described in the reference (Method Enzymatic Analysis, 1, 521-522, 1974) with partial modification. This evaluation was carried out by measuring oxidase-type xanthine oxidoreductase activity. Concretely, a xanthine (manufactured by Sigma Co.) solution was prepared at 10 mM using a 20 mM sodium hydroxide solution and then mixed with 100 mM phosphate buffer to adjusted to 30 µM. 75 µL of the solution was added to each well of the 96-well plate. The test compound diluted with DMSO at 100 times of a final concentration was added to each well at 1.5 µL per well. After mixing the plate, absorbance at 290 nm was measured by a microplate reader SPECTRA MAX Plus 384 (manufactured by Molecular Devices, LLC). Subsequently, oxidase-type xanthine oxidoreductase (from buttermilk, manufactured by Calbiochem Novabiochem Corp.) was prepared at 30.6 mU/mL using a 100 mM phosphate buffer solution and added to each well at 73.5 µL per well. Immediately after mixing, the change of absorbance at 290 nm was measured for 5 minutes. The enzyme activity of DMSO solution without test compound was used as 100% control, and the inhibitory rate of the test compounds was calculated. Fifty percent inhibitory concentration of the test compounds on the oxidase-type xanthine oxidoreductase activity was calculated by fitting to the dose-response curve.

The results are shown in the following table. Note that the symbols (+, ++, +++) in the table represent inhibitory activity values as shown below.

| Compound No. | Inhibitor Activity |
|---|---|
| 1 | +++ |
| 2 | ++ |
| 3 | ++ |
| 4 | ++ |
| 5 | ++ |
| 6 | ++ |
| 7 | + |
| 8 | + |
| 9 | +++ |
| 10 | ++ |
| 11 | +++ |
| 12 | +++ |
| 13 | +++ |
| 14 | +++ |
| 15 | + |
| 16 | +++ |
| 17 | +++ |
| 18 | +++ |
| 19 | +++ |
| 20 | +++ |
| 21 | +++ |
| 22 | + |
| 23 | + |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | +++ |
| 40 | +++ |
| 41 | +++ |
| 42 | +++ |
| 43 | +++ |
| 44 | +++ |
| 45 | +++ |
| 46 | +++ |
| 47 | +++ |
| 48 | +++ |
| 49 | +++ |
| 50 | +++ |
| 51 | +++ |
| 52 | +++ |
| 53 | +++ |

10.0 nM ≤ IC$_{50}$: +
5.0 nM ≤ IC$_{50}$ < 10.0 nM: ++
1.0 nM ≤ IC$_{50}$ < 5.0 nM: +++

Example 55

Hypouricemic Effect (Normal Rats)

The hypouricemic effect was confirmed for the compounds of compound No. 17, 24, 25 and 26. A test compound suspended in a 0.5% methylcellulose solution was administered to 8 to 9 week-old Sprague-Dawley male rats (Japan Charles River Co.) by oral gavage administration using a feeding needle. After the blood was collected from the tail vein at 2 hours after administration, the plasma was separated. The level of uric acid in the blood sample was measured by uricase method using an absorption spectrometer as well as a uric acid determination kit (L type Wako UA F: Wako Pure Chemical Industries, Ltd.). The percentage of hypouricemic effect was determined by the following expression:

Percentage of hypouricemic effect (%)=(Level of uric acid of the control animal−Level of uric acid of the test compound-administered animal)×100/Level of uric acid of the control animal.

All of compounds of compound No. 17, 24, 25 and 26 showed a hypouricemic effect of 50% or more at the dose of 10 mg/kg.

Further, compounds of compound No. 24, 25 and 26 showed a hypouricemic effect of 50% or more even at the dose of 1 mg/kg.

From the above results, it was shown that the compounds of the present invention have a potent hypouricemic effect.

Example 56

Prolonged Hypouricemic Effect (Normal Rats)

By using compounds of compound No. 17, 25 and 26, a test compound was administered to Sprague-Dawley male rats in the similar manner as in Example 55. After the blood was collected from the tail vein 24 hours after administration, the plasma was separated. The level of uric acid in the blood was measured by an uricase method using an absorption spectrometer and a uric acid determination kit (L type Wako UA F: Wako Pure Chemical Industries, Ltd.). The percentage of hypouricemic effect was determined by the following expression:

Percentage of hypouricemic effect (%)=(Level of uric acid of the control animal−Level of uric acid of the test compound-administered animal)×100/Level of uric acid of the control animal.

All of the compounds of compound No. 17, 25 and 26 showed a hypouricemic effect of 50% or more in 24 hours after administration at the dose of 10 mg/kg.

Further, all of the compounds of compound No. 25 and 26 showed a hypouricemic effect of 40% or more in 24 hours after administration even at the dose of 3 mg/kg.

From the above results, the compounds of the present invention have a prolonged hypouricemic effect over a long period of time.

Example 57

Hypouricemic Effect (Hyperuricemic Beagle dogs)

The hypouricemic effect was confirmed for the compounds of compound No. 25 in oxonic acid-induced hyperuricmic beagle dog. A test compound suspended in a 0.5% methylcellulose solution was administered to beagle dog (Kitayama labes) by oral gavage administration. Potassium oxonate (50 mg/kg) was subcutaneously administrated before and 4 hours after compound administration. After the blood was collected from the cephalic vein at 8 hours after administration, the plasma was separated. The level of uric acid in the plasma sample was measured by LC-MS/MS method and the percentage of hypouricemic effect was determined by the following expression:

Percentage of hypouricemic effect (%)=(Level of uric acid of the control animal−Level of uric acid of the test compound-administered animal)×100/Level of uric acid of the control animal.

Compounds of compound No. 25 showed a hypouricemic effect at the dose of 10 mg/kg.

From the above results, it was shown that the compounds of the present invention have a potent hypouricemic effect in beagle dog.

Example 58

Prolonged inhibitory effect of xanthine oxidase in tissue and plasma.

For "xanthine oxidase" in the present invention, as far as this example, oxidative reaction catalyzing activities which are brought by oxidase-type xanthine oxidoreductase solely and by both oxidase-type and dehydrogenase-type xanthine oxidoreductase are distinguished. The former is "XO activity" and the latter is "XOR activity". In "tissue XO activity", "plasma XO activity", "tissue XOR activity inhibition", "tissue XOR activity inhibition" and the like, "XO activity" and "XOR activity" have the same meanings as defined above. The tissue includes liver, kidney, adipose tissue, intestine and vessel. In addition, percentage of XO activity inhibition and that of XO activity inhibition in same sample are thought to be similar, according to the results below.

The inhibitory effect of tissue XO activity tissue XOR activity and plasma XO activity was confirmed for the compounds of compound No. 17, 25 and 26. A test compound suspended in a 0.5% methylcellulose solution was administered to 7 to 9 week-old Sprague-Dawley male rats (Japan Charles River Co.) by oral gavage administration using a feeding needle. The blood was collected from the abdominal vein and tissue was collected at 24 or 27 hours after administration. Plasma sample was prepared by centrifugation.

Tissue XO activity, tissue XOR activity and plasma XO activity were measured by the pterin-based assay which utilizes the reaction that pterin is oxidized by each type of xanthine oxidoreductase to produce fluorescent isoxanthopterin. In brief, frozen tissues were homogenized with potassium phosphate buffer, pH 7.4, containing 1 mM ethylenediaminetetraacetic acid (EDTA) and protease inhibitors to prepare tissue concentration as follow (liver: 25 mg/mL, kidney: 25 mg/mL, intestine: 5 mg/mL, adipose tissue: 5 mg/mL, vessel: 30 mg/mL). Then the homogenates were centrifuged 12,000 rpm for 15 min at 4° C. When measured XO activity, the supernatant of tissue and plasma were respectively co-incubated with 50 μM pterin solution at 37° C. When measured XOR activity, the supernatant of tissue homogenate was co-incubated with 50 μM pterin and 50 μM methylene blue solution at 37° C. As a control, oxidase-type xanthine oxidoreductase (from buttermilk, manufactured by Calbiochem Novabiochem Corp.) was also incubated with pterin solution in the same manner. XO activity and XOR activity of the samples were determined from fluorescence intensity which normalized by the intensity value of control and protein concentration.

The percentage of XO activity inhibition and XOR activity inhibition were determined by the following expression:

Percentage of XO or XOR activity inhibition (%)= (XO or XOR activity of the control animal−XO or XOR activity of the test compound-administered animal)×100/XO or XOR activity of the control animal.

Liver and kidney XO activities and plasma XO activity 27 hours after compound 17, 25 and 26 administration are shown in the table below.

| | % inhibition of tissue and Plasma XO activity (27 hours after administration) % of inhibition (vs. vehicle) | | | | | |
|---|---|---|---|---|---|---|
| | compound | | | | | |
| | 17 | | 25 | | 26 | |
| | Dose (mg/kg) | | | | | |
| | 1 | 10 | 1 | 10 | 1 | 10 |
| Liver | ≥80% | ≥80% | ≥80% | ≥80% | ≥80% | ≥80% |
| Kidney | ≥60% | ≥70% | ≥60% | ≥70% | ≥60% | ≥70% |
| Plasma | ≥25% | ≥40% | ≥25% | ≥40% | ≥25% | ≥40% |

Intestine, adipose tissue and vessel XOR activities 24 hours after compounds 25 and 26 administration are shown in the table below.

% inhibition of of tissue XO and XOR activity
(At dissection 24 hours after administration) % of inhibition (vs. vehicle)

| | Activity | Compound 25 Dosage (mg/kg) | |
|---|---|---|---|
| | | 1 | 10 |
| Liver | XOR | ≥80% | ≥80% |
| Liver | XO | ≥80% | ≥80% |
| Kidney | XOR | ≥60% | ≥70% |
| Kidney | XO | ≥60% | ≥70% |
| Intestines | XOR | ≥60% | ≥80% |
| Adipose | XOR | ≥30% | ≥60% |
| Blood vessel | XOR | ≥25% | ≥40% |

% inhibition of tissue XOR activity
(At dissection 24 hours after administration) % of inhibition (vs. vehicle)

| | Compound 26 Dosage (mg/kg) | |
|---|---|---|
| | 1 | 10 |
| Blood vessel | ≥30% | ≥50% |

All of compounds of compound No. 17, 25 and 26 inhibited 80% or more XO activity 27 hours after drug administration compared to the control animal at the dose of 10 mg/kg in liver.

All of compounds of compound No. 17, 25 and 26 inhibited 70% or more XO activity 27 hours after drug administration compared to the control animal at the dose of 10 mg/kg in kidney.

All of compounds of compound No. 17, 25 and 26 inhibited 40% or more XO activity 27 hours after drug administration compared to the control animal at the dose of 10 mg/kg in plasma.

In addition, compound No. 25 inhibited 80% or more of each XOR activity and XO activity 24 hours after drug administration compared to the control animal at the dose of 10 mg/kg in liver.

Compound No. 25 inhibited 70% or more of each XOR activity and XO activity 24 hours after drug administration compared to the control animal at the dose of 10 mg/kg in kidney.

In addition, compound No. 25 inhibited 80% or more XOR activity 24 hours after drug administration compared to the control animal at the dose of 10 mg/kg in intestine.

Compound No. 25 inhibited 60% or more XOR activity 24 hours after drug administration compared to the control animal at the dose of 10 mg/kg in adipose tissue.

Compound No. 25 inhibited 40% or more XOR activity 24 hours after drug administration compared to the control animal at the dose of 10 mg/kg in vessel.

Compound No. 26 inhibited 50% or more XOR activity 24 hours after drug administration compared to the control animal at the dose of 10 mg/kg in blood vessel.

Further, all of compounds of compound No. 17, 25 and 26 inhibited 80% or more XO activity 27 hours after drug administration compared to the control animal even at the dose of 1 mg/kg in liver.

All of compounds of compound No. 17, 25 and 26 inhibited 60% or more XO activity 27 hours after drug administration compared to the control animal even at the dose of 1 mg/kg in kidney.

All of compounds of compound No. 17, 25 and 26 inhibited 25% or more XO activity 27 hours after drug administration compared to the control animal even at the dose of 1 mg/kg in plasma.

In addition, compound No. 25 inhibited 80% or more of each XOR activity and XO activity 24 hours after drug administration compared to the control animal at the dose of 1 mg/kg in liver.

Compound No. 25 inhibited 60% or more of each XOR activity and XO activity 24 hours after drug administration compared to the control animal at the dose of 1 mg/kg in kidney.

Compound No. 25 inhibited 60% or more XOR activity 24 hours after drug administration compared to the control animal at the dose of 1 mg/kg in intestine.

Compound No. 25 inhibited 30% or more XOR activity 24 hours after drug administration compared to the control animal at the dose of 1 mg/kg in adipose tissue.

Compound No. 25 inhibited 25% or more XOR activity 24 hours after drug administration compared to the control animal at the dose of 1 mg/kg in blood vessel.

Compound No. 26 inhibited 30% or more XOR activity 24 hours after drug administration compared to the control animal at the dose of 1 mg/kg in blood vessel.

These results show that a compound of the present invention has persistent inhibitory effect for long period on XO and XOR activity in each tissue.

INDUSTRIAL APPLICABILITY

A compound represented by the formula (I) of the present invention and a pharmaceutically acceptable salt thereof can be used as a xanthine oxidase inhibitory drug, a drug for improving vascular endothelial function, a therapeutic agent or a prophylactic agent for diseases associated with xanthine oxidase such as gout, hyperuricemia, tumor lysis syndrome, urinary calculi, hypertension, dyslipidemia, diabetes, kidney diseases such as diabetic nephropathy, respiratory diseases such as chronic obstructive pulmonary disease, inflammatory bowel disease and autoimmune disease, and diseases associated with a vascular endothelial functional disorder such as arteriosclerosis, myocardial infarction, cerebral infarction and cerebrovascular dementia.

The invention claimed is:

1. A method for treating diseases selected from the group consisting of gout, hyperuricemia, tumor lysis syndrome, urinary calculi, hypertension, dyslipidemia, diabetes, diabetic nephropathy, chronic obstructive pulmonary diseases, inflammatory bowel disease, arteriosclerosis, myocardial infarction, and cerebral infarction:

comprising administering an effective amount of a compound represented by the following formula (I) or a pharmaceutically acceptable salt thereof:

wherein, $R_1$ represents OR, NRR' which may form a ring or SR, in which R and R' independently represent a hydrogen atom, an alkyl group having 1 to 8 carbon atoms optionally substituted with one or a plurality of alkoxy groups having 1 to 8 carbon atoms, halogen atoms or hydroxyl groups, or an aryl group optionally substituted with one or a plurality of alkyl groups having 1 to 8 carbon atoms, alkoxy groups having 1 to 8 carbon atoms or halogen atoms, or a heteroaryl group optionally substituted with one or a plurality of alkyl groups having 1 to 8 carbon atoms, alkoxy groups having 1 to 8 carbon atoms or halogen atoms, $R_2$ represents a hydrogen atom or an alkyl group having 1 to 8 carbon atoms, $X_1$, $X_2$ and $X_3$ are independently $CR_3$ or a nitrogen atom, or $X_1$ is $CR_3$ or a nitrogen atom, and $X_2$ and $X_3$ together form a benzene ring, in which $R_3$ is a hydrogen atom or an alkyl group having 1 to 8 carbon atoms.

2. The method according to claim 1, wherein the disease is gout, hyperuricemia, tumor lysis syndrome or diabetic nephropathy.

3. The method according to claim 1, wherein the disease is arteriosclerosis, myocardial infarction or cerebral infarction.

4. The method according to claim 1, wherein $R_1$ is OR.

5. The method according to claim 1, wherein $R_1$ is SR.

6. The method according to claim 1, wherein $R_1$ is NRR' which may form a ring.

7. The method according to claim 1, wherein R and R' are independently an alkyl group having 1 to 8 carbon atoms optionally substituted with one or a plurality of alkoxy groups having 1 to 8 carbon atoms, halogen atoms or hydroxyl groups, or an aryl group optionally substituted with one or a plurality of alkyl groups having 1 to 8 carbon atoms, alkoxy groups having 1 to 8 carbon atoms or halogen atoms.

8. The method according to claim 7, wherein R and R' are independently an alkyl group having 1 to 8 carbon atoms optionally substituted with one or a plurality of alkoxy groups having 1 to 8 carbon atoms, halogen atoms or hydroxyl groups.

9. The method according to claim 8, wherein $R_1$ is OR SR, and R is an isopropyl group, a isobutyl group or a neopentyl group.

10. The method according to claim 1, wherein $R_2$ is a hydrogen atom or an alkyl group having 1 to 3 carbon atoms.

11. The method according to claim 10, wherein $R_2$ is a methyl group.

12. The method according to claim 1, wherein $X_1$, $X_2$ and $X_3$ are independently $CR_3$ or a nitrogen atom.

13. The method according to claim 12, wherein $X_1$ is a nitrogen atom, $X_2$ is $CR_3$ or a nitrogen atom and $X_3$ is $CR_3$.

14. The method according to claim 1, wherein $R_3$ is a hydrogen atom.

15. The method according to claim 1, wherein a compound represented by the formula (I) is 4-methyl-2-[4-(2-methylpropoxy)-3-(1H-1,2,3-triazol-1-yl)phenyl]-1,3-thiazole-5-carboxylic acid, 4-methyl-2-[4-(2-methylpropoxy)-3-(1H-1,2,3,4-tetrazol-1-yl)phenyl]-1,3-thiazole-5-carboxylic acid or 2-[4-(2,2-dimethylpropoxy)-3-(1H-1,2,3,4-tetrazol-1-yl)phenyl]-4-methyl-1,3-thiazole-5-carboxylic acid.

* * * * *